United States Patent
Lipford et al.

(10) Patent No.: US 9,873,694 B2
(45) Date of Patent: Jan. 23, 2018

(54) IMIDAZOLE QUINOLINE-BASED IMMUNE SYSTEM MODULATORS

(71) Applicant: Janus Biotherapeutics, Inc., Cambridge, MA (US)

(72) Inventors: Grayson B. Lipford, Watertown, MA (US); Charles M. Zepp, Hardwick, MA (US)

(73) Assignee: JANUS BIOTHERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 14/349,254

(22) PCT Filed: Oct. 3, 2012

(86) PCT No.: PCT/US2012/058566
§ 371 (c)(1),
(2) Date: Apr. 2, 2014

(87) PCT Pub. No.: WO2013/052550
PCT Pub. Date: Apr. 11, 2013

(65) Prior Publication Data
US 2014/0242121 A1  Aug. 28, 2014

Related U.S. Application Data

(60) Provisional application No. 61/543,082, filed on Oct. 4, 2011.

(51) Int. Cl.
*C07D 471/04* (2006.01)

(52) U.S. Cl.
CPC .................. *C07D 471/04* (2013.01)

(58) Field of Classification Search
CPC ..................................... C07D 471/04
USPC .......... 544/121; 424/278.1; 546/80
See application file for complete search history.

(56) References Cited

U.S. PATENT DOCUMENTS

| | | | |
|---|---|---|---|
| 3,854,480 A | 12/1974 | Zaffaroni | |
| 4,452,775 A | 6/1984 | Kent | |
| 5,075,109 A | 12/1991 | Tice et al. | |
| 5,133,974 A | 7/1992 | Paradissis et al. | |
| 5,407,686 A | 4/1995 | Patel et al. | |
| 5,491,084 A | 2/1996 | Chalfie et al. | |
| 5,736,152 A | 4/1998 | Dunn | |
| 6,194,388 B1 | 2/2001 | Krieg et al. | |
| 6,207,646 B1 | 3/2001 | Krieg et al. | |
| 6,218,371 B1 | 4/2001 | Krieg et al. | |
| 6,239,116 B1 | 5/2001 | Krieg et al. | |
| 6,486,382 B1 | 11/2002 | Gordan-Kamm et al. | |
| 7,943,771 B2 * | 5/2011 | Naddaka | C07D 471/04 546/82 |
| 8,349,866 B2 * | 1/2013 | Yu | C07D 471/04 514/293 |
| 8,728,486 B2 * | 5/2014 | David | C07D 471/04 424/184.1 |
| 2003/0148976 A1 | 8/2003 | Krieg et al. | |
| 2005/0004144 A1 | 1/2005 | Carson et al. | |
| 2007/0232622 A1 | 10/2007 | Lipford et al. | |
| 2008/0177074 A1 * | 7/2008 | Naddaka | C07D 471/04 546/82 |
| 2009/0069314 A1 | 3/2009 | Kshirsagar et al. | |
| 2010/0120741 A1 | 5/2010 | Borchardt et al. | |
| 2010/0158928 A1 | 6/2010 | Stoermer et al. | |
| 2010/0160341 A1 | 6/2010 | Konradi et al. | |
| 2011/0136801 A1 | 6/2011 | Isobe et al. | |

FOREIGN PATENT DOCUMENTS

| | | |
|---|---|---|
| EP | 145340 A2 | 6/1985 |
| EP | 1104764 A1 | 6/2001 |
| EP | 1972629 A1 | 9/2008 |
| WO | WO-98/37919 A1 | 9/1998 |
| WO | WO-98/40100 A1 | 9/1998 |
| WO | WO-98/050547 A1 | 11/1998 |
| WO | WO-98/52581 A1 | 11/1998 |

(Continued)

OTHER PUBLICATIONS

Chen, et al., "Synthesis of Derivatives of 1H-Imidazo [4, 5-c] quinoline," Fine Chemicals-Dalian, vol. 24, No. 3, pp. 304-307 (Total 9 pgs.) (2007).
Adachi, et al., "Targeted Disruption of the MyD88 Gene Results in Loss of IL-1- and IL-18-mediated Function," Immunity, vol. 9, pp. 143-150 (1998).
Aderem, et al., "Toll-like Receptors in the Induction of the Innate Immune Response," Nature, vol. 406, pp. 782-787 (2000).
Alexopoulou, et al., "Recognition of Double-stranded RNA and Activation of NF-kappaB by Toll-like Receptor 3," Nature, vol. 413, pp. 732-738 (2001).
Aliprantis, et al., "Cell activation and apoptosis by bacterial lipoproteins through toll-like receptor-2," Science, vol. 285, pp. 736-739 (1999).
Bauer, et al. "Human TLR9 confers responsiveness to bacterial DNA via species-specific CpG motif recognition," Proc Natl Acad Sci USA, vol. 98, pp. 9237-9242 (2001).

(Continued)

*Primary Examiner* — Rita J Desai
(74) *Attorney, Agent, or Firm* — Wilmer Cutler Pickering Hale and Dorr LLP

(57) ABSTRACT

The present invention relates to a compound of Formula I: or an enantiomer, diastereomer, tautomer, or pharmaceutically acceptable salt or solvate thereof, wherein the symbols are as defined in the specification; a pharmaceutical composition comprising the same; and a method for treating or preventing autoimmunity disease using the same.

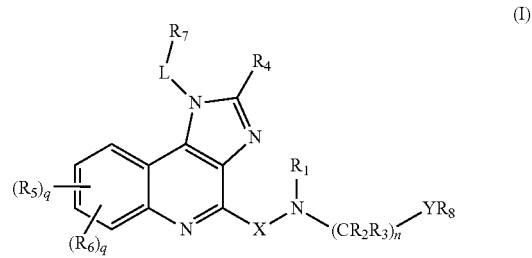

20 Claims, No Drawings

(56) References Cited

FOREIGN PATENT DOCUMENTS

| WO | WO-99/56755 A1 | 11/1999 |
|---|---|---|
| WO | WO-00009506 A1 | 2/2000 |
| WO | WO-01/22990 A2 | 4/2001 |
| WO | WO-01/090151 A2 | 11/2001 |
| WO | WO2007056112 * | 5/2007 |
| WO | WO-2010030785 A2 | 3/2010 |

OTHER PUBLICATIONS

Berge, et al., "Pharmaceutical Salts", J. Pharm. Sci., vol. 66, pp. 1-19 (1977).
Brightbill, et al., "Host defense mechanisms triggered by microbial lipoproteins through toll-like receptors," Science, vol. 285, pp. 732-736 (1999).
Cao, et al., "TRAF6 is a signal transducer for interleukin-1," Nature, vol. 383, pp. 443-446 (1996).
Yoshimura, et al., "Cutting edge: recognition of Gram-positive bacterial cell wall components by the innate immune system occurs via Toll-like receptor 2," J. Immunol, vol. 163, pp. 1-5 (1999).
Extended European Search Report issued by the European Patent Office for Application No. 12837804.9 dated Apr. 17, 2015 (11 pgs.).
Hacker, et al., "Cell type-specific activation of mitogen-activated protein kinases by CpG-DNA controls interleukin-12 release from antigen-presenting cells," EMBO J, vol. 18, pp. 6973-6982 (1999).
Hayashi, et al. "The innate immune response to bacterial flagellin is mediated by Toll-like receptor 5," Nature, vol. 410, pp. 1099-1103 (2001).
Heil, et al., "Species-specific recognition of single-stranded RNA via toll-like receptor 7 and 8," Science, vol. 303, pp. 1526-1529 (2004).
Hemmi, et al., "A Toll-like receptor recognizes bacterial DNA," Nature, vol. 408, pp. 740-745 (2000).
Hemmi, et al., "Small anti-viral compounds activate immune cells via the TLR7 MyD88-dependent signaling pathway," Nat Immunol, vol. 3, No. 2, pp. 196-200 (2002).
Hoshino, et al., "Cutting edge: Toll-like receptor 4 (TLR4)-deficient mice are hyporesponsive to lipopolysaccharide: evidence for TLR4 as the Lps gene product," Immunol, vol. 162, pp. 3749-3752 (1999).
International Search Report and Written Opinion issued by the U.S. Patent and Trademark Office as International Searching Authority for International Application No. PCT/US12/58566 dated Jan. 4, 2013 (12 pgs.).
Langer, R., "New Methods of Drug Delivery," Science, vol. 249, pp. 1527-1533 (1990).
Leadbetter, et al., "Chromatin-IgG Complexes Activate B Cells by Dual Engagement of IgM and Toll-like Receptors," Nature, vol. 416, pp. 603-607 (2002).
Lomaga, et al., "TRAF6 Deficiency Results in osteopetrosis and Defective Interleukin-1, CD40, and LPS Signaling," Genes Dev, vol. 13, pp. 1015-1024 (1999).
Matsuoka, et al., "Production of free light chains of immunoglobulin by a hematopoietic cell line derived from a patient with multiple myeloma," Proc Soc Exp Biol Med, vol. 125, pp. 1246-1250 (1967).
Medzhitov, et al., "A human homologue of the Drosophila Toll protein signals activation of adaptive immunity," Nature, vol. 388, pp. 394-397 (1997).
Medzhitov, et al., "MyD88 is an adaptor protein in the hToll/IL-1 receptor family signaling pathways," Mol Cell, vol. 2, pp. 253-258 (1998).
Murphy, et al., "Regulation of interleukin 12 p40 expression through an NF-kappa B half-site," Mol Cell Biol, vol. 15, pp. 5258-5267 (1995).
Muzio M., et al., "Toll-like receptors: a growing family of immune receptors that are differentially expressed and regulated by different leukocytes," J. Leukoc. Biol. vol. 67, No. 4, pp. 450-456 (2000).
Muzio, et al., "IRAK (Pelle) family member IRAK-2 and MyD88 as proximal mediators of IL-1 signaling," Science, vol. 278, 1612-1615 (1997).
Ozinsky, et al., "The repertoire for pattern recognition of pathogens by the innate immune system is defined by cooperation between toll-like receptors," Proc Natl Acad Sci USA, vol. 97, No. 25, pp. 13766-13771 (2000).
Poltorak, et al., "Defective LPS signaling in C3H/HeJ and C57BL/10ScCr mice: mutations in Tlr4 gene," Science, vol. 282, pp. 2085-2088 (1998).
Sun, et al., "TLR7/9 antagonists as therapeutics for immune-mediated inflammatory disorders," Inflammation and Allergy Drug Targets, vol. 6, pp. 223-235 (2007).
Takeshita, et al., "CpG ODN-mediated regulation of IL-12 p40 transcription," Eur J Immunol, vol. 30, pp. 1967-1976 (2000).
Takeshita, et al., "Positive and negative regulatory elements contribute to CpG oligonucleotide-mediated regulation of human IL-6 gene expression," Eur J Immunol, vol. 30, pp. 108-16 (2000).
Takeuchi, et al., "Differential roles of TLR2 and TLR4 in recognition of gram-negative and gram-positive bacterial cell wall components," Immunity, vol. 11, pp. 443-451 (1999).
Takeuchi, et al., "Discrimination of bacterial lipoproteins by Toll-like receptor 6" Int Immunol, vol. 13, pp. 933-940 (2001).
Underhill, et al., "The Toll-like receptor 2 is recruited to macrophage phagosomes and discriminates between pathogens," Nature, vol. 401, 5 pages (1999).
Vollmer, et al., "Characterization of three CpG oligodeoxynucleotide classes with distinct immunostimulatory activities," Eur J Immunol, vol. 34, pp. 251-262 (2004).
Wesche, et al., "MyD88: an adapter that recruits IRAK to the IL-1 receptor complex," Immunity, vol. 7, pp. 837-847 (1997).
International Search Report and Written Opinion issued by the U.S. Patent and Trademark Office as International Searching Authority for International Application No. PCT/US12/58566 dated Jan. 4, 2013 (10 pgs.).

* cited by examiner

IMIDAZOLE QUINOLINE-BASED IMMUNE SYSTEM MODULATORS

CROSS REFERENCE TO RELATED APPLICATIONS

This application is a National Stage Entry of PCT International Application No. PCT/US12/58566, filed on Oct. 3, 2012, which claims priority to the U.S. Provisional Application No. 61/543,082, filed on Oct. 4, 2011, the contents of which are hereby incorporated by reference in their entirety.

FIELD OF THE INVENTION

The invention relates generally to the field of immunology. More particularly, the invention relates to compositions and methods for altering immune function. More specifically, the invention relates to compositions and methods for affecting immune stimulation mediated through Toll-like receptor (TLR) molecules.

BACKGROUND OF THE INVENTION

Stimulation of the immune system, which includes stimulation of either or both innate immunity and adaptive immunity, is a complex phenomenon that can result in either protective or adverse physiologic outcomes for the host. In recent years there has been increased interest in the mechanisms underlying innate immunity, which is believed to initiate and support adaptive immunity. This interest has been fueled in part by the recent discovery of a family of highly conserved pattern recognition receptor proteins known as Toll-like receptors (TLRs) believed to be involved in innate immunity as receptors for pathogen-associated molecular patterns (PAMPs). Compositions and methods useful for modulating innate immunity are therefore of great interest, as they may affect therapeutic approaches to conditions involving autoimmunity, inflammation, allergy, asthma, graft rejection, graft versus host disease (GvHD), infection, cancer, vaccine technology, and immunodeficiency.

Toll-like receptors (TLRs) are a family of pattern recognition and signaling molecules involved in innate immunity. This family includes at least ten human members, designated TLR1-TLR10, for which the function and specificity are known for most but not all members. Certain of these TLRs are known to signal in response to encounter with particular types of nucleic acid molecules. For example, TLR9 signals in response to CpG-containing DNA, TLR3 signals in response to double-stranded RNA, and TLR7 and TLR8 signal in response to certain single-stranded RNA. There have been a number of reports describing the immunostimulatory effect of certain types of nucleic acid molecules, including CpG nucleic acids and double-stranded RNA. Of note, it was reported that Toll-like receptor 9 (TLR9) recognizes bacterial DNA and CpG DNA while TLR7 and 8 recognize single stranded RNA: Hemmi H., et al. (2000) Nature 408:740-5; Bauer S. et al. (2001) Proc. Natl. Acad. Sci. USA 98:9237-42; Heil, et al. (2004) Science, 303:1526. In addition to their natural ligands, certain synthetic or artificial ligands for these nucleic-acid responsive TLRs are also known. These include certain CpG oligodeoxyribonucleotides (CpG ODN), oligoribonucleotides (ORN) and certain ORN analogs, and certain small molecules including imiquimod (R-837) and resiquimod (R-848). Imiquimod and resiquimod are classified as imidazoaminoquinoline-4-amines; the former is currently marketed as Aldara™ by 3M Pharmaceuticals for topical treatment of anogenital warts associated with papillomavirus infection. In addition to their use in the treatment of certain viral infections such as papillomavirus, certain TLR agonists are also believed to be useful as adjuvants, antitumor agents, and anti-allergy agents. Because a number of diseases and conditions can be treated by enhancing innate immunity, there is a continued need for additional and improved TLR agonists.

It was also recently reported that immune complexes containing IgG and nucleic acid can stimulate TLR9 and participate in B-cell activation in certain autoimmune diseases. Leadbetter E. A., et al. (2002) Nature 416:595-8. Similar and additional documentation of these claims have been made for TLR7, 8 and 9: reviewed in Sun S., et al. (2007) Inflammation and Allergy—Drug Targets 6:223-235.

SUMMARY OF THE INVENTION

Compounds as immune system modulators bearing an imidazoquinoline core are described. The molecules described herein can alter TLR-mediated immunostimulatory signaling by inhibiting TLR signaling and thus can be useful as inhibitors of immune stimulation. Compositions and methods described herein are useful for inhibiting immune stimulation in vitro and in vivo. Such compositions and methods thus are useful in a number of clinical applications, including as pharmaceutical agents and methods for treating conditions involving unwanted immune activity, including inflammatory and autoimmune disorders. The compositions of the invention can also be used in methods for the preparation of medicaments for use in the treatment of conditions involving unwanted immune activity, including a variety of inflammatory and autoimmune disorders.

In one aspect, the present invention provides a compound of Formula I, or a pharmaceutically acceptable salt thereof,

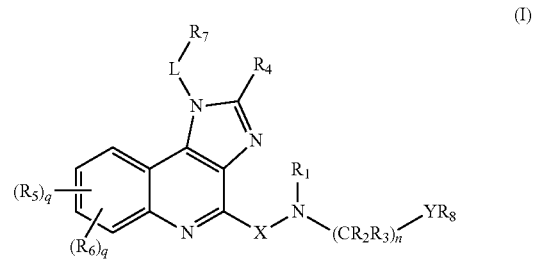

wherein
X is absent or is an alkyl, cycloalkyl, aryl, aralkyl, or heterocycle;
each occurrence of $R_1$ is independently hydrogen, alkyl, cycloalkyl, alkenyl, cycloalkenyl, alkynyl, heterocycle, or aryl;
each occurrence of $R_2$ and $R_3$ is independently hydrogen, alkyl, cycloalkyl, OH, alkoxy, —$(CH_2)_pNR_aR_b$, or $R_2$ and $R_3$ together with the carbon atom to which they are bonded optionally form a $(C_3-C_7)$cycloalkyl;
n is an integer of 2-4;
each q is an integer of 1-2;
Y is $NR_9$ or O;
$R_8$ is hydrogen, alkyl, cycloalkyl, monocyclic heterocycle, or aryl;
$R_9$ is H, Me, Et, n-Pr, i-Pr, n-Bu, i-Bu, t-Bu, $CH_2CMe_3$, Ph, $CH_2Ph$, $C(=O)R_{12}$, $(CH_2)_pOR_a$, and $(CH_2)_pNR_bR_c$, wherein R$_{12}$ is alkyl, phenyl, or heterocycle; R$_a$, R$_b$ and R$_c$ are each independently hydrogen, or (C$_1$-C$_4$)alkyl, or R$_b$ and R$_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said R$_8$ and R$_9$ together with the nitrogen atom to which they are bonded optionally form a heterocycle comprising 1-4 heteroatoms, wherein the heterocycle is optionally substituted by (C$_1$-C$_4$)alkyl;

or R$_1$ and R$_8$ optionally form a heterocycle comprising 2-4 heteroatoms, wherein the heterocycle is optionally substituted by (C$_1$-C$_4$)alkyl;

R$_4$ is hydrogen, halogen, cyano, nitro, CF$_3$, OCF$_3$, alkyl, cycloalkyl, alkenyl, aryl, heterocycle, OR$_a$, —CH$_2$OR$_a$, SR$_a$, S(=O)R$_a$, S(=O)$_2$R$_a$, NR$_b$R$_c$, S(=O)$_2$NR$_b$R$_c$, C(=O)OR$_a$, C(=O)R$_a$, C(=O)NR$_b$R$_c$, OC(=O)R$_a$, OC(=O)NR$_b$R$_c$, NR$_b$C(=O)OR$_a$, NR$_b$C(=O)R$_a$;

R$_5$ and R$_6$ are each independently hydrogen, halogen, cyano, nitro, CF$_3$, OCF$_3$, alkyl, cycloalkyl, alkenyl, aryl, heterocycle, OR$_a$, SR$_a$, S(=O)R$_a$, S(=O)$_2$R$_a$, NR$_b$R$_c$, S(=O)$_2$NR$_b$R$_c$, C(=O)OR$_a$, C(=O)R$_a$, C(=O)NR$_b$R$_c$, OC(=O)R$_a$, OC(=O)NR$_b$R$_c$, NR$_b$C(=O)OR$_a$, NR$_b$C(=O)R$_a$, alkaryl, alkylheterocyclic, or NR$_b$(CH$_2$)$_p$NR$_b$R$_c$; or said R$_5$ and R$_6$ together with the carbon atoms to which they are bonded optionally form a heterocycle comprising 1-4 heteroatoms, wherein the heterocycle is optionally substituted by (C$_1$-C$_4$)alkyl;

L is absent or is alkyl or alkenyl containing from 2 to 10 carbon atoms;

R$_7$ is H, alkyl, heteroaryl, —O(CH$_2$)$_p$OR$_a$, or NR$_{10}$R$_{11}$, wherein the heteroaryl are optionally substituted by (C$_1$-C$_4$) alkyl;

R$_{10}$ and R$_{11}$ are each independently hydrogen, alkyl, cycloalkyl, alkenyl, aryl or alkylaryl, or R$_{10}$ and R$_{11}$ together with the nitrogen atom to which they are bonded form a heterocycle;

p is an integer of 0, 1, 2, 3, 4, 5, or 6;

each occurrence of R$_a$ is independently hydrogen, alkyl, cycloalkyl, alkenyl, cycloalkenyl, alkynyl, heterocycle, or aryl; and each occurrence of R$_b$, and R$_c$ is independently hydrogen, alkyl, cycloalkyl, heterocycle, aryl, or said R$_b$ and R$_c$ together with the nitrogen atom to which they are bonded optionally form a heterocycle comprising 1-4 heteroatoms, wherein the heterocycle is optionally substituted by (C$_1$-C$_4$) alkyl.

In some embodiments, X is absent. In other embodiments, X is alkyl. In yet other embodiments, X is cycloalkyl. In yet other embodiments, X is heterocycle. In yet other embodiments, X is aralkyl. In yet other embodiments, X is -phenyl-(CH$_2$)—.

In any of the preceding embodiments, L is alkyl or alkenyl containing from 2 to 4 carbon atoms.

In some embodiments, the compound has the structure of Formula II:

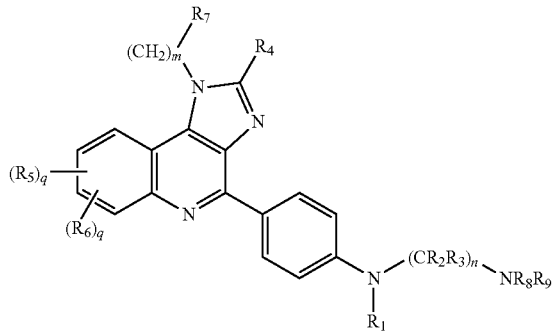

(II)

wherein each occurrence of R$_1$ is independently hydrogen, (C$_1$-C$_4$)alkyl, (C$_3$-C$_7$)cycloalkyl, (C$_2$-C$_6$)alkenyl, (C$_2$-C$_6$)alkynyl, aryl or a 5- to 7-membered heterocycle which may be saturated or unsaturated containing one to three heteroatoms which may the same or different selected from nitrogen, sulfur and oxygen, in which the heterocycle is optionally substituted by (C$_1$-C$_4$)alkyl, phenyl or benzyl;

each occurrence of R$_2$ and R$_3$ is independently hydrogen, (C$_1$-C$_4$)alkyl, (C$_3$-C$_7$)cycloalkyl, OH, (C$_1$-C$_4$)alkoxy, —(CH$_2$)$_p$NR$_a$R$_b$, or R$_2$ and R$_3$ together with the carbon atom to which they are bonded optionally form a (C$_3$-C$_6$) cycloalkyl;

R$_8$ is hydrogen, (C$_1$-C$_4$)alkyl, (C$_3$-C$_7$)cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by (C$_1$-C$_4$)alkyl, phenyl or benzyl;

R$_9$ is H, Me, Et, n-Pr, i-Pr, n-Bu, i-Bu, t-Bu, CH$_2$CMe$_3$, Ph, CH$_2$Ph, C(=O)R$_{12}$, (CH$_2$)$_p$OR$_a$, and (CH$_2$)$_p$NR$_b$R$_c$, wherein R$_{12}$ is (C$_1$-C$_4$)alkyl, phenyl, or a 5- to 7-membered heterocycle which may be saturated or unsaturated containing one to three heteroatoms which may the same or different selected from nitrogen, sulfur and oxygen, in which the heterocycle is optionally substituted by (C$_1$-C$_4$)alkyl, phenyl or benzyl; R$_a$, R$_b$ and R$_c$ are each independently hydrogen, or (C$_1$-C$_4$)alkyl, or R$_b$ and R$_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said R$_8$ and R$_9$ together with the nitrogen atom to which they are bonded optionally form a 3- to 7-membered heterocycle which may be saturated or unsaturated comprising 1-4 heteroatoms, wherein the heterocycle is optionally substituted by (C$_1$-C$_4$)alkyl;

or R$_1$ and R$_8$ optionally form a 5- to 7-membered heterocycle which may be saturated or unsaturated comprising 2-4 heteroatoms, wherein the heterocycle is optionally substituted by (C$_1$-C$_4$)alkyl;

R$_4$ is hydrogen, halogen, cyano, nitro, CF$_3$, OCF$_3$, (C$_1$-C$_4$)alkyl, (C$_3$-C$_7$)cycloalkyl, (C$_2$-C$_6$)alkenyl, aryl, heterocycle, OR$_a$, —CH$_2$OR$_a$, SR$_a$, S(=O)R$_a$, S(=O)$_2$R$_a$, NR$_b$R$_c$, S(=O)$_2$NR$_b$R$_c$, C(=O)OR$_a$, C(=O)R$_a$, C(=O) NR$_b$R$_c$, OC(=O)R$_a$, OC(=O)NR$_b$R$_c$, NR$_b$C(=O)OR$_a$, $NR_bC(=O)R_a$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

$R_5$ and $R_6$ are each independently hydrogen, halogen, cyano, nitro, $CF_3$, $OCF_3$, $(C_1$-$C_4)$alkyl, $(C_3$-$C_7)$cycloalkyl, $(C_2$-$C_6)$alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, alkaryl, alkylheterocyclic, or $NR_b(CH_2)_pNR_bR_c$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

L is alkyl or alkenyl containing from 2 to 10 carbon atoms;

$R_7$ is H, $(C_1$-$C_4)$alkyl, heteroaryl, $—O(CH_2)_pOR_a$, or $NR_{10}R_{11}$, wherein the heteroaryl is a 5- to 6-membered aromatic ring which may be saturated or unsaturated containing one to three heteroatoms which may the same or different selected from nitrogen, sulfur and oxygen, and the heteroaryl is optionally substituted by $(C_1$-$C_4)$alkyl;

$R_{10}$ and $R_{11}$ are each independently hydrogen, $(C_1$-$C_4)$alkyl, $(C_3$-$C_7)$cycloalkyl, $(C_2$-$C_6)$alkenyl, aryl or $(C_1$-$C_4)$alkylaryl, or $R_{10}$ and $R_{11}$ together with the nitrogen atom to which they are bonded form a 3- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

m is an integer of 2-6;

n is an integer of 2-4;

each q is an integer of 1-2;

each occurrence of $R_a$ is independently hydrogen, $(C_1$-$C_4)$alkyl, $(C_3$-$C_7)$cycloalkyl, $(C_2$-$C_6)$alkenyl, $(C_5$-$C_7)$cycloalkenyl, $(C_2$-$C_6)$alkynyl, aryl, or a 3- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; and each occurrence of $R_b$ and $R_c$ is independently hydrogen, $(C_1$-$C_4)$alkyl, $(C_3$-$C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; or said $R_b$ and $R_c$ together with the nitrogen atom to which they are bonded optionally form a 3- to 7-membered heterocycle which may be saturated or unsaturated comprising 1-4 heteroatoms, wherein the heterocycle is optionally substituted by $(C_1$-$C_4)$alkyl.

In some embodiments, the compound of Formula I has the structure of Formula III:

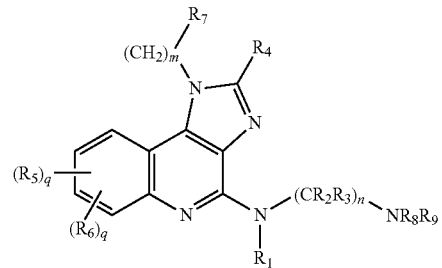

(III)

wherein each occurrence of $R_1$ is independently hydrogen, $(C_1$-$C_4)$alkyl, $(C_3$-$C_7)$cycloalkyl, $(C_2$-$C_6)$alkenyl, $(C_2$-$C_6)$alkynyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

each occurrence of $R_2$ and $R_3$ is independently hydrogen, $(C_1$-$C_4)$alkyl, $(C_3$-$C_7)$cycloalkyl, OH, $(C_1$-$C_4)$alkoxy, $—(CH_2)_pNR_aR_b$, or $R_2$ and $R_3$ together with the carbon atom to which they are bonded optionally form a $(C_3$-$C_6)$ cycloalkyl;

$R_8$ is hydrogen, $(C_1$-$C_4)$alkyl, $(C_3$-$C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

$R_9$ is H, Me, Et, n-Pr, i-Pr, n-Bu, i-Bu, t-Bu, $CH_2CMe_3$, Ph, $CH_2$Ph, $C(=O)R_{12}$, $(CH_2)_pOR_a$, and $(CH_2)_pNR_bR_c$, wherein $R_{12}$ is $(C_1$-$C_4)$alkyl, phenyl, or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; $R_a$, $R_b$ and $R_c$ are each independently hydrogen, or $(C_1$-$C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a 3- to 7-membered heterocycle which may be saturated or unsaturated comprising 1-4 heteroatoms, wherein the heterocycle is optionally substituted by $(C_1$-$C_4)$alkyl;

or $R_1$ and $R_8$ optionally form a 5- to 7-membered heterocycle which may be saturated or unsaturated comprising 2-4 heteroatoms, wherein the heterocycle is optionally substituted by $(C_1$-$C_4)$alkyl;

$R_4$ is hydrogen, halogen, cyano, nitro, $CF_3$, $OCF_3$, $(C_1$-$C_4)$alkyl, $(C_3$-$C_7)$cycloalkyl, $(C_2$-$C_6)$alkenyl, aryl, heterocycle, $OR_a$, $—CH_2OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

$R_5$ and $R_6$ are each independently hydrogen, halogen, cyano, nitro, $CF_3$, $OCF_3$, $(C_1-C_4)$alkyl, $(C_3-C_7)$cycloalkyl, $(C_2-C_6)$alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, alkaryl, alkylheterocyclic, or $NR_b(CH_2)_pNR_bR_c$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

L is alkyl or alkenyl containing from 2 to 10 carbon atoms;

$R_7$ is H, $(C_1-C_4)$alkyl, heteroaryl, $-O(CH_2)_pOR_a$, or $NR_{10}R_{11}$, wherein the heteroaryl is a 5- to 6-membered aromatic ring which may be saturated or unsaturated containing one to three heteroatoms which may the same or different selected from nitrogen, sulfur and oxygen, and the heteroaryl is optionally substituted by $(C_1-C_4)$alkyl;

m is an integer of 2-6;
n is an integer of 2-4;
each q is an integer of 1-2;

$R_{10}$ and $R_{11}$ are each independently hydrogen, $(C_1-C_4)$alkyl, $(C_3-C_7)$cycloalkyl, $(C_2-C_6)$alkenyl, aryl or $(C_1-C_4)$alkylaryl, or $R_{10}$ and $R_{11}$ together with the nitrogen atom to which they are bonded form a 3- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

each occurrence of $R_a$ is independently hydrogen, $(C_1-C_4)$alkyl, $(C_3-C_7)$cycloalkyl, $(C_2-C_6)$alkenyl, $(C_5-C_7)$cycloalkenyl, $(C_2-C_6)$alkynyl, aryl, or a 3- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl; and each occurrence of $R_b$ and $R_c$ is independently hydrogen, $(C_1-C_4)$alkyl, $(C_3-C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl; or said $R_b$ and $R_c$ together with the nitrogen atom to which they are bonded optionally form a 3- to 7-membered heterocycle which may be saturated or unsaturated comprising 1-4 heteroatoms, wherein the heterocycle is optionally substituted by $(C_1-C_4)$alkyl.

In some embodiments, $R_7$ is $NR_{10}R_{11}$, in which $R_{10}$ and $R_{11}$ are each independently hydrogen, $(C_1-C_4)$alkyl, or $(C_1-C_4)$alkylaryl.

In some embodiments, $R_7$ is $NR_{10}R_{11}$, in which $R_{10}$ and $R_{11}$ together with the nitrogen atom to which they are bonded form a 3- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl.

In some embodiments, $NR_{10}R_{11}$ and $NR_8R_9$ are each independently a heterocycle selected from

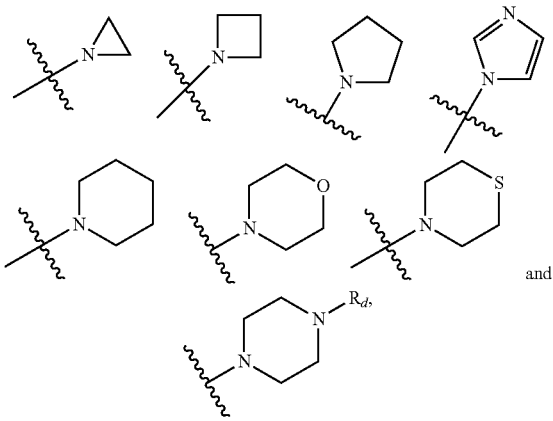

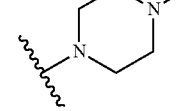

in which $R_d$ is H, Me, Et, n-Pr, i-Pr, n-Bu, i-Bu, t-Bu, $CH_2CMe_3$, Ph, $CH_2Ph$, $C(=O)R_{12}$, $(CH_2)_pOR_a$, and $(CH_2)_pNR_bR_c$, wherein $R_{12}$ is alkyl, phenyl, or heterocycle; $R_a$, $R_b$ and $R_c$ are each independently hydrogen, or $(C_1-C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4.

In some embodiments, $NR_{10}R_{11}$ and $NR_8R_9$ are each independently a heterocycle selected from

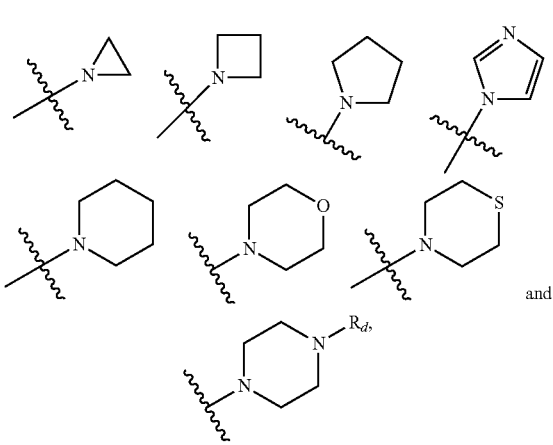

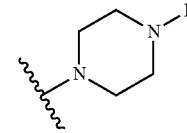

in which $R_d$ is H, Me, Et, n-Pr, i-Pr, n-Bu, i-Bu, t-Bu, $CH_2CMe_3$, Ph, or $CH_2Ph$.

In some embodiments, $R_1$ and $R_8$ together form a heterocycle comprising 2-4 heteroatoms, wherein the heterocycle is optionally substituted by $(C_1-C_4)$alkyl.

In some embodiments, $R_1$ and $R_8$ together form

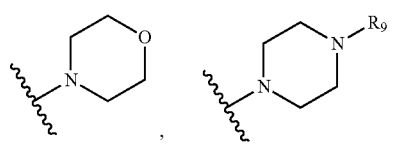

or

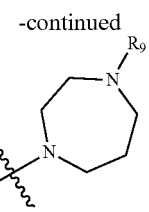

in which R₉ is H, Me, Et, n-Pr, i-Pr, n-Bu, i-Bu, t-Bu, CH₂CMe₃, Ph, CH₂Ph, C(=O)R₁₂, (CH₂)$_p$OR$_a$, and (CH₂)$_p$NR$_b$R$_c$, wherein R₁₂ is alkyl, phenyl, or heterocycle; R$_a$, R$_b$ and R$_c$ are each independently hydrogen, or (C₁-C₄)alkyl, or R$_b$ and R$_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4.

In some embodiments, R$_d$ is H, Me, Et, n-Pr, i-Pr, n-Bu, i-Bu, t-Bu, CH₂CMe₃, Ph, or CH₂Ph.

In some embodiments, R₁ is H. In some embodiments, R₂ and R₃ are each independently H. In some embodiments, the compound is selected from Tables 1-2.

In another aspect, a pharmaceutical composition is described, comprising at least one a compound of Formula I as described herein, or a pharmaceutically acceptable salt thereof, and a pharmaceutically-acceptable carrier or diluent,

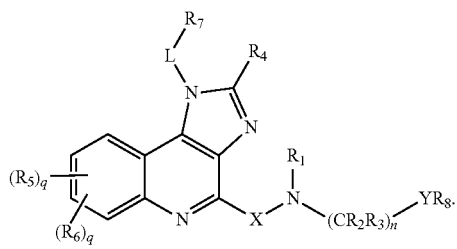

In yet another aspect, a method of treating an autoimmune disease in a mammalian species in need thereof is described, comprising administering to the mammalian species a therapeutically effective amount of at least one compound of Formula I as described herein,

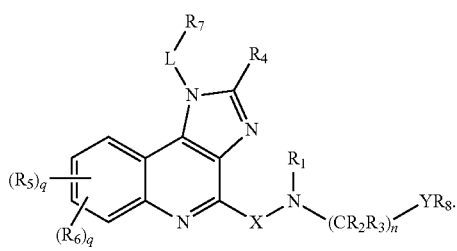

In some embodiments, the autoimmune disease is selected from cutaneous and systemic lupus erythematosus, insulin-dependent diabetes mellitus, rheumatoid arthritis, multiple sclerosis, atherosclerosis, psoriasis, psoriatic arthritis, inflammatory bowel disease, ankylosing spondylitis, autoimmune hemolytic anemia, Behcet's syndrome, Goodpasture's syndrome, Graves' disease, Guillain-Barre syndrome, Hashimoto's thyroiditis, idiopathic thrombocytopenia, io myasthenia gravis, pernicious anemia, polyarteritis nodosa, polymyositis/dermatomyositis, primary biliary sclerosis, sarcoidosis, sclerosing cholangitis, Sjogren's syndrome, systemic sclerosis (scleroderma and CREST syndrome), Takayasu's arteritis, temporal arteritis, Wegener's granulomatosis, antiphospholipid syndrome and autoimmune associated cardiovascular disease. In some specific embodiments, the autoimmune disease is systemic lupus erythematosus. In some specific embodiments, the autoimmune disease is insulin-dependent diabetes mellitus. In some specific embodiments, the autoimmune disease is rheumatoid arthritis. In some specific embodiments, the autoimmune disease is multiple sclerosis. In some specific embodiments, the autoimmune disease is multiple sclerosis. In some specific embodiments, the autoimmune disease is Sjogren's syndrome. In some specific embodiments, the autoimmune disease is psoriasis.

In yet another aspect, a method of inhibiting TLR-mediated immunostimulation in a mammalian species in need thereof is described, comprising administering to the mammalian species a therapeutically effective amount of at least one compound of Formula I,

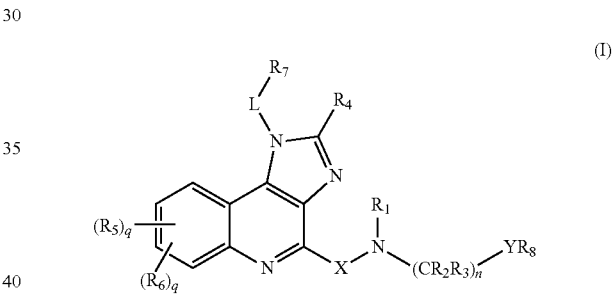

wherein
X is absent or is an alkyl, cycloalkyl, aryl, aralkyl, or heterocycle;
each occurrence of R₁ is independently hydrogen, alkyl, cycloalkyl, alkenyl, cycloalkenyl, alkynyl, heterocycle, or aryl;
each occurrence of R₂ and R₃ is independently hydrogen, alkyl, cycloalkyl, OH, alkoxy, —(CH₂)$_p$NR$_a$R$_b$, or R₂ and R₃ together with the carbon atom to which they are bonded optionally form a (C₃-C₇)cycloalkyl;
n is an integer of 2-4;
each q is an integer of 1-2;
Y is NR₉ or O;
R₈ is hydrogen, alkyl, cycloalkyl, monocyclic heterocycle, or aryl;
R₉ is H, Me, Et, n-Pr, i-Pr, n-Bu, i-Bu, t-Bu, CH₂CMe₃, Ph, CH₂Ph, C(=O)R₁₂, (CH₂)$_p$OR$_a$, and (CH₂)$_p$NR$_b$R$_c$, wherein R₁₂ is alkyl, phenyl, or heterocycle; R$_a$, R$_b$ and R$_c$ are each independently hydrogen, or (C₁-C₄)alkyl, or R$_b$ and R$_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a heterocycle comprising 1-4 heteroatoms, wherein the heterocycle is optionally substituted by $(C_1-C_4)$alkyl;

or $R_1$ and $R_8$ optionally form a heterocycle comprising 2-4 heteroatoms, wherein the heterocycle is optionally substituted by $(C_1-C_4)$alkyl;

$R_4$ is hydrogen, halogen, cyano, nitro, $CF_3$, $OCF_3$, alkyl, cycloalkyl, alkenyl, aryl, heterocycle, $OR_a$, —$CH_2OR_a$, $SR_a$, $S(\!=\!O)R_a$, $S(\!=\!O)_2R_a$, $NR_bR_c$, $S(\!=\!O)_2NR_bR_c$, $C(\!=\!O)OR_a$, $C(\!=\!O)R_a$, $C(\!=\!O)NR_bR_c$, $OC(\!=\!O)R_a$, $OC(\!=\!O)NR_bR_c$, $NR_bC(\!=\!O)OR_a$, $NR_bC(\!=\!O)R_a$;

$R_5$ and $R_6$ are each independently hydrogen, halogen, cyano, nitro, $CF_3$, $OCF_3$, alkyl, cycloalkyl, alkenyl, aryl, heterocycle, $OR_a$, $SR_a$, $S(\!=\!O)R_a$, $S(\!=\!O)_2R_a$, $NR_bR_c$, $S(\!=\!O)_2NR_bR_c$, $C(\!=\!O)OR_a$, $C(\!=\!O)R_a$, $C(\!=\!O)NR_bR_c$, $OC(\!=\!O)R_a$, $OC(\!=\!O)NR_bR_c$, $NR_bC(\!=\!O)OR_a$, $NR_bC(\!=\!O)R_a$, alkaryl, alkylheterocyclic, or $NR_b(CH_2)_pNR_bR_c$; or said $R_5$ and $R_6$ together with the carbon atoms to which they are bonded optionally form a heterocycle comprising 1-4 heteroatoms, wherein the heterocycle is optionally substituted by $(C_1-C_4)$alkyl;

L is absent or is alkyl or alkenyl containing from 2 to 10 carbon atoms;

$R_7$ is H, alkyl, heteroaryl, —$O(CH_2)_pOR_a$, or $NR_{10}R_{11}$, wherein the heteroaryl are optionally substituted by $(C_1-C_4)$alkyl;

$R_{10}$ and $R_{11}$ are each independently hydrogen, alkyl, cycloalkyl, alkenyl, aryl or alkylaryl, or $R_{10}$ and $R_{11}$ together with the nitrogen atom to which they are bonded form a heterocycle;

p is an integer of 0, 1, 2, 3, 4, 5, or 6;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle comprising 1-4 heteroatoms, wherein the heterocycle is optionally substituted by $(C_1-C_4)$alkyl.

In yet another aspect, a method of inhibiting TLR-mediated immunostimulatory signaling is described, comprising contacting a cell expressing a TLR with an effective amount of at least one compound of Formula I,

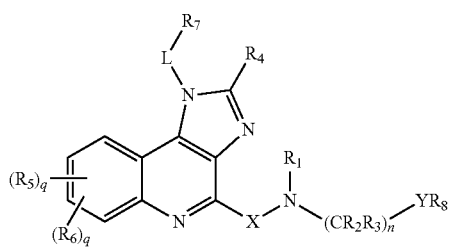

(I)

wherein

X is absent or is an alkyl, cycloalkyl, aryl, aralkyl, or heterocycle;

each occurrence of $R_1$ is independently hydrogen, alkyl, cycloalkyl, alkenyl, cycloalkenyl, alkynyl, heterocycle, or aryl;

each occurrence of $R_2$ and $R_3$ is independently hydrogen, alkyl, cycloalkyl, OH, alkoxy, —$(CH_2)_pNR_aR_b$, or $R_2$ and $R_3$ together with the carbon atom to which they are bonded optionally form a $(C_3-C_7)$cycloalkyl;

n is an integer of 2-4;

each q is an integer of 1-2;

Y is $NR_9$ or O;

$R_8$ is hydrogen, alkyl, cycloalkyl, monocyclic heterocycle, or aryl;

$R_9$ is H, Me, Et, n-Pr, i-Pr, n-Bu, i-Bu, t-Bu, $CH_2CMe_3$, Ph, $CH_2Ph$, $C(\!=\!O)R_{12}$, $(CH_2)_pOR_a$, and $(CH_2)_pNR_bR_c$, wherein $R_{12}$ is alkyl, phenyl, or heterocycle; $R_a$, $R_b$ and $R_c$ are each independently hydrogen, or $(C_1-C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a heterocycle comprising 1-4 heteroatoms, wherein the heterocycle is optionally substituted by $(C_1-C_4)$alkyl;

or $R_1$ and $R_8$ optionally form a heterocycle comprising 2-4 heteroatoms, wherein the heterocycle is optionally substituted by $(C_1-C_4)$alkyl;

$R_4$ is hydrogen, halogen, cyano, nitro, $CF_3$, $OCF_3$, alkyl, cycloalkyl, alkenyl, aryl, heterocycle, $OR_a$, —$CH_2OR_a$, $SR_a$, $S(\!=\!O)R_a$, $S(\!=\!O)_2R_a$, $NR_bR_c$, $S(\!=\!O)_2NR_bR_c$, $C(\!=\!O)OR_a$, $C(\!=\!O)R_a$, $C(\!=\!O)NR_bR_c$, $OC(\!=\!O)R_a$, $OC(\!=\!O)NR_bR_c$, $NR_bC(\!=\!O)OR_a$, $NR_bC(\!=\!O)R_a$;

$R_5$ and $R_6$ are each independently hydrogen, halogen, cyano, nitro, $CF_3$, $OCF_3$, alkyl, cycloalkyl, alkenyl, aryl, heterocycle, $OR_a$, $SR_a$, $S(\!=\!O)R_a$, $S(\!=\!O)_2R_a$, $NR_bR_c$, $S(\!=\!O)_2NR_bR_c$, $C(\!=\!O)OR_a$, $C(\!=\!O)R_a$, $C(\!=\!O)NR_bR_c$, $OC(\!=\!O)R_a$, $OC(\!=\!O)NR_bR_c$, $NR_bC(\!=\!O)OR_a$, $NR_bC(\!=\!O)R_a$, alkaryl, alkylheterocyclic, or $NR_b(CH_2)_pNR_bR_c$; or said $R_5$ and $R_6$ together with the carbon atoms to which they are bonded optionally form a heterocycle comprising 1-4 heteroatoms, wherein the heterocycle is optionally substituted by $(C_1-C_4)$alkyl;

L is absent or is alkyl or alkenyl containing from 2 to 10 carbon atoms;

$R_7$ is H, alkyl, heteroaryl, —$O(CH_2)_pOR_a$, or $NR_{10}R_{11}$, wherein the heteroaryl are optionally substituted by $(C_1-C_4)$alkyl;

$R_{10}$ and $R_{11}$ are each independently hydrogen, alkyl, cycloalkyl, alkenyl, aryl or alkylaryl, or $R_{10}$ and $R_{11}$ together with the nitrogen atom to which they are bonded form a heterocycle;

p is an integer of 0, 1, 2, 3, 4, 5, or 6;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle comprising 1-4 heteroatoms, wherein the heterocycle is optionally substituted by $(C_1-C_4)$alkyl.

FURTHER DESCRIPTION OF THE INVENTION

Definitions

The following are definitions of terms used in the present specification. The initial definition provided for a group or term herein applies to that group or term throughout the present specification individually or as part of another group, unless otherwise indicated. Unless otherwise defined, all technical and scientific terms used herein have the same meaning as commonly understood by one of ordinary skill in the art.

The terms "alkyl" and "alk" refer to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "($C_1$-$C_4$) alkyl" refers to a straight or branched chain alkane (hydrocarbon) radical containing from 1 to 4 carbon atoms, such as methyl, ethyl, propyl, isopropyl, n-butyl, t-butyl, and isobutyl. "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. In the aforementioned exemplary substituents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplary such groups include ethenyl or allyl. The term "$C_2$-$C_6$ alkenyl" refers to a straight or branched chain hydrocarbon radical containing from 2 to 6 carbon atoms and at least one carbon-carbon double bond, such as ethylenyl, propenyl, 2-propenyl, (E)-but-2-enyl, (Z)-but-2-enyl, 2-methy(E)-but-2-enyl, 2-methy(Z)-but-2-enyl, 2,3-dimethyl-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. "Substituted alkenyl" refers to an alkenyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted.

The term "alkynyl" refers to a straight or branched chain hydrocarbon radical containing from 2 to 12 carbon atoms and at least one carbon to carbon triple bond. Exemplary such groups include ethynyl. The term "$C_2$-$C_6$ alkynyl" refers to a straight or branched chain hydrocarbon radical containing from 2 to 6 carbon atoms and at least one carbon-carbon triple bond, such as ethynyl, prop-1-ynyl, prop-2-ynyl, but-1-ynyl, but-2-ynyl, pent-1-ynyl, pent-2-ynyl, hex-1-ynyl, hex-2-ynyl, hex-3-ynyl. "Substituted alkynyl" refers to an alkynyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted.

The term "cycloalkyl" refers to a fully saturated cyclic hydrocarbon group containing from 1 to 4 rings and 3 to 8 carbons per ring. "$C_3$-$C_7$ cycloalkyl" refers to cyclopropyl, cyclobutyl, cyclopentyl, cyclohexyl, or cycloheptyl. "Substituted cycloalkyl" refers to a cycloalkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, OCF3, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include fused cyclic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

The term "carbocycle" refers to a fully saturated or partially saturated cyclic hydrocarbon group containing from 1 to 4 rings and 3 to 8 carbons per ring, or cyclic, aromatic hydrocarbon groups that have 1 to 5 aromatic rings, especially monocyclic or bicyclic groups such as phenyl, biphenyl or naphthyl. The term "carbocycle" encompasses cycloalkyl, cycloalkenyl, cycloalkynyl and aryl as defined hereinabove. The term "substituted carbocycle" refers to carbocycle or carbocyclic groups substituted with one or more substituents, preferably 1 to 4 substituents, at any available point of attachment. Exemplary substituents include, but are not limited to, those described above for substituted cycloalkyl, substituted cycloalkenyl, substituted cycloalkynyl and substituted aryl. Exemplary substituents also include spiro-attached or fused cyclic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include spiro-attached or fused cyclic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "alkylamino" refers to a group having the structure —NHR', wherein R' is hydrogen, alkyl or substituted alkyl, cycloalkyl or substituted cycloalkyl, as defined herein. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each independently alkyl or substituted alkyl, cycloalkyl or substituted cycloalkyl, cycloalkenyl or substituted cycloalkenyl, aryl or substituted aryl, heterocyclyl or substituted heterocyclyl, as defined herein. R and R' may be the same or different in an dialkylamino moiety. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

The terms "halogen" or "halo" refer to chlorine, bromine, fluorine or iodine.

Unless otherwise indicated, any heteroatom with unsatisfied valences is assumed to have hydrogen atoms sufficient to satisfy the valences.

The compounds of the present invention may form salts which are also within the scope of this invention. Reference to a compound of the present invention is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound I with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the invention are also contemplated herein. The term "prodrug" as employed herein denotes a compound that, upon administration to a subject, undergoes chemical conversion by metabolic or chemical processes to yield a compound of the present invention, or a salt and/or solvate thereof. Solvates of the compounds of the present invention include, for example, hydrates.

Compounds of the present invention, and salts or solvates thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 90%, for example, equal to greater than 95%, equal to or greater than 99% of the compounds ("substantially pure" compounds), which is then used or formulated as described herein. Such "substantially pure" compounds of the present invention are also contemplated herein as part of the present invention.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

Definitions of specific functional groups and chemical terms are described in more detail below. For purposes of this invention, the chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

The present invention also includes isotopically labeled compounds, which are identical to the compounds disclosed herein, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, and fluorine and chlorine, such as $^2$H, $^3$H, $^{13}$C, $^{11}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, or an enantiomer, diastereomer, tautomer, or pharmaceutically acceptable salt or solvate thereof, which contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds can generally be prepared by carrying out the procedures disclosed in the Schemes and/or in the Examples below, by substituting a readily available isotopically labeled reagent for a non-isotopically labeled reagent.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

As used herein, the term "adaptive immune response" refers to any type of antigen-specific immune response. Adaptive immune responses, which are also known in the art as specific immune responses, involve lymphocytes are also characterized by immunological memory, whereby response to a second or subsequent exposure to antigen is more vigorous than the response to a first exposure to the antigen. The term adaptive immune response encompasses both humoral (antibody) immunity and cell-mediated (cellular) immunity.

As used herein, "allergy" refers to acquired hypersensitivity to a substance (allergen). Allergic conditions include eczema, allergic rhinitis or coryza, hay fever, asthma, urticaria (hives) and food allergies, and other atopic conditions.

As used herein, the term "antigenic substance" refers to any substance that induces an adaptive (specific) immune response. An antigen typically is any substance that can be specifically bound by a T-cell antigen receptor, antibody, or B-cell antigen receptor. Antigenic substances include, without limitation, peptides, proteins, carbohydrates, lipids, phospholipids, nucleic acids, autacoids, and hormones. Antigenic substances further specifically include antigens that are classified as allergens, cancer antigens, and microbial antigens.

As used herein, "asthma" refers to a disorder of the respiratory system characterized by inflammation, narrowing of the airways and increased reactivity of the airways to inhaled agents. Asthma is frequently, although not exclusively associated with atopic or allergic symptoms. For example, asthma can be precipitated by exposure to an allergen, exposure to cold air, respiratory infection, and exertion.

As used herein, the terms "autoimmune disease" and, equivalently, "autoimmune disorder" and "autoimmunity", refer to immunologically mediated acute or chronic injury to a tissue or organ derived from the host. The terms encompass both cellular and antibody—mediated autoimmune phenomena, as well as organ-specific and organ-nonspecific autoimmunity. Autoimmune diseases include insulin-dependent diabetes mellitus, rheumatoid arthritis, systemic lupus erythematosus, multiple sclerosis, atherosclerosis, psoriasis and inflammatory bowel disease. Autoimmune diseases also include, without limitation, ankylosing spondylitis, autoimmune hemolytic anemia, Behcet's syndrome, Goodpasture's syndrome, Graves' disease, Guillain-Barre syndrome, Hashimoto's thyroiditis, idiopathic thrombocytopenia, myasthenia gravis, pernicious anemia, polyarteritis nodosa, polymyositis/dermatomyositis, primary biliary sclerosis, sarcoidosis, sclerosing cholangitis, Sjogren's syndrome, systemic sclerosis (scleroderma and CREST syndrome), Takayasu's arteritis, temporal arteritis, Wegener's granulomatosis, antiphospholipid syndrome and autoimmune associated cardiovascular disease. Autoimmune diseases also include certain immune complex-associated diseases.

As used herein, the terms "cancer" and, equivalently, "tumor" refer to a condition in which abnormally replicating cells of host origin are present in a detectable amount in a subject. The cancer can be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric (stomach) cancer; intraepithelial neoplasms; leukemias; lymphomas; liver cancer; lung cancer (e.g., small cell and non-small cell); melanoma; neuroblastomas; oral cancer; ovarian cancer; pancreatic cancer; prostate cancer; rectal cancer; renal (kidney) cancer; sarcomas; skin cancer; testicular cancer; thyroid cancer; as well as other carcinomas and sarcomas. Cancers can be primary or metastatic.

As used herein, the term "CpG DNA" refers to an immunostimulatory nucleic acid which contains a cytosine-guanine (CG) dinucleotide, the C residue of which is unmethylated. The effects of CpG nucleic acids on immune modulation have been described extensively in U.S. patents such as U.S. Pat. Nos. 6,194,388; 6,207,646; 6,239,116; and 6,218,371, and published international patent applications, such as WO98/37919, WO98/40100, WO98/52581, and WO99/56755. The entire contents of each of these patents and published patent applications is hereby incorporated by reference. The entire immunostimulatory nucleic acid can be unmethylated or portions may be unmethylated but at least the C of the 5'-CG-3' must be unmethylated.

In one embodiment the CpG DNA is a CpG ODN that has a base sequence provided by 5'-TCGTCGTTTT-GTCGTTTTGTCGTT-3' (ODN 2006; SEQ ID NO: 1). CpG ODN have been further classified by structure and function into at least the following three classes or types, all of which are intended to be encompassed within the term CpG DNA as used herein: B-class CpG ODN such as ODN 2006 include the originally described immunostimulatory CpG ODN and characteristically activate B cells and NK cells but do not induce or only weakly induce expression of type I interferon (e.g., IFN-a). A-class CpG ODN, described in published PCT international application WO 01/22990, incorporate a CpG motif, include a chimeric phosphodiester/phosphorothioate backbone, and characteristically activate NK cells and induce plasmacytoid dendritic cells to express large amounts of IFN-a but do not activate or only weakly activate B cells. An example of an A-class CpG ODN is 5'-G*G*GGGACGATCGTCG*G*G*G*G-3' (ODN 2216, SEQ ID NO: 2), wherein "*" represents phosphorothioate and wherein a lack of "*" represents phosphodiester. C-class CpG ODN incorporate a CpG, include a wholly phosphorothioate backbone, include a GC-rich palindromic or nearly-palindromic region, and are capable of both activating B cells and inducing expression of IFN-a. C-class CpG ODN have been described, for example, in published U.S. patent application 2003/0148976. An example of a C-class CpG ODN is 5'-TCGTCGTTTTCG-GCGCGCGCCG-3' (ODN 2395; SEQ ID NO: 3). For a review of the various classes of CpG ODN, see also Vollmer J. et al. (2004) Eur. J. Immunol. 34: 251-62.

As used herein, "cytokine" refers to any of a number of soluble proteins or glycoproteins that act on immune cells through specific receptors to affect the state of activation and function of the immune cells. Cytokines include interferons, interleukins, tumor necrosis factor, transforming growth factor beta, colony-stimulating factors (CSFs), chemokines, as well as others. Various cytokines affect innate immunity, acquired immunity, or both. Cytokines specifically include, without limitation, IFN-a, IFN-p, IFN-y, IL-1, IL-2, IL-3, IL-4, IL-5, IL-6, IL-9, IL-10, IL-12, IL-13, IL-18, TNF-a, TGF-β, granulocyte colony-stimulating factor (G-CSF), and granulocyte-macrophage colony-stimulating factor (GM-CSF). Chemokines specifically include, without limitation, IL-8, IP-10, I-TAC, RANTES, MIP-1a, MIP-1p, Gro-a, Gro-, Gro-y, MCP-1, MCP-2, and MCP-3.

Most mature CD4+ T helper cells can be categorized into one of two cytokine-associated, cross-regulatory subsets or phenotypes: Th1 or Th2. Th1 cells are associated with IL-2, IL-3, IFN, GM-CSF and high levels of TNF-a. Th2 cells are associated with IL-3, IL-4, IL-5, IL-6, IL-9, IL-10, IL-13, GM-CSF and low levels of TNF-a. The Th1 subset promotes both cell-mediated immunity and humoral immunity that is characterized by immunoglobulin class switching to IgG2a in mice. Th1 responses can also be associated with delayed-type hypersensitivity and autoimmune disease. The Th2 subset induces primarily humoral immunity and induces immunoglobulin class switching to IgE and IgGl in mice. The antibody isotypes associated with Th1 responses generally have good neutralizing and opsonizing capabilities, whereas those associated with Th2 responses are associated more with allergic responses.

Several factors have been shown to influence commitment to Th1 or Th2 profiles. The best characterized regulators are cytokines IL-12 and IFN-y are positive Th1 and negative Th2 regulators. IL-12 promotes IFN-y production, and IFN-y provides positive feedback for IL-12. IL-4 and IL-10 appear to be required for the establishment of the Th2 cytokine profile and to down-regulate Th1 cytokine production; the effects of IL-4 are in some cases dominant over those of IL-12. IL-13 was shown to inhibit expression of inflammatory cytokines, including IL-12 and TNF-a by LPS-induced monocytes, in a way similar to IL-4.

As used herein, "effective amount" refers to any amount that is necessary or sufficient for achieving or promoting a desired outcome. In some instances an effective amount is a therapeutically effective amount. A therapeutically effective amount is any amount that is necessary or sufficient for promoting or achieving a desired biological response in a subject. The effective amount for any particular application can vary depending on such factors as the disease or condition being treated, the particular agent being administered, the size of the subject, or the severity of the disease or condition. One of ordinary skill in the art can empirically determine the effective amount of a particular agent without necessitating undue experimentation.

As used herein, "graft rejection" refers to immunologically mediated hyperacute, acute, or chronic injury to a tissue or organ derived from a source other than the host. The term thus encompasses both cellular and antibody-mediated rejection, as well as rejection of both allografts and xenografts.

As used herein, the term "immune cell" refers to a cell belonging to the immune system. Immune cells include T lymphocytes (T cells), B lymphocytes (B cells), natural killer (NK) cells, granulocytes, neutrophils, macrophages, monocytes, dendritic cells, and specialized forms of any of the foregoing, e.g., plasmacytoid dendritic cells, plasma cells, NKT, T helper, and cytotoxic T lymphocytes (CTL).

As used herein, the term "immune complex" refers to any conjugate including an antibody and an antigen specifically bound by the antibody. In one embodiment, the antigen is an autoantigen.

As used herein, the term "immune complex comprising a nucleic acid" refers to any conjugate including an antibody and a nucleic acid-containing antigen specifically bound by the antibody. The nucleic acid-containing antigen can include chromatin, ribosomes, small nuclear proteins, histones, nucleosomes, DNA, RNA, or any combination thereof. The antibody can but need not necessarily bind specifically to a nucleic acid component of the nucleic acid-containing antigen. In some embodiments, the term "immune complex comprising a nucleic acid" refers also to non-antibody complexes such as HMGB1, nucleic acids LL-37, and other nucleic acid binding proteins such as histones, transcription factors and enzymes.

As used herein, the term "immune complex-associated disease" refers to any disease characterized by the production and/or tissue deposition of immune complexes, including, but not limited to systemic lupus erythematosus (SLE) and related connective tissue diseases, rheumatoid arthritis, hepatitis C- and hepatitis B-related immune complex disease (e.g., cryoglobulinemia), Beget's syndrome, autoimmune glomerulonephritides, and vasculopathy associated with the presence of LDL/anti-LDL immune complexes.

As used herein, "immunodeficiency" refers to a disease or disorder in which the subject's immune system is not functioning in normal capacity or in which it would be useful to boost a subject's immune response for example to eliminate a tumor or cancer (e.g., tumors of the brain, lung (e.g., small cell and non-small cell), ovary, breast, prostate, colon, as well as other carcinomas and sarcomas) or an infection in a subject. The immunodeficiency can be acquired or it can be congenital.

As used herein, "immunostimulatory nucleic acid-associated response in a subject" refers to a measurable response in a subject associated with administration to the subject of an immunostimulatory nucleic acid. Such responses include, without limitation, elaboration of cytokines, chemokines, growth factors, or immunoglobulin; expression of immune cell surface activation markers; Th1/Th2 skewing; and clinical disease activity.

As used herein, the terms "infection" and, equivalently, "infectious disease" refer to a condition in which an infectious organism or agent is present in a detectable amount in the blood or in a normally sterile tissue or normally sterile compartment of a subject. Infectious organisms and agents include viruses, bacteria, fungi, and parasites. The terms encompass both acute and chronic infections, as well as sepsis.

As used herein, the term "innate immune response" refers to any type of immune response to certain pathogen-associated molecular patterns (PAMPs). Innate immunity, which is also known in the art as natural or native immunity, involves principally neutrophils, granulocytes, mononuclear phagocytes, dendritic cells, NKT cells, and NK cells. Innate <BR> <BR> immune responses can include, without limitation, type I interferon production (e.g., IFN-a), neutrophil activation, macrophage activation, phagocytosis, opsonization, complement activation, and any combination thereof.

As used herein, the term "self-DNA" refers to any DNA derived from the genome of a host subject. In one embodiment, self-DNA includes complementary DNA (cDNA) derived from a host subject. Self-DNA includes intact and degraded DNA.

As used herein, the term "self-RNA" refers to any RNA derived from the genome of a host subject. In one embodiment self-RNA is a messenger RNA (mRNA) derived from a host subject. In another embodiment self-RNA is a regulatory RNA such as micro RNAs. In one embodiment self-RNA includes ribosomal RNA (rRNA) derived from a host subject. Self-RNA includes intact and degraded RNA.

As used herein, the term "subject" refers to a vertebrate animal. In one embodiment the subject is a mammal. In one embodiment the subject is a human. In other embodiments the subject is a non-human vertebrate animal, including, without limitation, non-human primates, laboratory animals, livestock, domesticated animals, and non-domesticated animals.

As used herein, "subject having or at risk of developing TLR-mediated immunostimulation" refers to a subject exposed to or at risk of exposure to a PAMP or other TLR ligand.

As used herein, the terms "Toll-like receptor" and, equivalently, "TLR" refer to any member of a family of at least ten highly conserved mammalian pattern recognition receptor proteins (TLR1-TLR10) which recognize pathogen-associated molecular patterns (PAMPs) and act as key signaling elements in innate immunity. TLR polypeptides share a characteristic structure that includes an extracellular (extracytoplasmic) domain that has leucine-rich repeats, a transmembrane domain, and an intracellular (cytoplasmic) domain that is involved in TLR signaling. TLRs include but are not limited to human TLRs.

Nucleic acid and amino acid sequences for all ten currently known human TLRs are available from public databases such as GenBank. Similarly, nucleic acid and amino acid sequences for various TLRs from numerous non-human species are also available from public databases including GenBank. For example, nucleic acid and amino acid sequences for human TLR9 (hTLR9) can be found as GenBank accession numbers AF245704 (coding region spanning nucleotides 145-3243) and AAF78037, respectively. Nucleic acid and amino acid sequences for murine TLR9 (mTLR9) can be found as GenBank accession numbers AF348140 (coding region spanning nucleotides 40-3138) and AAK29625, respectively. The deduced human TLR9 protein contains 1,032 amino acids and shares an overall amino acid identity of 75.5% with mouse TLR9. Like other TLR proteins, human TLR9 contains extracellular leucine-rich repeats (LRRs) and a cytoplasmic Toll/interleukin-1R (TIR) domain. It also has a signal peptide (residues 1-25) and a transmembrane domain (residues 819-836).

Nucleic acid and amino acid sequences for human TLR8 (hTLR8) can be found as GenBank accession numbers AF245703 (coding region spanning nucleotides 49-3174) and AAF78036, respectively. Nucleic acid and amino acid sequences for murine TLR8 (mTLR8) can be found as GenBank accession numbers AY035890 (coding region spanning nucleotides 59-3157) and AAK62677, respectively.

Nucleic acid and amino acid sequences for human TLR7 (hTLR7) can be found as GenBank accession numbers AF240467 (coding region spanning nucleotides 135-3285) and AAF60188, respectively. Nucleic acid and amino acid sequences for murine TLR7 (mTLR7) can be found as GenBank accession numbers AY035889 (coding region spanning nucleotides 49-3201) and AAK62676, respectively.

Nucleic acid and amino acid sequences for human TLR3 (hTLR3) can be found as GenBank accession numbers NM003265 (coding region spanning nucleotides 102-2816) and NP003256, respectively. Nucleic acid and amino acid sequences for murine TLR3 (hTLR3) can be found as GenBank accession numbers AF355152 (coding region spanning nucleotides 44-2761) and AAK26117, respectively.

While hTLR1 is ubiquitously expressed, hTLR2, hTLR4 and hTLR5 are present in monocytes, polymorphonuclear phagocytes, and dendritic cells. Muzio M., et al. (2000) J. Leukoc. Biol. 67: 450-6. Recent publications reported that hTLR1, hTLR6, hTLR7, hTLR9 and hTLR10 are present in human B cells. Human TLR7 and hTLR9 are present in plasmacytoid dendritic cells (pDCs), while myeloid dendritic cells express hTLR7 and hTLR8 but not hTLR9. Human TLR8, however, appears not to be expressed in pDCs.

As members of the pro-inflammatory interleukin-1 receptor (IL-1R) family, TLRs share homologies in their cytoplasmic domains called Toll/IL-1R homology (TIR) domains. See PCT published applications PCT/US98/08979 and PCT/US01/16766. Intracellular signaling mechanisms mediated by TLRs appear generally similar, with MyD88 and tumor necrosis factor receptor-associated factor 6 (TRAF6) believed to have critical roles. Wesche H., et al. (1997) Immunity 7: 837-47; Medzhitov R., et al. (1998) Mol Cell 2: 253-8; Adachi O., et al. (1998) Immunity 9: 143-50; Kawai T., et al. (1999) Immunity 11: 115-22); Cao Z., et al. (1996) Nature 383: 443-6; Lomaga M. A., et al. (1999) Genes Dev 13: 1015-24. Signal transduction between MyD88 and TRAF6 is known to involve members of the serine-threonine kinase IL-1 receptor-associated kinase (IRAK) family, including at least IRAK-1 and IRAK-2. Muzio M., et al. (1997) Science 278: 1612-5.

Briefly, MyD88 is believed to act as an adapter molecule between the TIR domain of a TLR or IL-1R and IRAK (which includes at least any one of IRAK-1, IRAK-2, IRAK-4, and IRAK-M). MyD88 includes a C-terminal Toll homology domain and an N-terminal death domain. The Toll homology domain of MyD88 binds the TIR domain of TLR or IL-1R, and the death domain of MyD88 binds the death domain of the serine kinase IRAK. IRAK interacts with TRAF6, which acts as an entryway into at least two pathways, one leading to activation of the transcription factor NF-KB and another leading to activation of Jun and Fos, members of the activator protein-1 (AP-1) transcription factor family. Activation of NF-KB involves the activation of TAK-1, a member of the MAP 3 kinase (MAPK) family, and IKB kinases. The IoB kinases phosphorylate IKB, leading to its—degradation and the translocation of NF-KB to the nucleus. Activation of Jun and Fos is believed to involve MAP kinase kinases (MAPKKs) and MAP kinases ERK, p38, and JNK/SAPK. Both NF-KB and AP-1 are involved in controlling the transcription of a number of key immune response genes, including genes for various cytokines and costimulatory molecules. See Aderem A., et al. (2000) Nature 406: 782-7; Hacker H., et al. (1999) EMBO J 18: 6973-82.

As used herein, the terms "TLR ligand" and, equivalently, "ligand for a TLR" and "TLR signaling agonist", refer to a molecule, other than a small molecule according to Formula I described herein that interacts, directly or indirectly, with a TLR through a TLR domain other than a TIR domain and induces TLR-mediated signaling. In one embodiment a TLR ligand is a natural ligand, i.e., a TLR ligand that is found in nature. In one embodiment a TLR ligand refers to a molecule other than a natural ligand of a TLR, e.g., a molecule prepared by human activity. In one embodiment the TLR is TLR9 and the TLR signal agonist is a CpG nucleic acid.

Ligands for many but not all of the TLRs have been described. For instance, it has been reported that TLR2 signals in response to peptidoglycan and lipopeptides. Yoshimura A., et al. (1999) J. Immunol. 163: 1-5; Brightbill H. D., et al. (1999) Science 285: 732-6; Aliprantis A. O., et al. (1999) Science 285: 736-9; Takeuchi O., et al. (1999) Immunity 11: 443-51; Underhill D. M., et al. (1999) Nature 401: 811-5. TLR4 has been reported to signal in response to lipopolysaccharide (LPS). See Hoshino K., et al. (1999) Immunol. 162: 3749-52; Poltorak A., et al. (1998) Science 282: 2085-8; Medzhitov R., et al. (1997) Nature 388: 394-7. Bacterial flagellin has been reported to be a natural ligand for TLR5. See Hayashi F., et al. (2001) Nature 410: 1099-1103. TLR6, in conjunction with TLR2, has been reported to signal in response to proteoglycan. See Ozinsky A., et al. (2000) Proc. Natl. Acad. Sci. USA 97: 13766-71; Takeuchi O., et al. (2001) Int. Immunol. 13: 933-40.

Recently it was reported that TLR9 is a receptor for CpG DNA. Hemmi H., et al. (2000) Nature 408: 740-5; Bauer S., et al. (2001) Proc. Natl. Acad. Sci. USA 98: 9237-42. CpG DNA, which includes bacterial DNA and synthetic DNA with CG dinucleotides in which cytosin is unmethylated, is described in greater detail elsewhere herein. Marshak-Rothstein and colleagues also recently reported their finding that TLR9 signaling can occur in certain autoimmune diseases in response to immune complexes containing IgG and chromatin. Leadbetter E. A., et al. (2002) Nature 416: 595-8. Thus, in a broader sense it appears that TLR9 can signal in response to self or non-self nucleic acid, either DNA or RNA, when the nucleic acid is presented in a suitable context, e.g., as part of an immune complex.

Recently it was reported that certain imidazoquinoline compounds having antiviral activity are ligands of TLR7 and TLR8. Hemmi H., et al. (2002) Nat. Immunol. 3: 196-200; Jurk M., et al. (2002) Nat. Immunol. 3: 499. Imidazoquinolines are potent synthetic activators of immune cells with antiviral and antitumor properties. Using macrophages from wildtype and MyD88-deficient mice, Hemmi, et al. recently reported that two imidazoquinolines, imiquimod and resiquimod (R848), induce tumor necrosis factor (TNF) and interleukin-12 (IL-12) and activate NF-KB only in wildtype cells, consistent with activation through a TLR. Hemmi H., et al. (2002) Nat. Immunol. 3: 196-200. Macrophages from mice deficient in TLR7 but not other TLRs produced no detectable cytokines in response to these imidazoquinolines. In addition, the imidazoquinolines induced dose-dependent proliferation of splenic B cells and the activation of intracellular signaling cascades in cells from wildtype but not TLR7-/- mice. Luciferase analysis established that expression of human TLR7, but not TLR2 or TLR4, in human embryonic kidney cells results in NF-KB activation in response to resiquimod. The findings of Hemmi, et al. thus suggested that these imidazoquinoline compounds are non-natural ligands of TLR7 that can induce signaling through TLR7. Recently it was reported that R848 is also a ligand for human TLR8. See Jurk M., et al. (2002) Nat. Immunol. 3:499. It has also been reported that ssRNA is a natural ligand and that aberrant stimulation of TLR7 and or TLR8 by RNA complexes is involved in autoimmunity.

It was recently reported that ligands of TLR3 include poly (I: C) and double-stranded RNA (dsRNA). For purposes of this invention, poly (I: C) and double-stranded RNA (dsRNA) are classified as oligonucleotide molecules. By stimulating kidney cells expressing one of a range of TLRs with poly (I: C), Alexopoulou, et al. reported that only cells expressing TLR3 respond by activating NF-aB. See Alexopoulou L., et al. (2001) Nature 413: 732-8.

Alexopoulou, et al. also reported that wildtype cells stimulated with poly (I: C) activate NF-KB and produce inflammatory cytokines IL-6, IL-12, and TNF-a, whereas the corresponding responses of TLR3-/- cells were significantly impaired. In contrast, TLR3-/- cells responded equivalently to wildtype cells in response to lipopolysaccharide, peptidoglycan, and CpG dinucleotides. Analysis of MyD88-/- cells indicated that this adaptor protein is involved in dsRNA-induced production of cytokines and proliferative responses, although activation of NF-KB and MAP kinases are not affected, indicating distinct pathways for these cellular responses. Alexopoulou et al. proposed that TLR3 may have a role in host defense against viruses.

As used herein, a "cell expressing a TLR" refers to any cell which expresses, either naturally or artificially, a functional TLR. A functional TLR is a full-length TLR protein or a fragment thereof capable of inducing a signal in response to interaction with its ligand.

Generally, the functional TLR will include at least a TLR ligand-binding fragment of the extracellular domain of the full-length TLR and at least a fragment of a TIR domain capable of interacting with another Toll homology domain-containing polypeptide, e.g., MyD88. In various embodiments the functional TLR is a full-length TLR selected from TLR1, TLR2, TLR3, TLR4, TLR5, TLR6, TLR7, TLR8, TLR9, and TLR10.

Compounds

In one aspect, novel imidazoquinoline compounds as immune system modulators are described. The agonist imidazoquinoline having similar substituents to those of chloroquine, quinazoline, and quinacrine, and the imidazoquinoline compounds as disclosed herein are useful in methods for inhibiting an immune response, both in vitro and in vivo, including methods for treating immune complex associated diseases and autoimmune disorders. Without being bound to any theory or mechanism, it is believed that the small molecules described by the present invention affect immune stimulation via interaction with a TLR. More particularly, it is believed that many of the small molecules described by the present invention inhibit immune stimulation via TLR antagonism. In particular, it is believed that many of the small molecules described by the present invention inhibit immune stimulation via TLR 9,8,7,3 antagonism.

In another aspect, the invention provides novel imidazoquinoline compositions. As described further below, these compositions and other imidazoquinoline compositions are useful in methods for inhibiting an immune response, both in vitro and in vivo, including methods for treating immune complex associated diseases and autoimmune disorders. It is also believed that the novel imidazoquinoline compositions as described herein can be used for prevention and treatment of malaria, as well as for treatment of other diseases.

In one aspect, a compound of Formula I, or a pharmaceutically acceptable salt thereof is described:

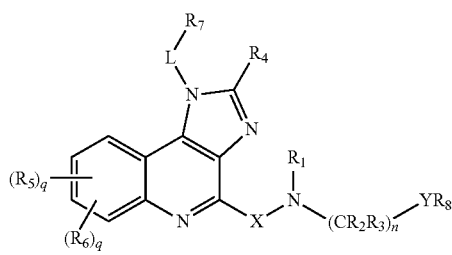

(I)

wherein

X is absent or is an alkyl, cycloalkyl, aryl, aralkyl, or heterocycle;

each occurrence of $R_1$ is independently hydrogen, alkyl, cycloalkyl, alkenyl, cycloalkenyl, alkynyl, heterocycle, or aryl;

each occurrence of $R_2$ and $R_3$ is independently hydrogen, alkyl, cycloalkyl, OH, alkoxy, —$(CH_2)_p NR_a R_b$, or $R_2$ and $R_3$ together with the carbon atom to which they are bonded optionally form a $(C_3$-$C_7)$cycloalkyl;

n is an integer of 2-4;

each q is an integer of 1-2;

Y is $NR_9$ or O;

$R_8$ is hydrogen, alkyl, cycloalkyl, monocyclic heterocycle, or aryl;

$R_9$ is H, Me, Et, n-Pr, i-Pr, n-Bu, i-Bu, t-Bu, $CH_2CMe_3$, Ph, $CH_2Ph$, C(=O)$R_{12}$, $(CH_2)_p OR_a$, and $(CH_2)_p NR_b R_c$, wherein $R_{12}$ is alkyl, phenyl, or heterocycle; $R_a$, $R_b$ and $R_c$ are each independently hydrogen, or $(C_1$-$C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a heterocycle comprising 1-4 heteroatoms, wherein the heterocycle is optionally substituted by $(C_1$-$C_4)$alkyl;

or $R_1$ and $R_8$ optionally form a heterocycle comprising 2-4 heteroatoms, wherein the heterocycle is optionally substituted by $(C_1$-$C_4)$alkyl;

$R_4$ is hydrogen, halogen, cyano, nitro, $CF_3$, $OCF_3$, alkyl, cycloalkyl, alkenyl, aryl, heterocycle, $OR_a$, —$CH_2OR_a$, $SR_a$, S(=O)$R_a$, S(=O)$_2R_a$, $NR_bR_c$, S(=O)$_2NR_bR_c$, C(=O)$OR_a$, C(=O)$R_a$, C(=O)$NR_bR_c$, OC(=O)$R_a$, OC(=O)$NR_bR_c$, $NR_bC(=O)OR_a$, $NR_bC(=O)R_a$;

$R_5$ and $R_6$ are each independently hydrogen, halogen, cyano, nitro, $CF_3$, $OCF_3$, alkyl, cycloalkyl, alkenyl, aryl, heterocycle, $OR_a$, $SR_a$, S(=O)$R_a$, S(=O)$_2R_a$, $NR_bR_c$, S(=O)$_2NR_bR_c$, C(=O)$OR_a$, C(=O)$R_a$, C(=O)$NR_bR_c$, OC(=O)$R_a$, OC(=O)$NR_bR_c$, $NR_bC(=O)OR_a$, $NR_bC$(=O)$R_a$, alkaryl, alkylheterocyclic, or $NR_b(CH_2)_pNR_bR_c$; or said $R_5$ and $R_6$ together with the carbon atoms to which they are bonded optionally form a heterocycle comprising 1-4 heteroatoms, wherein the heterocycle is optionally substituted by $(C_1$-$C_4)$alkyl;

L is absent or is alkyl or alkenyl containing from 2 to 10 carbon atoms;

$R_7$ is H, alkyl, heteroaryl, —$O(CH_2)_p OR_a$, or $NR_{10}R_{11}$, wherein the heteroaryl are optionally substituted by $(C_1$-$C_4)$ alkyl;

$R_{10}$ and $R_{11}$ are each independently hydrogen, alkyl, cycloalkyl, alkenyl, aryl or alkylaryl, or $R_{10}$ and $R_{11}$ together with the nitrogen atom to which they are bonded form a heterocycle;

p is an integer of 0, 1, 2, 3, 4, 5, or 6;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$, together with the nitrogen atom to which they are bonded optionally form a heterocycle comprising 1-4 heteroatoms, wherein the heterocycle is optionally substituted by $(C_1$-$C_4)$ alkyl.

In some embodiments, X is absent. In other embodiments, X is alkyl. In yet other embodiments, X is cycloalkyl. In yet other embodiments, X is heterocycle. In yet other embodiments, X is aralkyl. In yet other embodiments, X is -phenyl-$(CH_2)$—.

In any of the preceding embodiments, L is alkyl or alkenyl containing from 2 to 4 carbon atoms.

In other embodiments, the compound of Formula (I) has the structure of Formula (II):

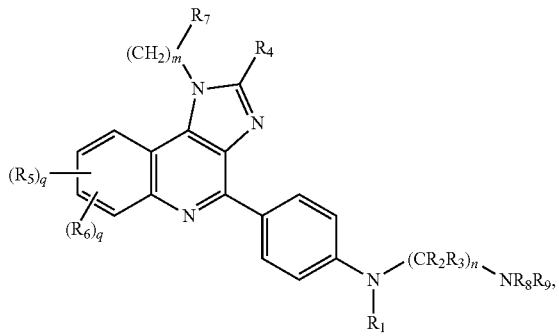

(II)

wherein each occurrence of $R_1$ is independently hydrogen, $(C_1$-$C_4)$alkyl, $(C_3$-$C_7)$cycloalkyl, $(C_2$-$C_6)$alkenyl, $(C_2$-$C_6)$alkynyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

each occurrence of $R_2$ and $R_3$ is independently hydrogen, $(C_1$-$C_4)$alkyl, $(C_3$-$C_7)$cycloalkyl, OH, $(C_1$-$C_4)$alkoxy, —$(CH_2)_p NR_a R_b$, or $R_2$ and $R_3$ together with the carbon atom to which they are bonded optionally form a $(C_3$-$C_6)$ cycloalkyl;

$R_8$ is hydrogen, $(C_1$-$C_4)$alkyl, $(C_3$-$C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

$R_9$ is H, Me, Et, n-Pr, i-Pr, n-Bu, i-Bu, t-Bu, $CH_2CMe_3$, Ph, $CH_2Ph$, C(=O)$R_{12}$, $(CH_2)_p OR_a$, and $(CH_2)_p NR_b R_c$, wherein $R_{12}$ is $(C_1$-$C_4)$alkyl, phenyl, or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; $R_a$, $R_b$ and $R_c$ are each independently hydrogen, or $(C_1-C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a 3- to 7-membered heterocycle which may be saturated or unsaturated comprising 1-4 heteroatoms, wherein the heterocycle is optionally substituted by $(C_1-C_4)$alkyl;

or $R_1$ and $R_8$ optionally form a 5- to 7-membered heterocycle which may be saturated or unsaturated comprising 2-4 heteroatoms, wherein the heterocycle is optionally substituted by $(C_1-C_4)$alkyl;

$R_4$ is hydrogen, halogen, cyano, nitro, $CF_3$, $OCF_3$, $(C_1-C_4)$alkyl, $(C_3-C_7)$cycloalkyl, $(C_2-C_6)$alkenyl, aryl, heterocycle, $OR_a$, $-CH_2OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

$R_5$ and $R_6$ are each independently hydrogen, halogen, cyano, nitro, $CF_3$, $OCF_3$, $(C_1-C_4)$alkyl, $(C_3-C_7)$cycloalkyl, $(C_2-C_6)$alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, alkaryl, alkylheterocyclic, or $NR_b(CH_2)_pNR_bR_c$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

L is alkyl or alkenyl containing from 2 to 10 carbon atoms;

$R_7$ is H, $(C_1-C_4)$alkyl, heteroaryl, $-O(CH_2)_pOR_a$, or $NR_{10}R_{11}$, wherein the heteroaryl is a 5- to 6-membered aromatic ring which may be saturated or unsaturated containing one to three heteroatoms which may the same or different selected from nitrogen, sulfur and oxygen, and the heteroaryl is optionally substituted by $(C_1-C_4)$alkyl;

$R_{10}$ and $R_{11}$ are each independently hydrogen, $(C_1-C_4)$alkyl, $(C_3-C_7)$cycloalkyl, $(C_2-C_6)$alkenyl, aryl or $(C_1-C_4)$alkylaryl, or $R_{10}$ and $R_{11}$ together with the nitrogen atom to which they are bonded form a 3- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

m is an integer of 2-6;
n is an integer of 2-4;
each q is an integer of 1-2;
each occurrence of $R_a$ is independently hydrogen, $(C_1-C_4)$alkyl, $(C_3-C_7)$cycloalkyl, $(C_2-C_6)$alkenyl, $(C_5-C_7)$cycloalkenyl, $(C_2-C_6)$alkynyl, aryl, or a 3- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl; and each occurrence of $R_b$ and $R_c$ is independently hydrogen, $(C_1-C_4)$alkyl, $(C_3-C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl; or said $R_b$ and $R_c$ together with the nitrogen atom to which they are bonded optionally form a 3- to 7-membered heterocycle which may be saturated or unsaturated comprising 1-4 heteroatoms, wherein the heterocycle is optionally substituted by $(C_1-C_4)$alkyl.

In yet other embodiments, the compound of Formula (I) has the structure of Formula (III):

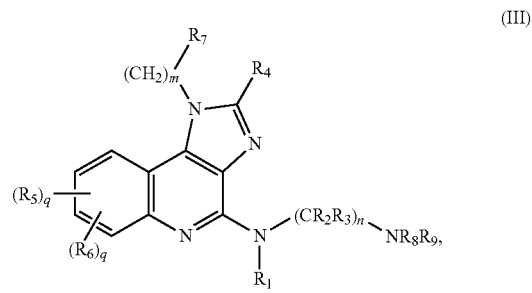

(III)

wherein
each occurrence of $R_1$ is independently hydrogen, $(C_1-C_4)$alkyl, $(C_3-C_7)$cycloalkyl, $(C_2-C_6)$alkenyl, $(C_2-C_6)$alkynyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

each occurrence of $R_2$ and $R_3$ is independently hydrogen, $(C_1-C_4)$alkyl, $(C_3-C_7)$cycloalkyl, OH, $(C_1-C_4)$alkoxy, $-(CH_2)_pNR_aR_b$, or $R_2$ and $R_3$ together with the carbon atom to which they are bonded optionally form a $(C_3-C_6)$cycloalkyl;

$R_8$ is hydrogen, $(C_1-C_4)$alkyl, $(C_3-C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

$R_9$ is H, Me, Et, n-Pr, i-Pr, n-Bu, i-Bu, t-Bu, $CH_2CMe_3$, Ph, $CH_2Ph$, $C(=O)R_{12}$, $(CH_2)_pOR_a$, and $(CH_2)_pNR_bR_c$, wherein $R_{12}$ is $(C_1-C_4)$alkyl, phenyl, or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl; $R_a$, $R_b$ and $R_c$ are each independently hydrogen, or $(C_1-C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a 3- to 7-membered heterocycle which may be saturated or unsaturated comprising 1-4 heteroatoms, wherein the heterocycle is optionally substituted by $(C_1\text{-}C_4)$alkyl;

or $R_1$ and $R_8$ optionally form a 5- to 7-membered heterocycle which may be saturated or unsaturated comprising 2-4 heteroatoms, wherein the heterocycle is optionally substituted by $(C_1\text{-}C_4)$alkyl;

$R_4$ is hydrogen, halogen, cyano, nitro, $CF_3$, $OCF_3$, $(C_1\text{-}C_4)$alkyl, $(C_3\text{-}C_7)$cycloalkyl, $(C_2\text{-}C_6)$alkenyl, aryl, heterocycle, $OR_a$, $-CH_2OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1\text{-}C_4)$alkyl, phenyl or benzyl;

$R_5$ and $R_6$ are each independently hydrogen, halogen, cyano, nitro, $CF_3$, $OCF_3$, $(C_1\text{-}C_4)$alkyl, $(C_3\text{-}C_7)$cycloalkyl, $(C_2\text{-}C_6)$alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, alkaryl, alkylheterocyclic, or $NR_b(CH_2)_pNR_bR_c$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1\text{-}C_4)$alkyl, phenyl or benzyl;

L is alkyl or alkenyl containing from 2 to 10 carbon atoms;

$R_7$ is H, $(C_1\text{-}C_4)$alkyl, heteroaryl, $-O(CH_2)_pOR_a$, or $NR_{10}R_{11}$, wherein the heteroaryl is a 5- to 6-membered aromatic ring which may be saturated or unsaturated containing one to three heteroatoms which may the same or different selected from nitrogen, sulfur and oxygen, and the heteroaryl is optionally substituted by $(C_1\text{-}C_4)$alkyl;

m is an integer of 2-6;
n is an integer of 2-4;
each q is an integer of 1-2;

$R_{10}$ and $R_{11}$ are each independently hydrogen, $(C_1\text{-}C_4)$alkyl, $(C_3\text{-}C_7)$cycloalkyl, $(C_2\text{-}C_6)$alkenyl, aryl or $(C_1\text{-}C_4)$alkylaryl, or $R_{10}$ and $R_{11}$ together with the nitrogen atom to which they are bonded form a 3- to 7-membered heterocycle which may be saturated or unsaturated containing one to three heteroatoms which may the same or different selected from nitrogen, sulfur and oxygen, in which the heterocycle is optionally substituted by $(C_1\text{-}C_4)$alkyl, phenyl or benzyl;

each occurrence of $R_a$ is independently hydrogen, $(C_1\text{-}C_4)$alkyl, $(C_3\text{-}C_7)$cycloalkyl, $(C_2\text{-}C_6)$alkenyl, $(C_5\text{-}C_7)$cycloalkenyl, $(C_2\text{-}C_6)$alkynyl, aryl, or a 3- to 7-membered heterocycle which may be saturated or unsaturated containing one to three heteroatoms which may the same or different selected from nitrogen, sulfur and oxygen, in which the heterocycle is optionally substituted by $(C_1\text{-}C_4)$alkyl, phenyl or benzyl; and each occurrence of $R_b$ and $R_c$ is independently hydrogen, $(C_1\text{-}C_4)$alkyl, $(C_3\text{-}C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1\text{-}C_4)$alkyl, phenyl or benzyl; or said $R_b$ and $R_c$ together with the nitrogen atom to which they are bonded optionally form a 3- to 7-membered heterocycle which may be saturated or unsaturated comprising 1-4 heteroatoms, wherein the heterocycle is optionally substituted by $(C_1\text{-}C_4)$alkyl.

In some embodiments, $R_7$ is $NR_{10}R_{11}$, in which $R_{10}$ and $R_{11}$ are each independently hydrogen, $(C_1\text{-}C_4)$alkyl, or $(C_1\text{-}C_4)$alkylaryl.

In some embodiments, $R_7$ is $NR_{10}R_{11}$, in which $R_{10}$ and $R_{11}$ together with the nitrogen atom to which they are bonded form a 3- to 7-membered heterocycle which may be saturated or unsaturated containing one to three heteroatoms which may the same or different selected from nitrogen, sulfur and oxygen, in which the heterocycle is optionally substituted by $(C_1\text{-}C_4)$alkyl, phenyl or benzyl.

In some embodiments, $NR_{10}R_{11}$ and $NR_8R_9$ are each independently a heterocycle selected from

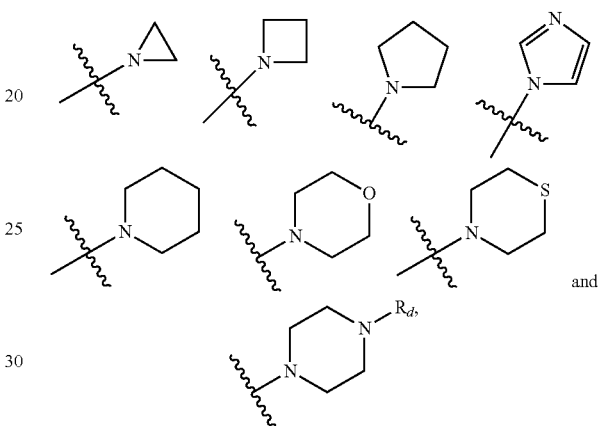

in which $R_d$ is H, Me, Et, n-Pr, i-Pr, n-Bu, i-Bu, t-Bu, $CH_2CMe_3$, Ph, $CH_2Ph$, $C(=O)R_{12}$, $(CH_2)_pOR_a$, and $(CH_2)_pNR_bR_c$, wherein $R_{12}$ is alkyl, phenyl, or heterocycle; $R_a$, $R_b$ and $R_c$ are each independently hydrogen, or $(C_1\text{-}C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4.

In some embodiments, $NR_{10}R_{11}$ and $NR_8R_9$ are each independently a heterocycle selected from

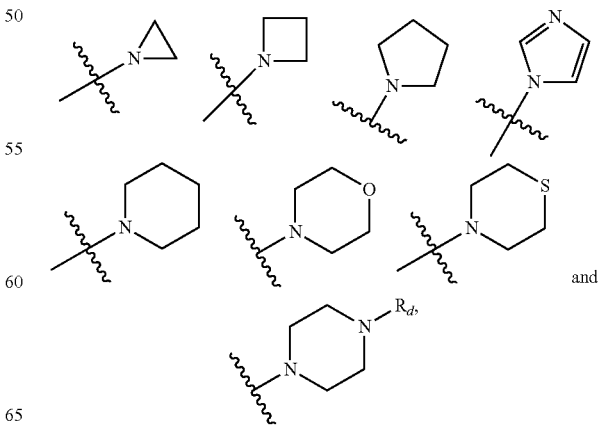

in which $R_d$ is H, Me, Et, n-Pr, i-Pr, n-Bu, i-Bu, t-Bu, CH$_2$CMe$_3$, Ph, or CH$_2$Ph.

In some embodiments, $R_1$ and $R_8$ together form a heterocycle comprising 2-4 heteroatoms, wherein the heterocycle is optionally substituted by (C$_1$-C$_4$)alkyl.

In some embodiments, $R_1$ and $R_8$ together form

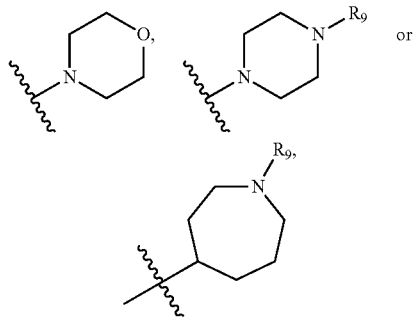

in which $R_9$ is H, Me, Et, n-Pr, i-Pr, n-Bu, i-Bu, t-Bu, CH$_2$CMe$_3$, Ph, CH$_2$Ph, C(=O)R$_{12}$, (CH$_2$)$_p$OR$_a$, and (CH$_2$)$_p$NR$_b$R$_c$, wherein R$_{12}$ is alkyl, phenyl, or heterocycle; R$_a$, R$_b$ and R$_c$ are each independently hydrogen, or (C$_1$-C$_4$)alkyl, or R$_b$ and R$_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4.

In some embodiments, $R_d$ is H, Me, Et, n-Pr, i-Pr, n-Bu, i-Bu, t-Bu, CH$_2$CMe$_3$, Ph, or CH$_2$Ph.

In some embodiments, $R_1$ is H. In some embodiments, $R_2$ and $R_3$ are each independently H. In some embodiments, the compound is selected from Tables 1-2.

In one aspect, the present invention provides a compound selected from Compound Nos 1 through 70 as described in Tables 1 and 2. The enumerated compounds in Tables 1 and 2 are representative and non-limiting imidazopyridine compounds of Formula (I) the invention.

TABLE 1

Selected imidazoquinoline compositions.

| Compound No. | X | $R_1$-N-(CR$_2$R$_3$)$_n$-YR$_8$ | L | $R_7$ | $R_4$ | $R_5$, $R_6$ |
|---|---|---|---|---|---|---|
| 1 | absent | N-methylpiperazinyl (N-CH$_3$) | —(CH$_2$)$_2$— | morpholinyl (N-substituted) | H | H, H |
| 2 | absent | N-methylpiperazinyl (N-CH$_3$) | —(CH$_2$)$_2$— | morpholinyl (N-substituted) | H | H, H |
| 3 | absent | N-methylpiperazinyl (N-CH$_3$) | —(CH$_2$)$_2$— | morpholinyl (N-substituted) | CH$_2$OEt | H, H |
| 4 | p-tolyl | N-methylpiperazinyl (N-CH$_3$) | —(CH$_2$)$_2$— | N(CH$_3$)$_2$ | CH$_3$ | H, H |
| 5 | p-tolyl | N-methylpiperazinyl (N-CH$_3$) | —(CH$_2$)$_2$— | N(CH$_3$)$_2$ | CH$_2$OEt | H, H |
| 6 | p-tolyl | N-methylpiperazinyl (N-CH$_3$) | —(CH$_2$)$_2$— | N(CH$_3$)$_2$ | phenyl | CH$_3$, CH$_3$ |

TABLE 1-continued

Selected imidazoquinoline compositions.

| Compound No. | X | $\underset{(CR_2R_3)_n}{\overset{R_1}{N}}{-}YR_8$ | L | $R_7$ | $R_4$ | $R_5, R_6$ |
|---|---|---|---|---|---|---|
| 7 | absent | N-methylpiperazinyl | —(CH$_2$)$_2$— | morpholino | OH | H, H |
| 8 | 1,4-phenylene | N-methylpiperazinyl | —(CH$_2$)$_2$— | morpholino | SH | H, H |
| 9 | 1,4-phenylene | N-methylpiperazinyl | —(CH$_2$)$_2$— | morpholino | Br | H, H |
| 10 | 1,4-phenylene | N-methylpiperazinyl | —(CH$_2$)$_2$— | morpholino | Cl | H, H |
| 11 | 1,4-phenylene | N-methylpiperazinyl | —(CH$_2$)$_2$— | morpholino | SCH$_3$ | H, H |
| 12 | 1,4-phenylene | N-methylpiperazinyl | —(CH$_2$)$_2$— | morpholino | SO$_2$CH$_3$ | H, H |
| 13 | 1,4-phenylene | N-methylpiperazinyl | —(CH$_2$)$_2$— | morpholino | OCH$_3$ | H, H |
| 14 | 1,4-phenylene | N-methylpiperazinyl | —(CH$_2$)$_2$— | N(CH$_3$)$_2$ | OH | H, phenyl |
| 15 | 1,3-phenylene | N-methylpiperazinyl | —(CH$_2$)$_2$— | morpholino | H | H, H |

TABLE 1-continued

Selected imidazoquinoline compositions.

| Compound No. | X | $\begin{array}{c}R_1\\|\\N\\\diagdown\\(CR_2R_3)_n\diagup YR_8\end{array}$ | L | $R_7$ | $R_4$ | $R_5, R_6$ |
|---|---|---|---|---|---|---|
| 16 | absent | 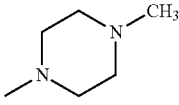 | —(CH$_2$)$_2$— | 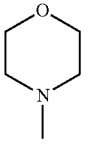 | CH$_3$ | H, CH$_3$ |
| 17 | 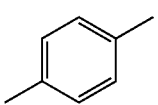 | 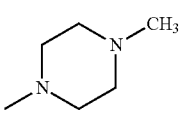 | —(CH$_2$)$_2$— | 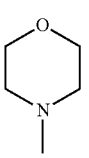 | CH$_2$OEt | H, H |
| 18 | 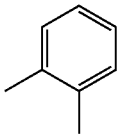 | 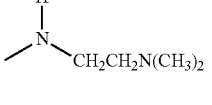 | —(CH$_2$)$_2$— | 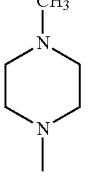 | CH$_2$OEt | H, H |
| 19 | 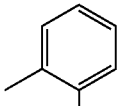 | 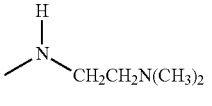 | —(CH$_2$)$_2$— | 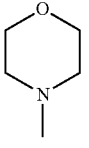 | H | CH$_3$, CH$_3$ |
| 20 | 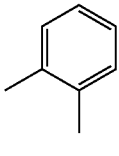 | 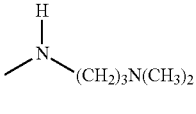 | —(CH$_2$)$_2$— | N(CH$_3$)$_2$ | OH | H, H |
| 21 | absent | 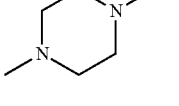 | —(CH$_2$)$_2$— | N(CH$_3$)$_2$ | CH$_3$ | H, H |
| 22 | absent | 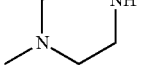 | —(CH$_2$)$_2$— | N(CH$_3$)$_2$ | CH$_3$ | H, t-Bu |
| 23 | absent | 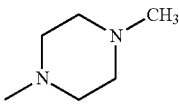 | —(CH$_2$)$_2$— | N(CH$_3$)$_2$ | H | CH$_3$, t-Bu |
| 24 | absent | 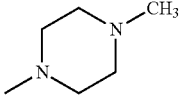 | —(CH$_2$)$_2$— | N(CH$_3$)$_2$ | H | H, H |

TABLE 2

Additional selected imidazoquinoline compositions

| Example No. | X–N(R₁)–(CR₂R₃)ₙ–YR₈ | L | R₇ | R₄ | R₅, R₆ |
|---|---|---|---|---|---|
| 25 | 1-(4-methylphenyl)-4-methylpiperazine | —(CH$_2$)$_4$— | 4-methylmorpholine | H | H, H |
| 26 | 1-(4-methylphenyl)-4-methylpiperazine | —(CH$_2$)$_3$— | 4-methylmorpholine | CH$_3$ | H, H |
| 27 | 1-(4-methylphenyl)-4-methylpiperazine | —(CH$_2$)$_4$— | N(CH$_3$)$_2$ | CH$_2$OEt | H, H |
| 28 | 1-(4-methylphenyl)-4-methylpiperazine | —(CH$_2$)$_5$— | N(CH$_3$)$_2$ | CH$_2$OEt | H, H |
| 29 | 1-(3-methylphenyl)-4-methylpiperazine | —(CH$_2$)$_2$— | N(CH$_3$)$_2$ | OH | CH$_3$, Et |
| 30 | 1-(4-methylphenyl)-4-methylpiperazine | —(CH$_2$)$_2$— | N(Et)$_2$ | OH | H, H |
| 31 | 1-(4-methylphenyl)-4-methylpiperazine | —(CH$_2$)$_4$— | N(CH$_3$)$_2$ | CH$_2$OEt | H, 4-methylphenyl |
| 32 | N-(2-methylphenyl)-N'-(2-dimethylaminoethyl)amine | —(CH$_2$)$_2$— | NEtPh | Et | Et, Et |

TABLE 2-continued

Additional selected imidazoquinoline compositions

Structure header: X-N(R1)-(CR2R3)n-YR8

| Example No. | X-N(R1)-(CR2R3)n-YR8 | L | R7 | R4 | R5, R6 |
|---|---|---|---|---|---|
| 33 | 2-methylphenyl-NH-CH2CH2N(CH3)2 | —(CH2)2— | N(CH3)2 | CH3 | H, H |
| 34 | 2-methylphenyl-NH-(CH2)3N(CH3)2 | —(CH2)5— | N(CH3)2 | CH2OEt | H, H |
| 35 | 4-methylbenzyl-(4-methylpiperazin-1-yl) | —(CH2)3— | N(CH3)2 | CH2OEt | H, H |
| 36 | 4-methylphenyl-(4-methylpiperazin-1-yl) | —(CH2)4— | 4-methylpiperazin-1-yl | CH3 | F, H |
| 37 | 4-methylphenyl-(4-methylpiperazin-1-yl) | —(CH2)4— | morpholin-4-yl | n-Pr | CH3, n-Bu |
| 38 | 4-methylphenyl-(4-methylpiperazin-1-yl) | —(CH2)2— | 4-methylpiperazin-1-yl | CH3 | CH3, n-Bu |
| 39 | 4-methylphenyl-(4-methylpiperazin-1-yl) | —(CH2)2— | N(CH3)2 | CH2OEt | F, Cl |
| 40 | 7-methylnaphth-2-ylmethyl-(4-methylpiperazin-1-yl) | —(CH2)2— | N(CH3)2 | CH2OEt | H, H |
| 41 | 3-methylphenyl-(4-methylpiperazin-1-yl) | —(CH2)2— | N(CH3)2 | CH2OEt | Cl, H |

TABLE 2-continued
Additional selected imidazoquinoline compositions
| Example No. | X-N(R₁)(CR₂R₃)ₙ-YR₈ | L | R₇ | R₄ | R₅, R₆ |
|---|---|---|---|---|---|
| 42 | 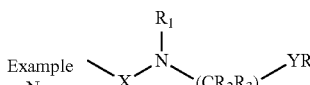 | —(CH₂)₂— | N(CH₃)₂ | CH₂OEt | Cl, Cl |
| 43 | 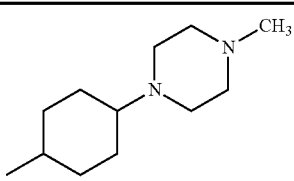 | —(CH₂)₂— | N(CH₃)₂ | CH₂OEt | H, H |
| 44 | 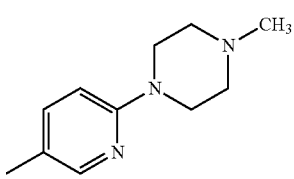 | —(CH₂)₂— | N(CH₃)₂ | H | Cl, Br |
| 45 | 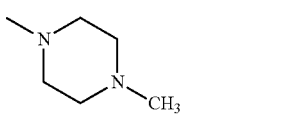 | —(CH₂)₂— | N(CH₃)₂ | H | H, H |
| 46 | 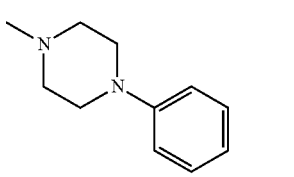 | —(CH₂)₂— | 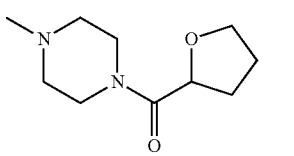 | H | H, H |
| 47 | 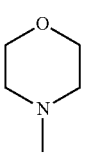 | —(CH₂)₂— | NHCH₃ | H | H, H |
| 48 | 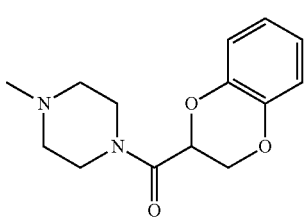 [SMILES: CN1CCN(C(=O)C2COc3ccccc3O2)CC1] | —(CH₂)₃— | N(Et)₂ | CH₂OEt | H, H |
| 49 | 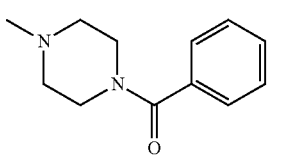 | —(CH₂)₂— | NHBn | CH₂OEt | H, H |
| 50 | 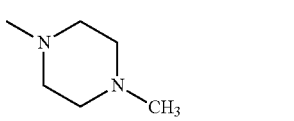 | —(CH₂)₃— | NHBn | OH | H, H |

TABLE 2-continued
Additional selected imidazoquinoline compositions
| Example No. | X-N(R₁)-(CR₂R₃)ₙ-YR₈ | L | R₇ | R₄ | R₅, R₆ |
|---|---|---|---|---|---|
| 51 | 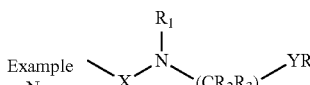 | —(CH₂)₂— | NHBn | CH₂OEt | H, H |
| 52 | 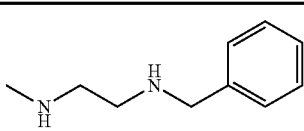 | —(CH₂)₂— | NMeBn | CH₂OEt | H, H |
| 53 | 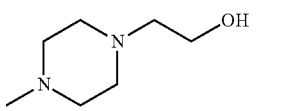 | —(CH₂)₂— | NHMe | CH₂OEt | H, H |
| 54 | 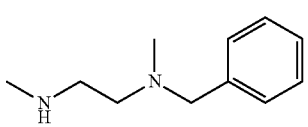 | —(CH₂)₂— | 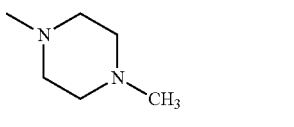 | Et | F, F |
| 55 | 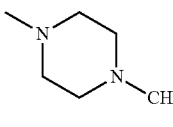 | —(CH₂)₂— | 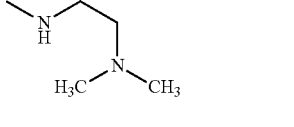 | Et | H, OCF₃ |
| 56 | 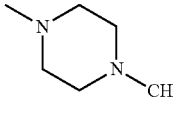 | —(CH₂)₂— | 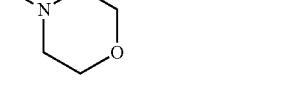 | Bn | Cl, Cl |
| 57 | 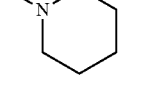 | —(CH₂)₂— | 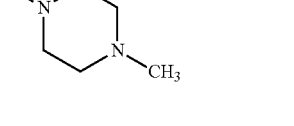 | Et | R5 = Et, R6 = 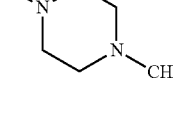 |
| 58 | 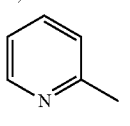 | —(CH₂)₂— | 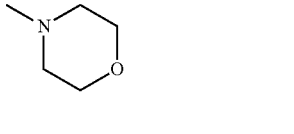 | Bn | 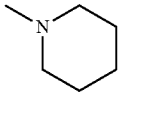 |
| 59 | 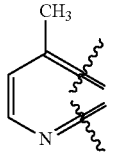 | —(CH₂)₂— | 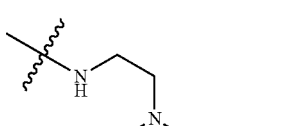 | Et | R5 = H, R6 = n-propyl |
| 60 | 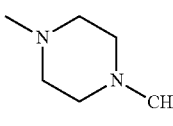 | —(CH₂)₂— | 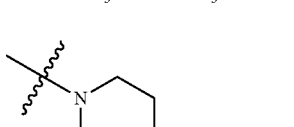 | CH₂OEt | R5 = H, R6 = H |

TABLE 2-continued
Additional selected imidazoquinoline compositions
| Example No. | X–N(R₁)(CR₂R₃)ₙYR₈ | L | R₇ | R₄ | R₅, R₆ |
|---|---|---|---|---|---|
| 61 | 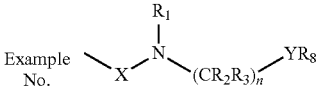 | —(CH₂)₂— | NMe₂ | CH₂OEt | R5 = H, R6 = H |
| 62 | 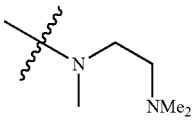 [SMILES: *N(C)CCN(C)C] | —(CH₂)₂— | NMe₂ | CH₂OEt | R5 = H, R6 = H |
| 63 | 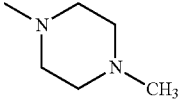 | —(CH₂)₂— | —OCH₂CH₂OH | CH₂OEt | R5 = H, R6 = H |
| 64 | 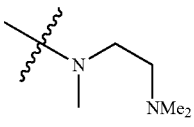 | —(CH₂)₂— | —OCH₂CH₂OH | CH₂OEt | R5 = H, R6 = H |
| 65 | 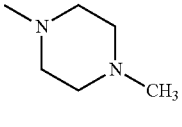 | —(CH₂)₂— | 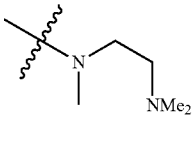 [SMILES: *N(C)CCN(C)C] | CH₂OEt | R5 = H, R6 = H |
| 66 | 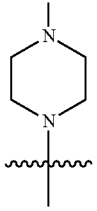 | —(CH₂)₂— | 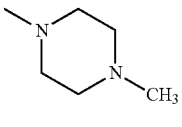 | CH₂OEt | R5 = H, R6 = H |
| 67 | 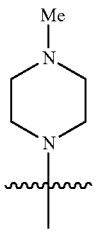 | —(CH₂)₂— | NMe₂ | H | R5 = H, R6 = H |
| 68 | 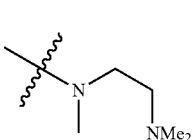 | —(CH₂)₂— | NMe₂ | OH | R5 = H, R6 = H |
| 69 | 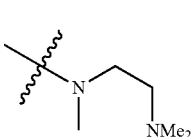 | —(CH₂)₂— | 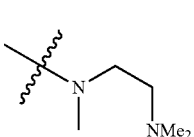 | OH | R5 = H, R6 = H |

TABLE 2-continued

Additional selected imidazoquinoline compositions

| Example No. | ![X-N(R1)-(CR2R3)n-YR8 structure] | L | R7 | R4 | R5, R6 |
|---|---|---|---|---|---|
| 70 | *N(Me)-CH2CH2-NH-CH3 group* | —(CH$_2$)$_2$— | *N-methylpiperazinyl* | H | R5 = H, R6 = H |

In another aspect, the present invention provides a pharmaceutical composition comprising at least one compound of formulae I, II, and III as described herein and a pharmaceutically-acceptable carrier or diluent.

In yet another aspect, the present invention provides a method for treating an autoimmune disease in a mammalian species in need thereof, the method comprising administering to the mammalian species a therapeutically effective amount of at least one compound of Formula I,

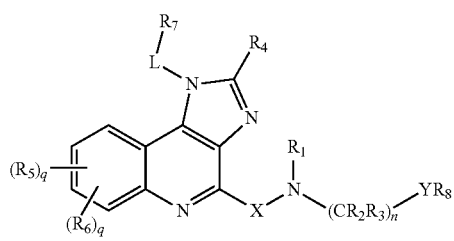

(I)

wherein

X is absent or is an alkyl, cycloalkyl, aryl, aralkyl, or heterocycle;

each occurrence of $R_1$ is independently hydrogen, alkyl, cycloalkyl, alkenyl, cycloalkenyl, alkynyl, heterocycle, or aryl;

each occurrence of $R_2$ and $R_3$ is independently hydrogen, alkyl, cycloalkyl, OH, alkoxy, —(CH$_2$)$_p$NR$_a$R$_b$, or $R_2$ and $R_3$ together with the carbon atom to which they are bonded optionally form a (C$_3$-C$_7$)cycloalkyl;

n is an integer of 2-4;

each q is an integer of 1-2;

Y is NR$_9$ or O;

$R_8$ is hydrogen, alkyl, cycloalkyl, monocyclic heterocycle, or aryl;

$R_9$ is H, Me, Et, n-Pr, i-Pr, n-Bu, i-Bu, t-Bu, CH$_2$CMe$_3$, Ph, CH$_2$Ph, C(=O)R$_{12}$, (CH$_2$)$_p$OR$_a$, and (CH$_2$)$_p$NR$_b$R$_c$, wherein R$_{12}$ is alkyl, phenyl, or heterocycle; R$_a$, R$_b$ and R$_c$ are each independently hydrogen, or (C$_1$-C$_4$)alkyl, or R$_b$ and R$_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a heterocycle comprising 1-4 heteroatoms, wherein the heterocycle is optionally substituted by (C$_1$-C$_4$)alkyl;

or $R_1$ and $R_8$ optionally form a heterocycle comprising 2-4 heteroatoms, wherein the heterocycle is optionally substituted by (C$_1$-C$_4$)alkyl;

$R_4$ is hydrogen, halogen, cyano, nitro, CF$_3$, OCF$_3$, alkyl, cycloalkyl, alkenyl, aryl, heterocycle, OR$_a$, —CH$_2$OR$_a$, SR$_a$, S(=O)R$_a$, S(=O)$_2$R$_a$, NR$_b$R$_c$, S(=O)$_2$NR$_b$R$_c$, C(=O)OR$_a$, C(=O)R$_a$, C(=O)NR$_b$R$_c$, OC(=O)R$_a$, OC(=O)NR$_b$R$_c$, NR$_b$C(=O)OR$_a$, NR$_b$C(=O)R$_a$;

$R_5$ and $R_6$ are each independently hydrogen, halogen, cyano, nitro, CF$_3$, OCF$_3$, alkyl, cycloalkyl, alkenyl, aryl, heterocycle, OR$_a$, SR$_a$, S(=O)R$_a$, S(=O)$_2$R$_a$, NR$_b$R$_c$, S(=O)$_2$NR$_b$R$_c$, C(=O)OR$_a$, C(=O)R$_a$, C(=O)NR$_b$R$_c$, OC(=O)R$_a$, OC(=O)NR$_b$R$_c$, NR$_b$C(=O)OR$_a$, NR$_b$C(=O)R$_a$, alkaryl, alkylheterocyclic, or NR$_b$(CH$_2$)$_p$NR$_b$R$_c$; or said $R_5$ and $R_6$ together with the carbon atoms to which they are bonded optionally form a heterocycle comprising 1-4 heteroatoms, wherein the heterocycle is optionally substituted by (C$_1$-C$_4$)alkyl;

L is absent or is alkyl or alkenyl containing from 2 to 10 carbon atoms;

$R_7$ is H, alkyl, heteroaryl, —O(CH$_2$)$_p$OR$_a$, or NR$_{10}$R$_{11}$, wherein the heteroaryl are optionally substituted by (C$_1$-C$_4$) alkyl;

$R_{10}$ and $R_{11}$ are each independently hydrogen, alkyl, cycloalkyl, alkenyl, aryl or alkylaryl, or $R_{10}$ and $R_{11}$ together with the nitrogen atom to which they are bonded form a heterocycle;

p is an integer of 0, 1, 2, 3, 4, 5, or 6;

each occurrence of R$_a$ is independently hydrogen, alkyl, cycloalkyl, alkenyl, cycloalkenyl, alkynyl, heterocycle, or aryl; and each occurrence of R$_b$, and R$_c$ is independently hydrogen, alkyl, cycloalkyl, heterocycle, aryl, or said R$_b$ and R$_c$ together with the nitrogen atom to which they are bonded optionally form a heterocycle comprising 1-4 heteroatoms, wherein the heterocycle is optionally substituted by (C$_1$-C$_4$) alkyl.

In yet another aspect, the present invention provides a method for treating an autoimmune disease in a mammalian species in need thereof, the method comprising administering to the mammalian species a therapeutically effective amount of at least one compound of Formula II, (II)

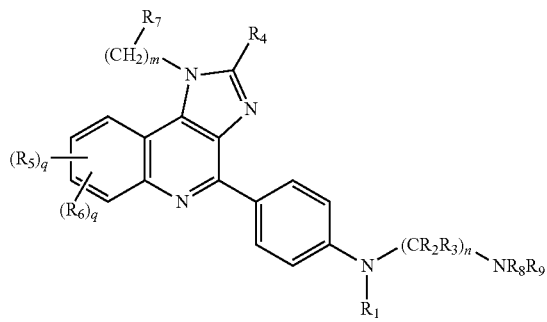

wherein each occurrence of $R_1$ is independently hydrogen, $(C_1$-$C_4)$alkyl, $(C_3$-$C_7)$cycloalkyl, $(C_2$-$C_6)$alkenyl, $(C_2$-$C_6)$alkynyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

each occurrence of $R_2$ and $R_3$ is independently hydrogen, $(C_1$-$C_4)$alkyl, $(C_3$-$C_7)$cycloalkyl, OH, $(C_1$-$C_4)$alkoxy, —$(CH_2)_pNR_aR_b$, or $R_2$ and $R_3$ together with the carbon atom to which they are bonded optionally form a $(C_3$-$C_6)$ cycloalkyl;

$R_8$ is hydrogen, $(C_1$-$C_4)$alkyl, $(C_3$-$C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

$R_9$ is H, Me, Et, n-Pr, i-Pr, n-Bu, i-Bu, t-Bu, $CH_2CMe_3$, Ph, $CH_2$Ph, $C(=O)R_{12}$, $(CH_2)_pOR_a$, and $(CH_2)_pNR_bR_c$, wherein $R_{12}$ is $(C_1$-$C_4)$alkyl, phenyl, or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; $R_a$, $R_b$ and $R_c$ are each independently hydrogen, or $(C_1$-$C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a 3- to 7-membered heterocycle which may be saturated or unsaturated comprising 1-4 heteroatoms, wherein the heterocycle is optionally substituted by $(C_1$-$C_4)$alkyl;

or $R_1$ and $R_8$ optionally form a 5- to 7-membered heterocycle which may be saturated or unsaturated comprising 2-4 heteroatoms, wherein the heterocycle is optionally substituted by $(C_1$-$C_4)$alkyl;

$R_4$ is hydrogen, halogen, cyano, nitro, $CF_3$, $OCF_3$, $(C_1$-$C_4)$alkyl, $(C_3$-$C_7)$cycloalkyl, $(C_2$-$C_6)$alkenyl, aryl, heterocycle, $OR_a$, —$CH_2OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

$R_5$ and $R_6$ are each independently hydrogen, halogen, cyano, nitro, $CF_3$, $OCF_3$, $(C_1$-$C_4)$alkyl, $(C_3$-$C_7)$cycloalkyl, $(C_2$-$C_6)$alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, alkaryl, alkylheterocyclic, or $NR_b(CH_2)_pNR_bR_c$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

L is alkyl or alkenyl containing from 2 to 10 carbon atoms;

$R_7$ is H, $(C_1$-$C_4)$alkyl, heteroaryl, —$O(CH_2)_pOR_a$, or $NR_{10}R_{11}$, wherein the heteroaryl is a 5- to 6-membered aromatic ring which may be saturated or unsaturated containing one to three heteroatoms which may the same or different selected from nitrogen, sulfur and oxygen, and the heteroaryl is optionally substituted by $(C_1$-$C_4)$alkyl;

$R_{10}$ and $R_{11}$ are each independently hydrogen, $(C_1$-$C_4)$alkyl, $(C_3$-$C_7)$cycloalkyl, $(C_2$-$C_6)$alkenyl, aryl or $(C_1$-$C_4)$alkylaryl, or $R_{10}$ and $R_{11}$ together with the nitrogen atom to which they are bonded form a 3- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

m is an integer of 2-6;

n is an integer of 2-4;

each q is an integer of 1-2;

each occurrence of $R_a$ is independently hydrogen, $(C_1$-$C_4)$alkyl, $(C_3$-$C_7)$cycloalkyl, $(C_2$-$C_6)$alkenyl, $(C_5$-$C_7)$cycloalkenyl, $(C_2$-$C_6)$alkynyl, aryl, or a 3- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; and each occurrence of $R_b$ and $R_c$ is independently hydrogen, $(C_1$-$C_4)$alkyl, $(C_3$-$C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; or said $R_b$ and $R_c$ together with the nitrogen atom to which they are bonded optionally form a 3- to 7-membered heterocycle which may be saturated or unsaturated comprising 1-4 heteroatoms, wherein the heterocycle is optionally substituted by $(C_1$-$C_4)$alkyl.

In yet another aspect, the present invention provides a method for treating an autoimmune disease in a mammalian species in need thereof, the method comprising administering to the mammalian species a therapeutically effective amount of at least one compound of Formula III,

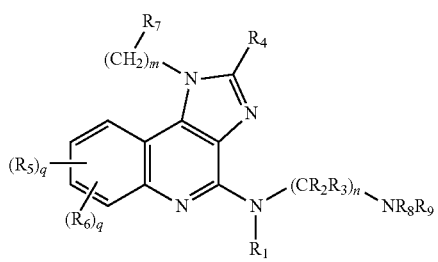

(III)

wherein each occurrence of $R_1$ is independently hydrogen, $(C_1$-$C_4)$alkyl, $(C_3$-$C_7)$cycloalkyl, $(C_2$-$C_6)$alkenyl, $(C_2$-$C_6)$alkynyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

each occurrence of $R_2$ and $R_3$ is independently hydrogen, $(C_1$-$C_4)$alkyl, $(C_3$-$C_7)$cycloalkyl, OH, $(C_1$-$C_4)$alkoxy, —$(CH_2)_pNR_aR_b$, or $R_2$ and $R_3$ together with the carbon atom to which they are bonded optionally form a $(C_3$-$C_6)$ cycloalkyl;

$R_8$ is hydrogen, $(C_1$-$C_4)$alkyl, $(C_3$-$C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

$R_9$ is H, Me, Et, n-Pr, i-Pr, n-Bu, i-Bu, t-Bu, $CH_2CMe_3$, Ph, $CH_2Ph$, $C(=O)R_{12}$, $(CH_2)_pOR_a$, and $(CH_2)_pNR_bR_c$, wherein $R_{12}$ is $(C_1$-$C_4)$alkyl, phenyl, or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; $R_a$, $R_b$ and $R_c$ are each independently hydrogen, or $(C_1$-$C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a 3- to 7-membered heterocycle which may be saturated or unsaturated comprising 1-4 heteroatoms, wherein the heterocycle is optionally substituted by $(C_1$-$C_4)$alkyl;

or $R_1$ and $R_8$ optionally form a 5- to 7-membered heterocycle which may be saturated or unsaturated comprising 2-4 heteroatoms, wherein the heterocycle is optionally substituted by $(C_1$-$C_4)$alkyl;

$R_4$ is hydrogen, halogen, cyano, nitro, $CF_3$, $OCF_3$, $(C_1$-$C_4)$alkyl, $(C_3$-$C_7)$cycloalkyl, $(C_2$-$C_6)$alkenyl, aryl, heterocycle, $OR_a$, —$CH_2OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

$R_5$ and $R_6$ are each independently hydrogen, halogen, cyano, nitro, $CF_3$, $OCF_3$, $(C_1$-$C_4)$alkyl, $(C_3$-$C_7)$cycloalkyl, $(C_2$-$C_6)$alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, alkaryl, alkylheterocyclic, or $NR_b(CH_2)_pNR_bR_c$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

L is alkyl or alkenyl containing from 2 to 10 carbon atoms;

$R_7$ is H, $(C_1$-$C_4)$alkyl, heteroaryl, —$O(CH_2)_pOR_a$, or $NR_{10}R_{11}$, wherein the heteroaryl is a 5- to 6-membered aromatic ring which may be saturated or unsaturated containing one to three heteroatoms which may the same or different selected from nitrogen, sulfur and oxygen, and the heteroaryl is optionally substituted by $(C_1$-$C_4)$alkyl;

m is an integer of 2-6;

n is an integer of 2-4;

each q is an integer of 1-2;

$R_{10}$ and $R_{11}$ are each independently hydrogen, $(C_1$-$C_4)$ alkyl, $(C_3$-$C_7)$cycloalkyl, $(C_2$-$C_6)$alkenyl, aryl or $(C_1$-$C_4)$ alkylaryl, or $R_{10}$ and $R_{11}$ together with the nitrogen atom to which they are bonded form a 3- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

each occurrence of $R_a$ is independently hydrogen, $(C_1$-$C_4)$alkyl, $(C_3$-$C_7)$cycloalkyl, $(C_2$-$C_6)$alkenyl, $(C_5$-$C_7)$cycloalkenyl, $(C_2$-$C_6)$alkynyl, aryl, or a 3- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; and each occurrence of $R_b$ and $R_c$ is independently hydrogen, $(C_1$-$C_4)$alkyl, $(C_3$-$C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; or said $R_b$ and $R_c$ together with the nitrogen atom to which they are bonded optionally form a 3- to 7-membered heterocycle which may be saturated or unsaturated comprising 1-4 heteroatoms, wherein the heterocycle is optionally substituted by $(C_1$-$C_4)$alkyl.

In certain embodiments, the imidazoquinoline composition is in the form a hydrate or pharmaceutically acceptable salt. The imidazoquinoline composition can be administered to the subject by any suitable route of administration, including, without limitation, oral and parenteral. Parenteral routes of administration are as described above with respect to substituted 4-primary amino imidazoquinolines.

In certain embodiments, pharmaceutically acceptable hydrates and salts of the above and pharmaceutically acceptable hydrates and salts of the compound described herein are provided, to inhibit signaling by the TLR. The method according to this aspect of the invention can be performed in vitro or it can be performed in vivo. In addition, the cell expressing the functional TLR can, but need not necessarily, be an immune cell. For example, the cell expressing the functional TLR can be a cell transfected with an expression vector that directs expression of the TLR by the cell. In one embodiment the TLR is TLR9 and the method is thus a method for inhibiting intracellular signaling by TLR9. In one embodiment, the TLR is TLR8 and the method is thus a method for inhibiting intracellular signaling by TLR8. In one embodiment, the TLR is TLR7 and the method is thus a method for inhibiting intracellular signaling by TLR7. In one embodiment, the TLR is TLR3 and the method is thus a method for inhibiting intracellular signaling by TLR3.

In certain embodiments, the autoimmune disease is selected from cutaneous and systemic lupus erythematosus, insulin-dependent diabetes mellitus, rheumatoid arthritis, multiple sclerosis, atherosclerosis, psoriasis, psoriatic arthritis, inflammatory bowel disease, ankylosing spondylitis, autoimmune hemolytic anemia, Behcet's syndrome, Goodpasture's syndrome, Graves' disease, Guillain-Barre syndrome, Hashimoto's thyroiditis, idiopathic thrombocytopenia, io myasthenia gravis, pernicious anemia, polyarteritis nodosa, polymyositis/dermatomyositis, primary biliary sclerosis, sarcoidosis, sclerosing cholangitis, Sjogren's syndrome, systemic sclerosis (scleroderma and CREST syndrome), Takayasu's arteritis, temporal arteritis, and Wegener's granulomatosis.

In some embodiments, the autoimmune disease is selected from the group consisting of systemic lupus erythematosus, rheumatoid arthritis, psoriasis, inflammatory bowel disease, Sjogren's syndrome, polymyositis, vasculitis, Wegener's granulomatosis, sarcoidosis, ankylosing spondylitis, Reiter's syndrome, psoriatic arthritis, and Behcet's syndrome. In one particular embodiment, the autoimmune disease is systemic lupus erythematosus. In another particular embodiment, the autoimmune disease is rheumatoid arthritis. In one particular embodiment, the autoimmune disease is psoriasis. In yet another particular embodiment, the autoimmune disease is Sjogren's syndrome. In one embodiment, the subject is a human. In one embodiment, the autoimmune disorder is an immune complex associated disease, as described above.

In yet another aspect, the present invention provides a method of inhibiting TLR-mediated immunostimulation in a mammalian species in need thereof, comprising administering to the mammalian species a therapeutically effective amount of at least one compound of Formula I,

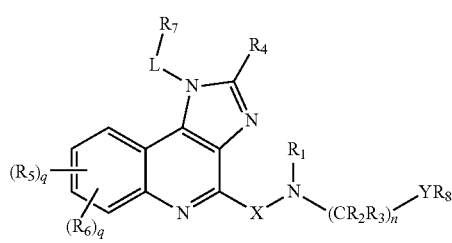

(I)

wherein

X is absent or is an alkyl, cycloalkyl, aryl, aralkyl, or heterocycle;

each occurrence of $R_1$ is independently hydrogen, alkyl, cycloalkyl, alkenyl, cycloalkenyl, alkynyl, heterocycle, or aryl;

each occurrence of $R_2$ and $R_3$ is independently hydrogen, alkyl, cycloalkyl, OH, alkoxy, —$(CH_2)_pNR_aR_b$, or $R_2$ and $R_3$ together with the carbon atom to which they are bonded optionally form a $(C_3-C_7)$cycloalkyl;

n is an integer of 2-4;

each q is an integer of 1-2;

Y is $NR_9$ or O;

$R_8$ is hydrogen, alkyl, cycloalkyl, monocyclic heterocycle, or aryl;

$R_9$ is H, Me, Et, n-Pr, i-Pr, n-Bu, i-Bu, t-Bu, $CH_2CMe_3$, Ph, $CH_2Ph$, C(=O)$R_{12}$, $(CH_2)_pOR_a$, and $(CH_2)_pNR_bR_c$, wherein $R_{12}$ is alkyl, phenyl, or heterocycle; $R_a$, $R_b$ and $R_c$ are each independently hydrogen, or $(C_1-C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a heterocycle comprising 1-4 heteroatoms, wherein the heterocycle is optionally substituted by $(C_1-C_4)$alkyl;

or $R_1$ and $R_8$ optionally form a heterocycle comprising 2-4 heteroatoms, wherein the heterocycle is optionally substituted by $(C_1-C_4)$alkyl;

$R_4$ is hydrogen, halogen, cyano, nitro, $CF_3$, $OCF_3$, alkyl, cycloalkyl, alkenyl, aryl, heterocycle, $OR_a$, —$CH_2OR_a$, $SR_a$, S(=O)$R_a$, S(=O)$_2R_a$, $NR_bR_c$, S(=O)$_2NR_bR_c$, C(=O)$OR_a$, C(=O)$R_a$, C(=O)$NR_bR_c$, OC(=O)$R_a$, OC(=O)$NR_bR_c$, $NR_bC$(=O)$OR_a$, $NR_bC$(=O)$R_a$;

$R_5$ and $R_6$ are each independently hydrogen, halogen, cyano, nitro, $CF_3$, $OCF_3$, alkyl, cycloalkyl, alkenyl, aryl, heterocycle, $OR_a$, $SR_a$, S(=O)$R_a$, S(=O)$_2R_a$, $NR_bR_c$, S(=O)$_2NR_bR_c$, C(=O)$OR_a$, C(=O)$R_a$, C(=O)$NR_bR_c$, OC(=O)$R_a$, OC(=O)$NR_bR_c$, $NR_bC$(=O)$OR_a$, $NR_bC$(=O)$R_a$, alkaryl, alkylheterocyclic, or $NR_b(CH_2)_pNR_bR_c$; or said $R_5$ and $R_6$ together with the carbon atoms to which they are bonded optionally form a heterocycle comprising 1-4 heteroatoms, wherein the heterocycle is optionally substituted by $(C_1-C_4)$alkyl;

L is absent or is alkyl or alkenyl containing from 2 to 10 carbon atoms;

$R_7$ is H, alkyl, heteroaryl, —O$(CH_2)_pOR_a$, or $NR_{10}R_{11}$, wherein the heteroaryl are optionally substituted by $(C_1-C_4)$ alkyl;

$R_{10}$ and $R_{11}$ are each independently hydrogen, alkyl, cycloalkyl, alkenyl, aryl or alkylaryl, or $R_{10}$ and $R_{11}$ together with the nitrogen atom to which they are bonded form a heterocycle;

p is an integer of 0, 1, 2, 3, 4, 5, or 6;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle comprising 1-4 heteroatoms, wherein the heterocycle is optionally substituted by $(C_1-C_4)$ alkyl.

In yet another aspect, the present invention provides a method of inhibiting TLR-mediated immunostimulation in a mammalian species in need thereof, comprising administering to the mammalian species a therapeutically effective amount of at least one compound of Formula II,

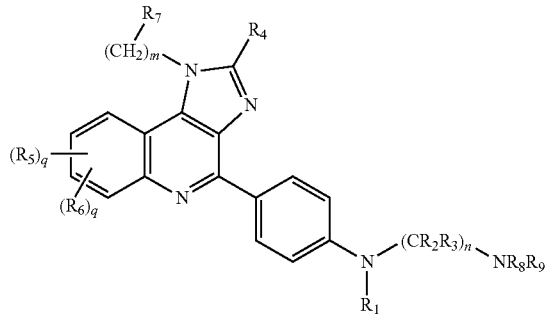

(II)

wherein each occurrence of $R_1$ is independently hydrogen, $(C_1-C_4)$alkyl, $(C_3-C_7)$cycloalkyl, $(C_2-C_6)$alkenyl, $(C_2-C_6)$alkynyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

each occurrence of $R_2$ and $R_3$ is independently hydrogen, $(C_1-C_4)$alkyl, $(C_3-C_7)$cycloalkyl, OH, $(C_1-C_4)$alkoxy, —$(CH_2)_pNR_aR_b$, or $R_2$ and $R_3$ together with the carbon atom to which they are bonded optionally form a $(C_3-C_6)$cycloalkyl;

$R_8$ is hydrogen, $(C_1-C_4)$alkyl, $(C_3-C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

$R_9$ is H, Me, Et, n-Pr, i-Pr, n-Bu, i-Bu, t-Bu, $CH_2CMe_3$, Ph, $CH_2Ph$, $C(=O)R_{12}$, $(CH_2)_pOR_a$, and $(CH_2)_pNR_bR_c$, wherein $R_{12}$ is $(C_1-C_4)$alkyl, phenyl, or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl; $R_a$, $R_b$ and $R_c$ are each independently hydrogen, or $(C_1-C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a 3- to 7-membered heterocycle which may be saturated or unsaturated comprising 1-4 heteroatoms, wherein the heterocycle is optionally substituted by $(C_1-C_4)$alkyl;

or $R_1$ and $R_8$ optionally form a 5- to 7-membered heterocycle which may be saturated or unsaturated comprising 2-4 heteroatoms, wherein the heterocycle is optionally substituted by $(C_1-C_4)$alkyl;

$R_4$ is hydrogen, halogen, cyano, nitro, $CF_3$, $OCF_3$, $(C_1-C_4)$alkyl, $(C_3-C_7)$cycloalkyl, $(C_2-C_6)$alkenyl, aryl, heterocycle, $OR_a$, —$CH_2OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

$R_5$ and $R_6$ are each independently hydrogen, halogen, cyano, nitro, $CF_3$, $OCF_3$, $(C_1-C_4)$alkyl, $(C_3-C_7)$cycloalkyl, $(C_2-C_6)$alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, alkaryl, alkylheterocyclic, or $NR_b(CH_2)_pNR_bR_c$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

L is alkyl or alkenyl containing from 2 to 10 carbon atoms;

$R_7$ is H, $(C_1-C_4)$alkyl, heteroaryl, —$O(CH_2)_pOR_a$, or $NR_{10}R_{11}$, wherein the heteroaryl is a 5- to 6-membered aromatic ring which may be saturated or unsaturated containing one to three heteroatoms which may the same or different selected from nitrogen, sulfur and oxygen, and the heteroaryl is optionally substituted by $(C_1-C_4)$alkyl;

$R_{10}$ and $R_{11}$ are each independently hydrogen, $(C_1-C_4)$alkyl, $(C_3-C_7)$cycloalkyl, $(C_2-C_6)$alkenyl, aryl or $(C_1-C_4)$alkylaryl, or $R_{10}$ and $R_{11}$ together with the nitrogen atom to which they are bonded form a 3- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

m is an integer of 2-6;

n is an integer of 2-4;

each q is an integer of 1-2;

each occurrence of $R_a$ is independently hydrogen, $(C_1-C_4)$alkyl, $(C_3-C_7)$cycloalkyl, $(C_2-C_6)$alkenyl, $(C_5-C_7)$cycloalkenyl, $(C_2-C_6)$alkynyl, aryl, or a 3- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl; and each occurrence of $R_b$ and $R_c$ is independently hydrogen, $(C_1-C_4)$alkyl, $(C_3-C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl; or said $R_b$ and $R_c$ together with the nitrogen atom to which they are bonded optionally form a 3- to 7-membered heterocycle which may be saturated or unsaturated comprising 1-4 heteroatoms, wherein the heterocycle is optionally substituted by $(C_1-C_4)$alkyl.

In yet another aspect, the present invention provides a method of inhibiting TLR-mediated immunostimulatory signaling, comprising contacting a cell expressing a TLR with an effective amount of at least one compound of Formula III,

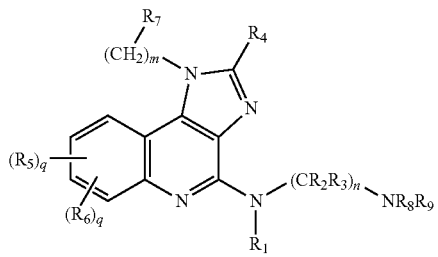

(III)

wherein each occurrence of $R_1$ is independently hydrogen, $(C_1$-$C_4)$alkyl, $(C_3$-$C_7)$cycloalkyl, $(C_2$-$C_6)$alkenyl, $(C_2$-$C_6)$alkynyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

each occurrence of $R_2$ and $R_3$ is independently hydrogen, $(C_1$-$C_4)$alkyl, $(C_3$-$C_7)$cycloalkyl, OH, $(C_1$-$C_4)$alkoxy, —$(CH_2)_pNR_aR_b$, or $R_2$ and $R_3$ together with the carbon atom to which they are bonded optionally form a $(C_3$-$C_6)$ cycloalkyl;

$R_8$ is hydrogen, $(C_1$-$C_4)$alkyl, $(C_3$-$C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

$R_9$ is H, Me, Et, n-Pr, i-Pr, n-Bu, i-Bu, t-Bu, $CH_2CMe_3$, Ph, $CH_2Ph$, $C(=O)R_{12}$, $(CH_2)_pOR_a$, and $(CH_2)_pNR_bR_c$, wherein $R_{12}$ is $(C_1$-$C_4)$alkyl, phenyl, or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; $R_a$, $R_b$ and $R_c$ are each independently hydrogen, or $(C_1$-$C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a 3- to 7-membered heterocycle which may be saturated or unsaturated comprising 1-4 heteroatoms, wherein the heterocycle is optionally substituted by $(C_1$-$C_4)$alkyl;

or $R_1$ and $R_8$ optionally form a 5- to 7-membered heterocycle which may be saturated or unsaturated comprising 2-4 heteroatoms, wherein the heterocycle is optionally substituted by $(C_1$-$C_4)$alkyl;

$R_4$ is hydrogen, halogen, cyano, nitro, $CF_3$, $OCF_3$, $(C_1$-$C_4)$alkyl, $(C_3$-$C_7)$cycloalkyl, $(C_2$-$C_6)$alkenyl, aryl, heterocycle, $OR_a$, —$CH_2OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

$R_5$ and $R_6$ are each independently hydrogen, halogen, cyano, nitro, $CF_3$, $OCF_3$, $(C_1$-$C_4)$alkyl, $(C_3$-$C_7)$cycloalkyl, $(C_2$-$C_6)$alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, alkaryl, alkylheterocyclic, or $NR_b(CH_2)_pNR_bR_c$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

L is alkyl or alkenyl containing from 2 to 10 carbon atoms;

$R_7$ is H, $(C_1$-$C_4)$alkyl, heteroaryl, —$O(CH_2)_pOR_a$, or $NR_{10}R_{11}$, wherein the heteroaryl is a 5- to 6-membered aromatic ring which may be saturated or unsaturated containing one to three heteroatoms which may the same or different selected from nitrogen, sulfur and oxygen, and the heteroaryl is optionally substituted by $(C_1$-$C_4)$alkyl;

m is an integer of 2-6;

n is an integer of 2-4;

each q is an integer of 1-2;

$R_{10}$ and $R_{11}$ are each independently hydrogen, $(C_1$-$C_4)$ alkyl, $(C_3$-$C_7)$cycloalkyl, $(C_2$-$C_6)$alkenyl, aryl or $(C_1$-$C_4)$ alkylaryl, or $R_{10}$ and $R_{11}$ together with the nitrogen atom to which they are bonded form a 3- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl;

each occurrence of $R_a$ is independently hydrogen, $(C_1$-$C_4)$alkyl, $(C_3$-$C_7)$cycloalkyl, $(C_2$-$C_6)$alkenyl, $(C_5$-$C_7)$cycloalkenyl, $(C_2$-$C_6)$alkynyl, aryl, or a 3- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; and each occurrence of $R_b$ and $R_c$ is independently hydrogen, $(C_1$-$C_4)$alkyl, $(C_3$-$C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1$-$C_4)$alkyl, phenyl or benzyl; or said $R_b$ and $R_c$ together with the nitrogen atom to which they are bonded optionally form a 3- to 7-membered heterocycle which may be saturated or unsaturated comprising 1-4 heteroatoms, wherein the heterocycle is optionally substituted by $(C_1$-$C_4)$alkyl.

In some embodiments, the method of affecting TLR-mediated immunostimulation in a subject comprises administering to a subject having or at risk of developing TLR-mediated immunostimulation an effective amount of a compound of Formulae I-III, as provided herein, to inhibit TLR-mediated immunostimulation in the subject.

In yet another aspect, the invention provides a method of inhibiting TLR-mediated immunostimulation in a subject. The method according to this aspect of the invention involves administering to a subject having or at risk of developing TLR-mediated immunostimulation an effective amount of a compound of one of Formulae I-III, as provided above, to inhibit TLR-mediated immunostimulation in the subject.

In yet another aspect, the present invention provides a method of inhibiting TLR-mediated immunostimulatory signaling, comprising contacting a cell expressing a TLR with an effective amount of at least one compound of Formula I,

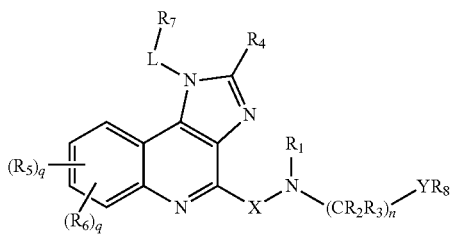

wherein

X is absent or is an alkyl, cycloalkyl, aryl, aralkyl, or heterocycle;

each occurrence of $R_1$ is independently hydrogen, alkyl, cycloalkyl, alkenyl, cycloalkenyl, alkynyl, heterocycle, or aryl;

each occurrence of $R_2$ and $R_3$ is independently hydrogen, alkyl, cycloalkyl, OH, alkoxy, —$(CH_2)_pNR_aR_b$, or $R_2$ and $R_3$ together with the carbon atom to which they are bonded optionally form a $(C_3-C_7)$cycloalkyl;

n is an integer of 2-4;

each q is an integer of 1-2;

Y is $NR_9$ or O;

$R_8$ is hydrogen, alkyl, cycloalkyl, monocyclic heterocycle, or aryl;

$R_9$ is H, Me, Et, n-Pr, i-Pr, n-Bu, i-Bu, t-Bu, $CH_2CMe_3$, Ph, $CH_2Ph$, C(=O)$R_{12}$, $(CH_2)_pOR_a$, and $(CH_2)_pNR_bR_c$, wherein $R_{12}$ is alkyl, phenyl, or heterocycle; $R_a$, $R_b$ and $R_c$ are each independently hydrogen, or $(C_1-C_4)$alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a heterocycle comprising 1-4 heteroatoms, wherein the heterocycle is optionally substituted by $(C_1-C_4)$alkyl;

or $R_1$ and $R_8$ optionally form a heterocycle comprising 2-4 heteroatoms, wherein the heterocycle is optionally substituted by $(C_1-C_4)$alkyl;

$R_4$ is hydrogen, halogen, cyano, nitro, $CF_3$, $OCF_3$, alkyl, cycloalkyl, alkenyl, aryl, heterocycle, $OR_a$, —$CH_2OR_a$, $SR_a$, S(=O)$R_a$, S(=O)$_2R_a$, $NR_bR_c$, S(=O)$_2NR_bR_c$, C(=O)$OR_a$, C(=O)$R_a$, C(=O)$NR_bR_c$, OC(=O)$R_a$, OC(=O)$NR_bR_c$, $NR_bC(=O)OR_a$, $NR_bC(=O)R_a$;

$R_5$ and $R_6$ are each independently hydrogen, halogen, cyano, nitro, $CF_3$, $OCF_3$, alkyl, cycloalkyl, alkenyl, aryl, heterocycle, $OR_a$, $SR_a$, S(=O)$R_a$, S(=O)$_2R_a$, $NR_bR_c$, S(=O)$_2NR_bR_c$, C(=O)$OR_a$, C(=O)$R_a$, C(=O)$NR_bR_c$, OC(=O)$R_a$, OC(=O)$NR_bR_c$, $NR_bC(=O)OR_a$, $NR_bC(=O)R_a$, alkaryl, alkylheterocyclic, or $NR_b(CH_2)_pNR_bR_c$; or said $R_5$ and $R_6$ together with the carbon atoms to which they are bonded optionally form a heterocycle comprising 1-4 heteroatoms, wherein the heterocycle is optionally substituted by $(C_1-C_4)$alkyl;

L is absent or is alkyl or alkenyl containing from 2 to 10 carbon atoms;

$R_7$ is H, alkyl, heteroaryl, —O$(CH_2)_pOR_a$, or $NR_{10}R_{11}$, wherein the heteroaryl are optionally substituted by $(C_1-C_4)$alkyl;

$R_{10}$ and $R_{11}$ are each independently hydrogen, alkyl, cycloalkyl, alkenyl, aryl or alkylaryl, or $R_{10}$ and $R_{11}$ together with the nitrogen atom to which they are bonded form a heterocycle;

p is an integer of 0, 1, 2, 3, 4, 5, or 6;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle comprising 1-4 heteroatoms, wherein the heterocycle is optionally substituted by $(C_1-C_4)$alkyl.

In yet another aspect, the present invention provides a method of inhibiting TLR-mediated immunostimulatory signaling, comprising contacting a cell expressing a TLR with an effective amount of at least one compound of Formula II,

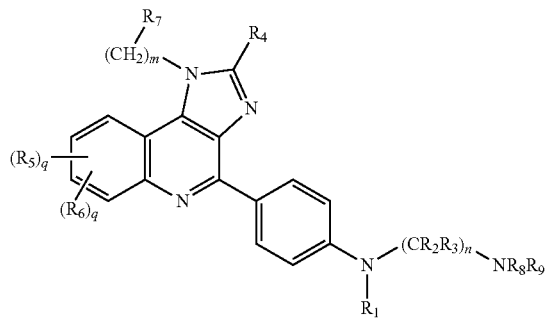

wherein each occurrence of $R_1$ is independently hydrogen, $(C_1-C_4)$alkyl, $(C_3-C_7)$cycloalkyl, $(C_2-C_6)$alkenyl, $(C_2-C_6)$alkynyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

each occurrence of $R_2$ and $R_3$ is independently hydrogen, $(C_1-C_4)$alkyl, $(C_3-C_7)$cycloalkyl, OH, $(C_1-C_4)$alkoxy, —$(CH_2)_pNR_aR_b$, or $R_2$ and $R_3$ together with the carbon atom to which they are bonded optionally form a $(C_3-C_6)$ cycloalkyl;

$R_8$ is hydrogen, $(C_1-C_4)$alkyl, $(C_3-C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

$R_9$ is H, Me, Et, n-Pr, i-Pr, n-Bu, i-Bu, t-Bu, $CH_2CMe_3$, Ph, $CH_2Ph$, C(=O)$R_{12}$, $(CH_2)_pOR_a$, and $(CH_2)_pNR_bR_c$, wherein $R_{12}$ is $(C_1-C_4)$alkyl, phenyl, or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl; $R_a$, $R_b$ and $R_c$ are each independently hydrogen, or (C$_1$-C$_4$)alkyl, or R$_b$ and R$_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said R$_8$ and R$_9$ together with the nitrogen atom to which they are bonded optionally form a 3- to 7-membered heterocycle which may be saturated or unsaturated comprising 1-4 heteroatoms, wherein the heterocycle is optionally substituted by (C$_1$-C$_4$)alkyl;

or R$_1$ and R$_8$ optionally form a 5- to 7-membered heterocycle which may be saturated or unsaturated comprising 2-4 heteroatoms, wherein the heterocycle is optionally substituted by (C$_1$-C$_4$)alkyl;

R$_4$ is hydrogen, halogen, cyano, nitro, CF$_3$, OCF$_3$, (C$_1$-C$_4$)alkyl, (C$_3$-C$_7$)cycloalkyl, (C$_2$-C$_6$)alkenyl, aryl, heterocycle, OR$_a$, —CH$_2$OR$_a$, SR$_a$, S(=O)R$_a$, S(=O)$_2$R$_a$, NR$_b$R$_c$, S(=O)$_2$NR$_b$R$_c$, C(=O)OR$_a$, C(=O)R$_a$, C(=O)NR$_b$R$_c$, OC(=O)R$_a$, OC(=O)NR$_b$R$_c$, NR$_b$C(=O)OR$_a$, NR$_b$C(=O)R$_a$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by (C$_1$-C$_4$)alkyl, phenyl or benzyl;

R$_5$ and R$_6$ are each independently hydrogen, halogen, cyano, nitro, CF$_3$, OCF$_3$, (C$_1$-C$_4$)alkyl, (C$_3$-C$_7$)cycloalkyl, (C$_2$-C$_6$)alkenyl, aryl, heterocycle, OR$_a$, SR$_a$, S(=O)R$_a$, S(=O)$_2$R$_a$, NR$_b$R$_c$, S(=O)$_2$NR$_b$R$_c$, C(=O)OR$_a$, C(=O)R$_a$, C(=O)NR$_b$R$_c$, OC(=O)R$_a$, OC(=O)NR$_b$R$_c$, NR$_b$C(=O)OR$_a$, NR$_b$C(=O)R$_a$, alkaryl, alkylheterocyclic, or NR$_b$(CH$_2$)$_p$NR$_b$R$_c$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by (C$_1$-C$_4$)alkyl, phenyl or benzyl;

L is alkyl or alkenyl containing from 2 to 10 carbon atoms;

R$_7$ is H, (C$_1$-C$_4$)alkyl, heteroaryl, —O(CH$_2$)$_p$OR$_a$, or NR$_{10}$R$_{11}$, wherein the heteroaryl is a 5- to 6-membered aromatic ring which may be saturated or unsaturated containing one to three heteroatoms which may the same or different selected from nitrogen, sulfur and oxygen, and the heteroaryl is optionally substituted by (C$_1$-C$_4$)alkyl;

R$_{10}$ and R$_{11}$ are each independently hydrogen, (C$_1$-C$_4$)alkyl, (C$_3$-C$_7$)cycloalkyl, (C$_2$-C$_6$)alkenyl, aryl or (C$_1$-C$_4$)alkylaryl, or R$_{10}$ and R$_{11}$ together with the nitrogen atom to which they are bonded form a 3- to 7-membered heterocycle which may be saturated or unsaturated containing one to three heteroatoms which may the same or different selected from nitrogen, sulfur and oxygen, in which the heterocycle is optionally substituted by (C$_1$-C$_4$)alkyl, phenyl or benzyl;

m is an integer of 2-6;
n is an integer of 2-4;
each q is an integer of 1-2;
each occurrence of R$_a$ is independently hydrogen, (C$_1$-C$_4$)alkyl, (C$_3$-C$_7$)cycloalkyl, (C$_2$-C$_6$)alkenyl, (C$_5$-C$_7$)cycloalkenyl, (C$_2$-C$_6$)alkynyl, aryl, or a 3- to 7-membered heterocycle which may be saturated or unsaturated containing one to three heteroatoms which may the same or different selected from nitrogen, sulfur and oxygen, in which the heterocycle is optionally substituted by (C$_1$-C$_4$)alkyl, phenyl or benzyl; and each occurrence of R$_b$ and R$_c$ is independently hydrogen, (C$_1$-C$_4$)alkyl, (C$_3$-C$_7$)cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by (C$_1$-C$_4$)alkyl, phenyl or benzyl; or said R$_b$ and R$_c$, together with the nitrogen atom to which they are bonded optionally form a 3- to 7-membered heterocycle which may be saturated or unsaturated comprising 1-4 heteroatoms, wherein the heterocycle is optionally substituted by (C$_1$-C$_4$)alkyl.

In yet another aspect, the present invention provides a method of inhibiting TLR-mediated immunostimulatory signaling, comprising contacting a cell expressing a TLR with an effective amount of at least one compound of Formula III,

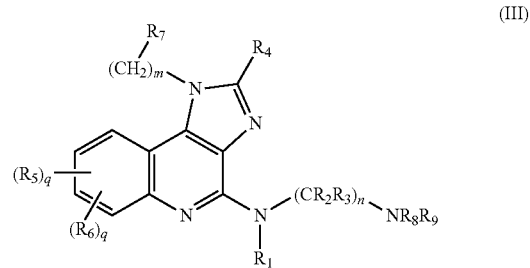

(III)

wherein each occurrence of R$_1$ is independently hydrogen, (C$_1$-C$_4$)alkyl, (C$_3$-C$_7$)cycloalkyl, (C$_2$-C$_6$)alkenyl, (C$_2$-C$_6$)alkynyl, aryl or a 5- to 7-membered heterocycle which may be saturated or unsaturated containing one to three heteroatoms which may the same or different selected from nitrogen, sulfur and oxygen, in which the heterocycle is optionally substituted by (C$_1$-C$_4$)alkyl, phenyl or benzyl;

each occurrence of R$_2$ and R$_3$ is independently hydrogen, (C$_1$-C$_4$)alkyl, (C$_3$-C$_7$)cycloalkyl, OH, (C$_1$-C$_4$)alkoxy, —(CH$_2$)$_p$NR$_a$R$_b$, or R$_2$ and R$_3$ together with the carbon atom to which they are bonded optionally form a (C$_3$-C$_6$) cycloalkyl;

R$_8$ is hydrogen, (C$_1$-C$_4$)alkyl, (C$_3$-C$_7$)cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by (C$_1$-C$_4$)alkyl, phenyl or benzyl;

R$_9$ is H, Me, Et, n-Pr, i-Pr, n-Bu, i-Bu, t-Bu, CH$_2$CMe$_3$, Ph, CH$_2$Ph, C(=O)R$_{12}$, (CH$_2$)$_p$OR$_a$, and (CH$_2$)$_p$NR$_b$R$_c$, wherein R$_{12}$ is (C$_1$-C$_4$)alkyl, phenyl, or a 5- to 7-membered heterocycle which may be saturated or unsaturated containing one to three heteroatoms which may the same or different selected from nitrogen, sulfur and oxygen, in which the heterocycle is optionally substituted by (C$_1$-C$_4$)alkyl, phenyl or benzyl; R$_a$, R$_b$ and R$_c$ are each independently hydrogen, or (C$_1$-C$_4$)alkyl, or R$_b$ and R$_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a 3- to 7-membered heterocycle which may be saturated or unsaturated comprising 1-4 heteroatoms, wherein the heterocycle is optionally substituted by $(C_1-C_4)$alkyl;

or $R_1$ and $R_8$ optionally form a 5- to 7-membered heterocycle which may be saturated or unsaturated comprising 2-4 heteroatoms, wherein the heterocycle is optionally substituted by $(C_1-C_4)$alkyl;

$R_4$ is hydrogen, halogen, cyano, nitro, $CF_3$, $OCF_3$, $(C_1-C_4)$alkyl, $(C_3-C_7)$cycloalkyl, $(C_2-C_6)$alkenyl, aryl, heterocycle, $OR_a$, —$CH_2OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

$R_5$ and $R_6$ are each independently hydrogen, halogen, cyano, nitro, $CF_3$, $OCF_3$, $(C_1-C_4)$alkyl, $(C_3-C_7)$cycloalkyl, $(C_2-C_6)$alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, alkaryl, alkylheterocyclic, or $NR_b(CH_2)_pNR_bR_c$, wherein the heterocycle is a 5- to 7-membered heterocyclic ring which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

L is alkyl or alkenyl containing from 2 to 10 carbon atoms;

$R_7$ is H, $(C_1-C_4)$alkyl, heteroaryl, —$O(CH_2)_pOR_a$, or $NR_{10}R_{11}$, wherein the heteroaryl is a 5- to 6-membered aromatic ring which may be saturated or unsaturated containing one to three heteroatoms which may the same or different selected from nitrogen, sulfur and oxygen, and the heteroaryl is optionally substituted by $(C_1-C_4)$alkyl;

m is an integer of 2-6;

n is an integer of 2-4;

each q is an integer of 1-2;

$R_{10}$ and $R_{11}$ are each independently hydrogen, $(C_1-C_4)$alkyl, $(C_3-C_7)$cycloalkyl, $(C_2-C_6)$alkenyl, aryl or $(C_1-C_4)$alkylaryl, or $R_{10}$ and $R_{11}$ together with the nitrogen atom to which they are bonded form a 3- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl;

each occurrence of $R_a$ is independently hydrogen, $(C_1-C_4)$alkyl, $(C_3-C_7)$cycloalkyl, $(C_2-C_6)$alkenyl, $(C_5-C_7)$cycloalkenyl, $(C_2-C_6)$alkynyl, aryl, or a 3- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl; and each occurrence of $R_b$ and $R_c$ is independently hydrogen, $(C_1-C_4)$alkyl, $(C_3-C_7)$cycloalkyl, aryl or a 5- to 7-membered heterocycle which may be saturated or unsaturated containing one to three heteroatoms which may the same or different selected from nitrogen, sulfur and oxygen, in which the heterocycle is optionally substituted by $(C_1-C_4)$alkyl, phenyl or benzyl; or said $R_b$ and $R_c$ together with the nitrogen atom to which they are bonded optionally form a 3- to 7-membered heterocycle which may be saturated or unsaturated comprising 1-4 heteroatoms, wherein the heterocycle is optionally substituted by $(C_1-C_4)$alkyl.

In some embodiments, the method of inhibiting TLR-mediated immunostimulatory signaling comprises contacting a cell expressing a TLR with an effective amount of a compound of Formulae I-III, as provided above, to inhibit TLR-mediated immunostimulatory signaling in response to a ligand for the TLR.

In some embodiments, the method of inhibiting TLR-mediated immunostimulatory signaling comprises contacting an immune cell expressing a functional TLR with (a) an effective amount of a TLR signal agonist to stimulate signaling by the TLR in absence of a imizazoquinoline composition, and (b) an effective amount of a imizazoquinoline composition having structural Formula I, II, or III, as described herein, to inhibit signaling by the TLR in response to the TLR signal agonist compared with the signaling by the TLR in response to the TLR signal agonist in absence of the imizazoquinoline composition.

In some specific embodiments, the imizazoquinoline composition is in the form a hydrate or pharmaceutically acceptable salt. In some specific embodiments, the method for inhibiting TLR-mediated immunostimulatory signaling is performed in vitro or in vivo.

In some embodiments, the TLR is TLR9 and the TLR signal agonist is a TLR9 signal agonist. In these embodiments, the method is a method of inhibiting intracellular signaling by TLR9 in response to a TLR9 signal agonist. The TLR signal agonist in one embodiment is CpG DNA, which can be an oligodeoxynucleotide (ODN). In some embodiments, CpG ODN is ODN 2006. In other embodiments, CpG ODN belongs to any class of CpG ODN, including A-class (e.g., ODN 2216), B-class (e.g., ODN 2006), or C-class (e.g., ODN 2395).

In one embodiment, the TLR signal agonist is an immune complex that includes a nucleic acid.

In some embodiments, the method as described herein are useful for altering TLR-mediated signaling. The methods are used to alter TLR-mediated signaling in response to a suitable TLR ligand or TLR signaling agonist. For example, the methods can be used to treat any of variety of conditions involving autoimmunity, inflammation, allergy, asthma, graft rejection, graft-versus host disease (GvHD), infection, sepsis, cancer, and immunodeficiency. Generally, methods useful in the treatment of conditions involving autoimmunity, inflammation, allergy, asthma, graft rejection, and GvHD will employ small molecules that inhibit TLR-mediated signaling in response to a suitable TLR ligand or TLR signaling agonist. Generally, methods useful in the treatment of conditions involving infection, cancer, and immunodeficiency will employ small molecules that augment TLR-mediated signaling in response to a suitable TLR ligand. In some embodiments, the methods are used to inhibit or promote TLR-mediated signaling in response to a TLR ligand or TLR signaling agonist. In some embodiments, the methods are used to inhibit TLR-mediated immunostimulatory signaling in response to a TLR ligand or TLR signaling agonist. In some embodiments, the methods are used to inhibit or promote TLR-mediated immunostimulation in a subject. In some embodiments, the methods are used to inhibit TLR-mediated immunostimulation in a subject. In some embodiments, the methods are used to inhibit an immunostimulatory nucleic acid-associated response in a subject.

In some embodiments, the method useful for altering TLR-mediated signaling uses small molecule compositions of compounds of Formulae I-III. The compositions of the invention are used to alter TLR-mediated signaling in response to a suitable TLR ligand or TLR signaling agonist. For example, the small molecules can be used in methods to treat any of a variety of conditions involving autoimmunity, inflammation, allergy, asthma, graft rejection, GvHD, infection, sepsis, cancer, and immunodeficiency. Generally, methods useful in the treatment of conditions involving autoimmunity, inflammation, allergy, asthma, graft rejection, and GvHD will employ small molecules that inhibit TLR-mediated signaling in response to a suitable TLR ligand or TLR signaling agonist. Generally, methods useful in the treatment of conditions involving infection, cancer, and immunodeficiency will employ small molecules that augment TLR-mediated signaling in response to a suitable TLR ligand. In some instances the molecules can be used in a method to inhibit or promote TLR-mediated signaling in response to a TLR ligand or TLR signaling agonist. In some instances the small molecules can be used in a method to inhibit TLR-mediated immunostimulatory signaling in response to a TLR ligand or TLR signaling agonist. In some embodiments, the small molecules are used in a method to inhibit or promote TLR-mediated immunostimulation in a subject. In some embodiments, the small molecules are used in a method to inhibit TLR-mediated immunostimulation in a subject. In some embodiments, the small molecules are used to inhibit an immunostimulatory nucleic acid-associated response in a subject.

Furthermore, the methods as described herein can be combined with administration of additional agents to achieve synergistic effect on TLR-mediated immunostimulation. More specifically, whereas the agents described herein have been discovered to affect TLRs directly and thus directly affect TLR-bearing cells, e.g., antigen-presenting cells (APCs), such agents can be used in conjunction with additional agents which affect non-APC immune cells, e.g., T lymphocytes (T cells). Such an approach effectively introduces an immunomodulatory intervention at two levels: innate immunity and acquired immunity. Since innate immunity is believed to initiate and support acquired immunity, the combination intervention is synergistic.

In yet another aspect, a method of inhibiting an immunostimulatory nucleic acid-associated response in a subject is provided. The method comprises administering to a subject in need of such treatment an effective amount of a compound of Formulae I-III, as provided above, to inhibit an immunostimulatory nucleic acid-associated response in the subject.

In one embodiment, the subject is otherwise free of symptoms calling for treatment with a compound of one of Formulae I-III.

In some embodiments, the subject being treated with the imizazoquinoline compounds as described herein has symptoms indicating a immune system disease. In other embodiments, the subject being treated with the imizazoquinoline compounds as described herein is free of any symptoms indicating a immune system disease.

In some embodiments, the TLR is TLR9. In some specific embodiments, the ligand for the TLR is an immunostimulatory nucleic acid. In other specific embodiments, the immunostimulatory nucleic acid is a CpG nucleic acid. In still other specific embodiments, the immunostimulatory nucleic acid a DNA containing immune complex.

In some embodiments, the TLR is TLR8. In some specific embodiments, the ligand for the TLR is a natural ligand for TLR8. In other specific embodiments, the ligand for the TLR is RNA. In still other specific embodiments, the ligand for the TLR is an immunostimulatory nucleic acid. In still other specific embodiments, the immunostimulatory nucleic acid is an RNA containing immune complex. In still other specific embodiments, the ligand for the TLR is an immunostimulatory imidazoquinoline. In still other specific embodiments, the ligand for the TLR is resiquimod (R848).

In some embodiments, the TLR is TLR7. In some specific embodiments, the ligand for the TLR is a natural ligand for TLR7. In other specific embodiments, the ligand for the TLR is an immunostimulatory nucleic acid. In one embodiment the ligand for the TLR is an RNA. In still other specific embodiments, the immunostimulatory nucleic acid is an RNA containing immune complex. In still other specific embodiments, the ligand for the TLR is an immunostimulatory imidazoquinoline. In still other specific embodiments, the ligand for the TLR is R848.

In some embodiments, the TLR is TLR3. In some specific embodiments, the ligand for the TLR is a double stranded RNA. In other specific embodiments, the ligand for the TLR is the immune complex as described herein. In still other specific embodiments, the ligand for the TLR is poly(I:C). In still other specific embodiments, the TLR is TLR9 and the TLR signal agonist is a TLR9 signal agonist. In still other specific embodiments, the TLR signal agonist is CpG DNA, which can be an oligodeoxynucleotide (ODN).

In some embodiments, the TLR signal agonist is an immune complex comprising a nucleic acid.

In yet another aspect, a method for inhibiting an immune response to an antigenic substance is provided. The method comprises contacting an immune cell expressing a functional Toll-like receptor with:

(a) an effective amount of an antigenic substance to stimulate an immune response to the antigenic substance in the absence of a imizazoquinoline composition, and (b) an effective amount of a imizazoquinoline composition having structural Formulae I-III, as defined above, to inhibit an immune response to the antigenic substance compared with the immune response to the antigenic substance in absence of the imizazoquinoline composition.

In some embodiments, the immune response is an innate immune response. In other embodiments, the immune response includes an adaptive immune response. In some specific embodiments, the imizazoquinoline composition is in the form a hydrate or pharmaceutically acceptable salt. In some specific embodiments, the method for inhibiting an immune response to an antigenic substance is performed in vitro or in vivo.

In some embodiments, the antigenic substance is an allergen. In other embodiments, the antigenic substance is an antigen that is or is derived from a microbial agent, including a bacterium, a virus, a fungus, or a parasite. In still other embodiments, the antigenic substance is a cancer antigen.

In certain embodiments, the functional TLR is naturally expressed by a cell. Non-limiting examples of cells expressing TLR include RPMI 8226 cell line.

In one embodiment, the cell naturally expresses functional TLR and is an isolated cell from human multiple myeloma cell line RPMI 8226 (ATCC CCL-155; American Type Culture Collection (ATCC), Manassas, Va.). This cell line was established from the peripheral blood of a 61 year old man at the time of diagnosis of multiple myeloma (IgG lambda type). Matsuoka Y., et al. (1967) *Proc. Soc. Exp. Biol. Med.* 125:1246-50. RPMI 8226 was previously reported as responsive to CpG nucleic acids as evidenced by the induction of IL-6 protein and IL-12p40 mRNA. Takeshita F., et al. (2000) *Eur. J. Immunol.* 30:108-16; Takeshita F., et al. (2000) *Eur. J. Immunol.* 30:1967-76. Takeshita, et al. used the cell line solely to study promoter constructs in order to identify transcription factor binding sites important for CpG nucleic acid signaling. It is now known that RPMI 8226 cells secrete a number of other chemokines and cytokines including IL-8, IL-10 and IP-10 in response to immunostimulatory nucleic acids. Because this cell line expresses TLR9, through which immunostimulatory nucleic acids such as for example CpG nucleic acids mediate their effects, it is a suitable cell line for use in the methods of the invention relating to CpG nucleic acids as reference and test compounds, as well as to other TLR9 ligands.

Similar to peripheral blood mononuclear cells (PBMCs), the RPMI 8226 cell line has been observed to upregulate its cell surface expression of markers such as CD71, CD86 and HLA-DR in response to CpG nucleic acid exposure. This has been observed by flow cytometric analysis of the cell line. Accordingly, the methods provided herein can be structured to use appropriately selected cell surface marker expression as a readout, in addition to or in place of chemokine or cytokine production or other readouts described elsewhere herein.

The RPMI 8226 cell line has also been found to respond to certain small molecules including imidazoquinoline compounds. For example, incubation of RPMI 8226 cells with the imidazoquinoline compound R848 (resiquimod) induces IL-8, IL-10, and IP-10 production. It has recently been reported that R848 mediates its immunostimulatory effects through TLR7 and TLR8. The ability of RPMI 8226 to respond to R848 suggests that the RPMI 8226 cell line also expresses TLR7, as previously reported for normal human B cells.

The RPMI cell line can be used in unmodified form or in a modified form. In one embodiment, the RPMI 8226 cell is transfected with a reporter construct. Preferably, the cell is stably transfected with the reporter construct. The reporter construct generally includes a promoter, a coding sequence and a polyadenylation signal. The coding sequence can include a reporter sequence selected from the group consisting of an enzyme (e.g., luciferase, alkaline phosphatase, beta-galactosidase, chloramphenicol acetyltransferase (CAT), secreted alkaline phosphatase, etc.), a bioluminescence marker (e.g., green fluorescent protein (GFP, U.S. Pat. No. 5,491,084), etc.), a surface-expressed molecule (e.g., CD25), a secreted molecule (e.g., IL-8, IL-12 p40, TNF-α, etc.), and other detectable protein products known to those of skill in the art. Preferably, the coding sequence encodes a protein having a level or an activity that is quantifiable.

In certain embodiments, the functional TLR is artificially expressed (including over-expressed) by a cell, for example by introduction into the cell of an expression vector bearing a coding sequence for the functional TLR wherein the coding sequence is operably linked to a gene expression sequence. As used herein, a coding sequence and the gene expression sequence are said to be operably linked when they are covalently linked in such a way as to place the expression or transcription and/or translation of the coding sequence under the influence or control of the gene expression sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding sequence if the gene expression sequence were capable of effecting transcription of that coding sequence such that the resulting transcript is translated into the desired protein or polypeptide.

In some embodiments, a coding sequence refers to a nucleic acid sequence coding for a functional TLR. In some embodiments, a coding sequence refers to a nucleic acid sequence coding for a reporter.

A cell that artificially expresses a functional TLR can be a cell that does not express the functional TLR but for the TLR expression vector. For example, human 293 fibroblasts (ATCC CRL-1573) do not express TLR3, TLR7, TLR8, or TLR9. As described in the examples below, such cells can be transiently or stably transfected with suitable expression vector (or vectors) so as to yield cells that do express TLR3, TLR7, TLR8, TLR9, or any combination thereof. Alternatively, a cell that artificially expresses a functional TLR can be a cell that expresses the functional TLR at a significantly higher level with the TLR expression vector than it does without the TLR expression vector.

For use in the methods of the instant invention, a cell that artificially expresses a functional TLR is preferably a stably transfected cell that expresses the functional TLR. Such a cell can also be stably transfected with a suitable reporter construct.

Assays for Effectiveness

The methods of the invention can be assessed using any of a number of possible readout systems based upon a TLR/IL-1R signal transduction pathway. In some embodiments, the readout for the method is based on the use of native genes or, alternatively, transfected or otherwise artificially introduced reporter gene constructs which are responsive to the TLR/IL-1R signal transduction pathway involving MyD88, TRAF, p38, and/or ERK. Häcker H., et al. (1999) *EMBO. J.* 18:6973-82. These pathways activate kinases including κB kinase complex and c-Jun N-terminal kinases. Thus reporter genes and reporter gene constructs particularly useful for the assays include, e.g., a reporter gene operatively linked to a promoter sensitive to NF-κB. Examples of such promoters include, without limitation, those for NF-κB, IL-1β, IL-6, IL-8, IL-12 p40, IP-10, CD80, CD86, and TNF-α. The reporter gene operatively linked to the TLR-sensitive promoter can include, without limitation, an enzyme (e.g., luciferase, alkaline phosphatase, β-galactosidase, chloramphenicol acetyltransferase (CAT), etc.), a bioluminescence marker (e.g., green-fluorescent protein (GFP, e.g., U.S. Pat. No. 5,491,084), blue fluorescent protein (BFP, e.g., U.S. Pat. No. 6,486,382), etc.), a surface-expressed molecule (e.g., CD25, CD80, CD86), and a secreted molecule (e.g., IL-1, IL-6, IL-8, IL-12 p40, TNF-α). In certain embodiments the reporter is selected from IL-8, TNF-α, NF-κB-luciferase (NF-κB-luc; Häcker H., et al. (1999) *EMBO. J.* 18:6973-82), IL-12 p40-luc (Murphy T. L., et al. (1995) *Mol. Cell. Biol.* 15:5258-67), and TNF-luc (Häcker H., et al. (1999) *EMBO. J.* 18:6973-82). In assays relying on enzyme activity readout, substrate can be supplied as part of the assay, and detection can involve measurement of chemiluminescence, fluorescence, color development, incorporation of radioactive label, drug resistance, or other marker of enzyme activity. For assays relying on surface expression of a molecule, detection can be accomplished using flow cytometry (FACS) analysis or functional assays. Secreted molecules can be assayed using enzyme-linked immunosorbent assay (ELISA) or bioassays. Many of these and other suitable readout systems are well known in the art and are commercially available.

Reporter Constructs

A cell expressing a functional TLR and useful for the methods of the invention has, in some embodiments, an expression vector including an isolated nucleic acid which encodes a reporter construct useful for detecting TLR signaling. The expression vector including an isolated nucleic acid which encodes a reporter construct useful for detecting TLR signaling can include a reporter gene under control of a promoter response element (enhancer element). In some embodiments, the promoter response element is associated with a minimal promoter responsive to a transcription factor believed by the applicant to be activated as a consequence of TLR signaling. Examples of such minimal promoters include, without limitation, promoters for the following genes: AP-1, NF-κB, ATF2, IRF3, and IRF7. These minimal promoters contain corresponding promoter response elements sensitive to AP-1, NF-κB, ATF2, IRF3, and IRF7, respectively. In other embodiments the expression vector including an isolated nucleic acid which encodes a reporter construct useful for detecting TLR signaling can include a gene under control of a promoter response element selected from response elements sensitive to IL-6, IL-8, IL-12 p40 subunit, a type I IFN, RANTES, TNF, IP-10, I-TAC, and interferon-stimulated response element (ISRE). The promoter response element generally will be present in multiple copies, e.g., as tandem repeats. For example, in one reporter construct, coding sequence for luciferase is under control of an upstream 6× tandem repeat of NF-κB response element. In some embodiments, an ISRE-luciferase reporter construct useful in the invention is available from Stratagene (catalog no. 219092) and includes a 5×ISRE tandem repeat joined to a TATA box upstream of a luciferase reporter gene. As described herein, the reporter itself can be any gene product suitable for detection by methods recognized in the art. Such methods for detection can include, for example, measurement of spontaneous or stimulated light emission, enzyme activity, expression of a soluble molecule, expression of a cell surface molecule, etc.

Readouts typically involve usual elements of Toll/IL-1R signaling, e.g., MyD88, TRAF, and IRAK molecules, although in the case of TLR3 the role of MyD88 is less clear than for other TLR family members. As described herein, such responses include the induction of a gene under control of a specific promoter such as a NF-κB promoter, increases in particular cytokine levels, increases in particular chemokine levels, etc. The gene under the control of the NF-κB promoter can be a gene which naturally includes an NF-κB promoter or it can be a gene in a construct in which an NF-κB promoter has been inserted. Genes and constructs which include the NF-κB promoter include but are not limited to IL-8, IL-12 p40, NF-κB-luc, IL-12 p40-luc, and TNF-luc.

Increases in cytokine levels can result from increased production, increased stability, increased secretion, or any combination of the forgoing, of the cytokine in response to the TLR-mediated signaling. Cytokines generally include, without limitation, IL-1, IL-2, IL-3, IL-4, IL-5, IL-6, IL-7, IL-10, IL-11, IL-12, IL-13, IL-15, IL-18, IFN-α, IFN-β, IFN-γ, TNF-α, GM-CSF, G-CSF, M-CSF. Th1 cytokines include but are not limited to IL-2, IFN-γ, and IL-12. Th2 cytokines include but are not limited to IL-4, IL-5, and IL-10.

Increases in chemokine levels can result from increased production, increased stability, increased secretion, or any combination of the forgoing, of the chemokine in response to the TLR-mediated signaling. Chemokines of particular significance in the invention include but are not limited to CCL5 (RANTES), CXCL9 (Mig), CXCL10 (IP-10), and CXCL11 (1-TAC), IL-8, and MCP-1.

ABBREVIATIONS

| | |
|---|---|
| ACN | Acetonitrile |
| EA | Ethyl acetate |
| DMF | Dimethyl formamide |
| PE | Petroleum ether |
| DCM | Dichloromethane |
| THF | Tetrahydrofuran |
| HOBT | 1-Hydroxybenzotriazole |
| EDCI | 1-Ethyl-3-(3-dimethylaminopropyl)carbodiimide |
| HBTU | 2-(1H-Benzotriazole-1-yl)-1,1,3,3-tetramethyluronium hexafluorophosphate |
| HATU | N-[(dimethylamino)(3H-1,2,3-triazolelo(4,4-b)pyridin-3-yloxy)methylene]-N-methylmethaneaminium hexafluorophosphate |
| PyBOP | 1H-Benzotriazol-1-yloxytripyrrolidinophosphoniumhexafluorophosphate |
| BOPCl | Bis(2-oxo-3-oxazolidinyl)phosphinic chloride |
| BOP | Benzotriazol-1-yloxytris(diethylamino)phosphonium hexafluorophospahte |
| TEA | Triethylamine |
| DIPEA | Diisopropylethylamine |
| DMAP | 4-Dimethylaminopyridine |
| PCC | Pyridinium chlorochromate |
| PDC | Pyridinium dichromate |
| NBS | N-bromosuccinimide |
| NCS | N-chlorosuccinimide |
| NIS | N-iodosuccinimide |
| 9-BBN | 9-Borabicyclo[3.3.1]nonane |
| TsOH | p-Toluenesulfonic acid |
| TFA | Trifluoroacetamide |
| CDI | Carbonyldiimidazole |

Methods of Preparation

Following are general synthetic schemes for manufacturing compounds of the present invention. These schemes are illustrative and are not meant to limit the possible techniques one skilled in the art any use to manufacture compounds disclosed herein. Different methods will be evident to those skilled in the art. Additionally, the various steps in the synthesis may be performed in an alternate sequence or order to give the desired compound(s). All documents cited herein are incorporated herein by reference in their entirety. For example, the following reactions are illustrations but not limitations of the preparation of some of the starting materials and examples used herein.

Schemes 1-4 describe various methods for the synthesis of intermediates that may be used to prepare compounds of the present invention. Various modifications to these methods may be envisioned by those skilled in the art to achieve similar results to that of the inventors given below.

Imizazoquinoline compound of Formula I may be prepared as shown in Scheme 1.

Scheme 1

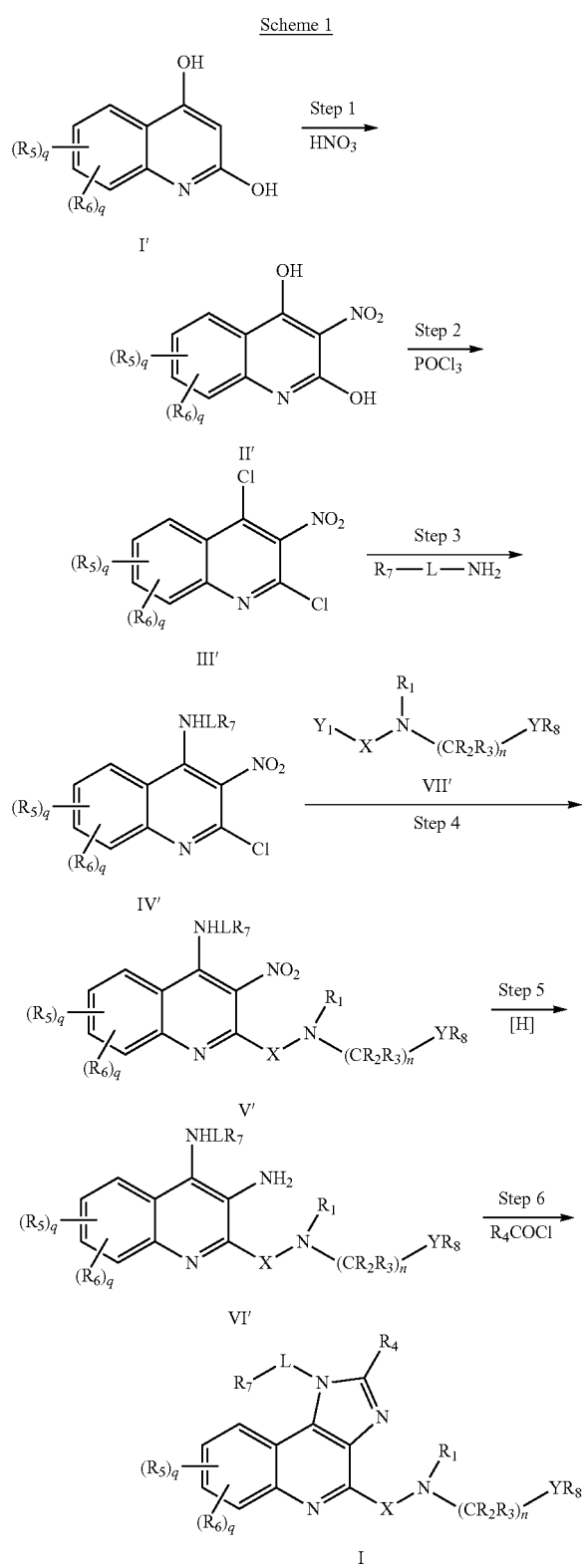

Step 1
Quinoline I' may be substituted by a nitro group using nitric acid to afford nitro quinoline II'. Suitable solvent for this reaction includes nitric acid (concentrated nitric acid or fuming nitric acid (90%)), or acetic acid and propionic acid in conjunction with nitric acid.

Step 2
Nitro quinoline II' can be treated with $POCl_3$ to afford dichloro quinoline III'. $POCl_3$ can be used neat without solvent or additional suitable solvent can be used, including chloroform, methylene chloride, toluene and chlorobenzene.

Step 3
The chloride at the para position to the quinoline nitrogen of compound III' is substituted by $R_7LNH_2$ to afford compound IV'. Suitable solvent for this reaction includes methylene chloride, chloroform, 2-propanol, n-butanol, and toluene.

Step 4
Compound IV' can be coupled nucleophile VII' to afford the substituted nitro quinoline V'. When X is not absent, $Y_1$ can be a boronic acid $—B(OH)_2$ or ester $—B(OR)_2$ or $Y_1$ may be a tin derivative. The reaction may be carried out optionally using a catalyst such as Pd(0) in the presence of a base, such as potassium carbonate. If X is absent, $Y_1$ can be H. Suitable solvent for this reaction includes chloroform, methylene chloride, toluene, 2-propanol and n-butanol, and tetrahydrofuran.

Step 5
The nitro group of compound V' can be reduced to result in aminoquinoline VI'. Suitable reducing agents include $H_2$, $SnCl_2$, and any other reducing agents known in the art. Suitable solvent for this reaction includes chloroform, methylene chloride, toluene, methanol, ethanol, 2-propanol, and tetrahydrofuran.

Step 6
Aminoquinoline VI' can be cyclized using $R_4COCl$ to afford compound of Formula I. Suitable solvent for this reaction includes chloroform, methylene chloride, toluene, and tetrahydrofuran.

Alternatively, Imidazole quinoline compound of Formula I may be prepared as shown in Scheme 2.

Scheme 2

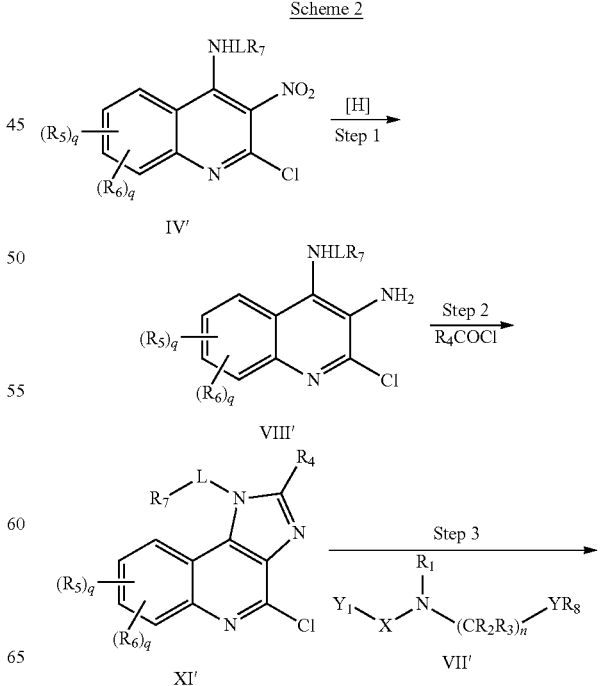

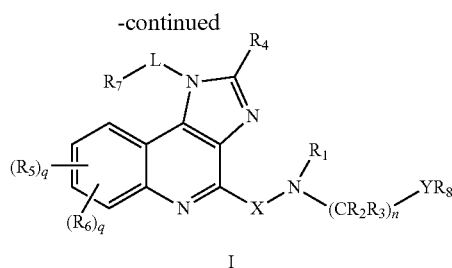

Step 1

The nitro group of compound IV' can be reduced to result in animoquinoline VIII'. Suitable reducing agents include $H_2$, $SnCl_2$, and any other reducing agents known in the art. Suitable solvent for this reaction includes chloroform, methylene chloride, toluene, and tetrahydrofuran.

Step 2

Aminoquinoline VIII' can be cyclized using $R_4COCl$ to afford compound XI'. Suitable solvent for this reaction includes chloroform, methylene chloride, toluene, and tetrahydrofuran.

Step 3

Compound XI' can be coupled nucleophile VII' to afford the substituted nitro quinoline V'. When X is not absent, $Y_1$ can be a boronic acid —$B(OH)_2$ or ester —$B(OR)_2$ or $Y_1$ may be a tin derivative. The reaction may be carried out optionally using a catalyst such as Pd(0) in the presence of a base, such as potassium carbonate. If X is absent, $Y_1$ can be H. Suitable solvent for this reaction includes chloroform, methylene chloride, toluene, 2-propanol and n-butanol, and tetrahydrofuran.

In addition, other compounds of formulae I-III may be prepared by the procedures generally known to those skilled in the art. In particular, the following examples provide additional methods for preparing compounds of this invention.

The invention will now be further described by the working examples as below, which are preferred embodiments of the invention. These examples are illustrated rather than limiting, and it is to be understood that there may be other embodiments that fall within the spirit and scope of the invention as defined by the claims appended hereto.

Pharmaceutical Compositions

This invention also provides a pharmaceutical composition comprising at least one of the compounds as described herein or a pharmaceutically-acceptable salt or solvate thereof, and a pharmaceutically-acceptable carrier.

In yet another aspect, a pharmaceutical composition is described, comprising at least one compound of Formula I, or a pharmaceutically acceptable salt thereof, and a pharmaceutically-acceptable carrier or diluent,

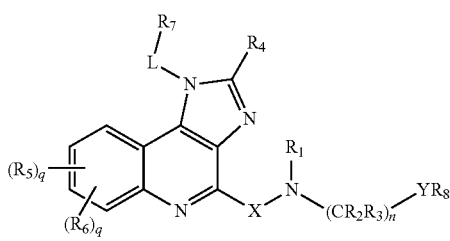

wherein

X is absent or is an alkyl, cycloalkyl, aryl, aralkyl, or heterocycle;

each occurrence of $R_1$ is independently hydrogen, alkyl, cycloalkyl, alkenyl, cycloalkenyl, alkynyl, heterocycle, or aryl;

each occurrence of $R_2$ and $R_3$ is independently hydrogen, alkyl, cycloalkyl, OH, alkoxy, —$(CH_2)_pNR_aR_b$, or $R_2$ and $R_3$ together with the carbon atom to which they are bonded optionally form a ($C_3$-$C_7$)cycloalkyl;

n is an integer of 2-4;

each q is an integer of 1-2;

Y is $NR_9$ or O;

$R_8$ is hydrogen, alkyl, cycloalkyl, monocyclic heterocycle, or aryl;

$R_9$ is H, Me, Et, n-Pr, i-Pr, n-Bu, i-Bu, t-Bu, $CH_2CMe_3$, Ph, $CH_2Ph$, C(=O)$R_{12}$, $(CH_2)_pOR_a$, and $(CH_2)_pNR_bR_c$, wherein $R_{12}$ is alkyl, phenyl, or heterocycle; $R_a$, $R_b$ and $R_c$ are each independently hydrogen, or ($C_1$-$C_4$)alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4;

or said $R_8$ and $R_9$ together with the nitrogen atom to which they are bonded optionally form a heterocycle comprising 1-4 heteroatoms, wherein the heterocycle is optionally substituted by ($C_1$-$C_4$)alkyl;

or $R_1$ and $R_8$ optionally form a heterocycle comprising 2-4 heteroatoms, wherein the heterocycle is optionally substituted by ($C_1$-$C_4$)alkyl;

$R_4$ is hydrogen, halogen, cyano, nitro, $CF_3$, $OCF_3$, alkyl, cycloalkyl, alkenyl, aryl, heterocycle, $OR_a$, —$CH_2OR_a$, $SR_a$, S(=O)$R_a$, S(=O)$_2R_a$, $NR_bR_c$, S(=O)$_2NR_bR_c$, C(=O)$OR_a$, C(=O)$R_a$, C(=O)$NR_bR_c$, OC(=O)$R_a$, OC(=O)$NR_bR_c$, $NR_bC$(=O)$OR_a$, $NR_bC$(=O)$R_a$;

$R_5$ and $R_6$ are each independently hydrogen, halogen, cyano, nitro, $CF_3$, $OCF_3$, alkyl, cycloalkyl, alkenyl, aryl, heterocycle, $OR_a$, $SR_a$, S(=O)$R_a$, S(=O)$_2R_a$, $NR_bR_c$, S(=O)$_2NR_bR_c$, C(=O)$OR_a$, C(=O)$R_a$, C(=O)$NR_bR_c$, OC(=O)$R_a$, OC(=O)$NR_bR_c$, $NR_bC$(=O)$OR_a$, $NR_bC$(=O)$R_a$, alkaryl, alkylheterocyclic, or $NR_b(CH_2)_pNR_bR_c$;

or said $R_5$ and $R_6$ together with the carbon atoms to which they are bonded optionally form a heterocycle comprising 1-4 heteroatoms, wherein the heterocycle is optionally substituted by ($C_1$-$C_4$)alkyl;

L is absent or is alkyl or alkenyl containing from 2 to 10 carbon atoms;

$R_7$ is H, alkyl, heteroaryl, —$O(CH_2)_pOR_a$, or $NR_{10}R_{11}$, wherein the heteroaryl are optionally substituted by ($C_1$-$C_4$) alkyl;

$R_{10}$ and $R_{11}$ are each independently hydrogen, alkyl, cycloalkyl, alkenyl, aryl or alkylaryl, or $R_{10}$ and $R_{11}$ together with the nitrogen atom to which they are bonded form a heterocycle;

p is an integer of 0, 1, 2, 3, 4, 5, or 6;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle comprising 1-4 heteroatoms, wherein the heterocycle is optionally substituted by ($C_1$-$C_4$) alkyl.

In yet another aspect, a pharmaceutical composition is described, comprising at least one compound of Formula II as described herein, or a pharmaceutically acceptable salt thereof, and a pharmaceutically-acceptable carrier or diluent. In yet another aspect, a pharmaceutical composition is described, comprising at least one compound of Formula III as described herein, or a pharmaceutically acceptable salt thereof, and a pharmaceutically-acceptable carrier or diluent.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The term "carrier" denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency.

As set out above, certain embodiments of the present pharmaceutical agents may be provided in the form of pharmaceutically-acceptable salts. The term "pharmaceutically-acceptable salt", in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge, et al., (1977) "Pharmaceutical Salts", *J. Pharm. Sci.* 66:1-19.)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, butionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra.)

Wetting agents, emulsifiers and lubricants, such as sodium lauryl sulfate, magnesium stearate, and polyethylene oxide-polybutylene oxide copolymer as well as coloring agents, release agents, coating agents, sweetening, flavoring and perfuming agents, preservatives and antioxidants can also be present in the compositions.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polybutylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxybutylmethyl cellulose), lubricant, inert diluent, preservative, disintegrant (for example, sodium starch glycolate or cross-linked sodium carboxymethyl cellulose), surface-active or dispersing agent. Molded tablets, may be, made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxybutylmethyl cellulose in varying butortions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if apbutriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxybutyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention.

Formulations of the present invention which are suitable for vaginal administration also include pessaries, tampons, creams, gels, pastes, foams or spray formulations containing such carriers as are known in the art to be apbutriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or butellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary butellants, such as chlorofluorohydrocarbons and volatile unsubstituted hydrocarbons, such as butane and butane.

Transdermal patches have the added advantage of providing controlled delivery of a compound of the present invention to the body. Such dosage forms can be made by dissolving, or dispersing the pharmaceutical agents in the butter medium. Absorption enhancers can also be used to increase the flux of the pharmaceutical agents of the invention across the skin. The rate of such flux can be controlled, by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle. One strategy for depot injections includes the use of polyethylene oxide-polybutylene oxide copolymers wherein the vehicle is fluid at room temperature and solidifies at body temperature.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions, which are compatible with body tissue.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another anti-inflammatory or immunosuppressant agent); such as but not limited to NSAIDS, DMARDS, Steroids, or biologics such as antibody therapies) or they may achieve different effects (e.g., control of any adverse effects).

The compounds of the invention may be administered intravenously, intramuscularly, intraperitoneally, subcutaneously, topically, orally, or by other acceptable means. The compounds may be used to treat arthritic conditions in mammals (i.e., humans, livestock, and domestic animals), birds, lizards, and any other organism, which can tolerate the compounds.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Administration to a Subject

Some aspects of the invention involve administering an effective amount of a composition to a subject to achieve a specific outcome. The small molecule compositions useful according to the methods of the present invention thus can be formulated in any manner suitable for pharmaceutical use.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound can be administered to a subject by any mode allowing the compound to be taken up by the appropriate target cells. "Administering" the pharmaceutical composition of the present invention can be accomplished by any means known to the skilled artisan. Specific routes of administration include but are not limited to oral, transdermal (e.g., via a patch), parenteral injection (subcutaneous, intradermal, intramuscular, intravenous, intraperitoneal, intrathecal, etc.), or mucosal (intranasal, intratracheal, inhalation, intrarectal, intravaginal, etc.). An injection can be in a bolus or a continuous infusion.

For example the pharmaceutical compositions according to the invention are often administered by intravenous, intramuscular, or other parenteral means, or by biolistic "gene-gun" application to the epidermis. They can also be administered by intranasal application, inhalation, topically, orally, or as implants, and even rectal or vaginal use is possible. Suitable liquid or solid pharmaceutical preparation forms are, for example, aqueous or saline solutions for injection or inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer R (1990) *Science* 249:1527-33, which is incorporated herein by reference.

The concentration of compounds included in compositions used in the methods of the invention can range from about 1 nM to about 100 µM. Effective doses are believed to range from about 10 picomole/kg to about 100 micromole/kg.

The pharmaceutical compositions are preferably prepared and administered in dose units. Liquid dose units are vials or ampoules for injection or other parenteral administration. Solid dose units are tablets, capsules, powders, and suppositories. For treatment of a patient, depending on activity of the compound, manner of administration, purpose of the administration (i.e., prophylactic or therapeutic), nature and severity of the disorder, age and body weight of the patient, different doses may be necessary. The administration of a given dose can be carried out both by single administration in the form of an individual dose unit or else several smaller dose units. Repeated and multiple administration of doses at specific intervals of days, weeks, or months apart are also contemplated by the invention.

The compositions can be administered per se (neat) or in the form of a pharmaceutically acceptable salt. When used in medicine the salts should be pharmaceutically acceptable, but non-pharmaceutically acceptable salts can conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicyclic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Compositions suitable for parenteral administration conveniently include sterile aqueous preparations, which can be isotonic with the blood of the recipient. Among the acceptable vehicles and solvents are water, Ringer's solution, phosphate buffered saline, and isotonic sodium chloride solution. In addition, sterile, fixed oils are conventionally employed as a solvent or suspending medium. For this purpose any bland fixed mineral or non-mineral oil may be employed including synthetic mono- or diglycerides. In addition, fatty acids such as oleic acid find use in the preparation of injectables. Carrier formulations suitable for subcutaneous, intramuscular, intraperitoneal, intravenous, etc. administrations can be found in *Remington's Pharmaceutical Sciences*, Mack Publishing Company, Easton, Pa.

The compounds useful in the invention can be delivered in mixtures of more than two such compounds. A mixture can further include one or more adjuvants in addition to the combination of compounds.

A variety of administration routes is available. The particular mode selected will depend, of course, upon the particular compound selected, the age and general health status of the subject, the particular condition being treated, and the dosage required for therapeutic efficacy. The methods of this invention, generally speaking, can be practiced using any mode of administration that is medically acceptable, meaning any mode that produces effective levels of response without causing clinically unacceptable adverse effects. Preferred modes of administration are discussed above.

The compositions can conveniently be presented in unit dosage form and can be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and equivalents thereof.

EXAMPLES

Example 1. Compound 3 was Prepared by Using Procedures Below

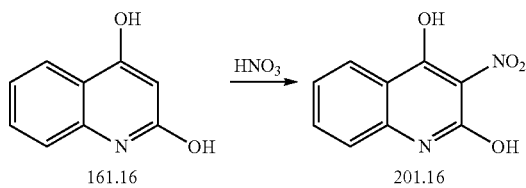 [SMILES: Oc1cc(O)c2ccccc2n1 ; "HNO3" ; O=[N+]([O-])c1c(O)nc2ccccc2c1O]

A mixture of 2,4-quinolinediol (20 gm, 0.124 moles) in acetic acid (120 mL) was stirred as concentrated nitric acid (32 mL) was added in a single portion. A thick mass resulted. This was heated in an oil bath set at 105° C. After a few minutes the mass liquefied allowing the mixture to be stirred. After a clear brown solution formed, the reaction was allowed to proceed at 105° C. for 10 minutes. The heating bath was removed and water (200 mL) was added with stirring causing a slurry to form. After stirring for 30 minutes, the solid was isolated by filtration and was washed well with water. The solid was then dried under vacuum. The yield of the nitro compound was 23 gm (89.9%) as a yellow solid.

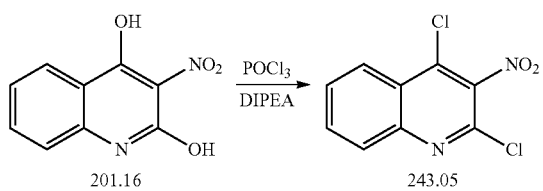

A mixture of 2,4-dihydroxy-3-nitroquinoline (23 gm, 0.112 moles), and diisopropylethylamine (22.3 gm, 30 mL, 0.172 moles) was stirred in toluene (100 mL) and cooled in an ice bath. To this mixture was added phosphorous oxychloride (67.4 gm, 41 mL, 0.440 moles) through a dropping funnel over 15 minutes. Once the addition was complete, the brown solution was heated at reflux for 10 hours. After cooling, the reaction solution was stirred in ice and water (800 gm) and a solution of potassium carbonate (80 gm) in water (200 mL) was slowly and cautiously (foaming) added. After stirring for 60 minutes, ethyl acetate (200 mL was added and the organic phase was isolated. The aqueous was extracted with ethyl acetate (200 mL) and these extracts were combined with the original organic phase. The combined organic solutions were washed with 20% potassium carbonate solution before being dried over magnesium sulfate. After filtration, the solvents were removed under vacuum. The residual brown solid was recrystallized from 2-propanol. After filtration and washing with 2-propanol followed by hexane, the brown solid was dried under vacuum. The yield was 15.5 gm (56.9%).

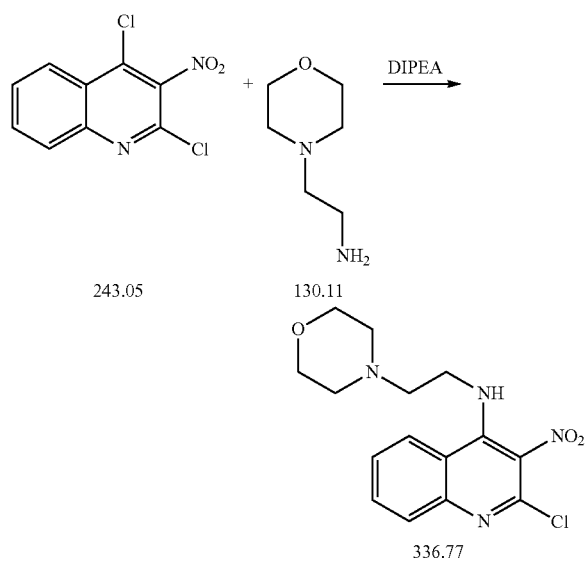

A solution of 2,4-dichloro-3-nitroquinoline (4.86 gm, $2.0 \times 10^{-2}$ moles) in tetrahydrofuran (50 mL) was stirred as diisopropylethylamine (2.84 gm, 3.83 mL, $2.2 \times 10^{-2}$ moles) and N-2-aminoethylmorpholine (2.86 gm, 2.89 mL, $2.2 \times 10^{-2}$ moles) were added. This solution was stirred at room temperature overnight. The yellow reaction mixture was diluted with more 2-methyltetrahydrofuran (50 mL) and this was washed with water (100 mL) followed by brine (50 mL). After being dried over magnesium sulfate, the solution was filtered and the solvent was removed under reduced pressure. The oily residue was stirred with diethyl ether (25 mL) and this was cooled on ice causing the product to crystallize. The solid yellow product was isolated by filtration, washed with ether and dried. The yield was 3.75 gm (55.7%).

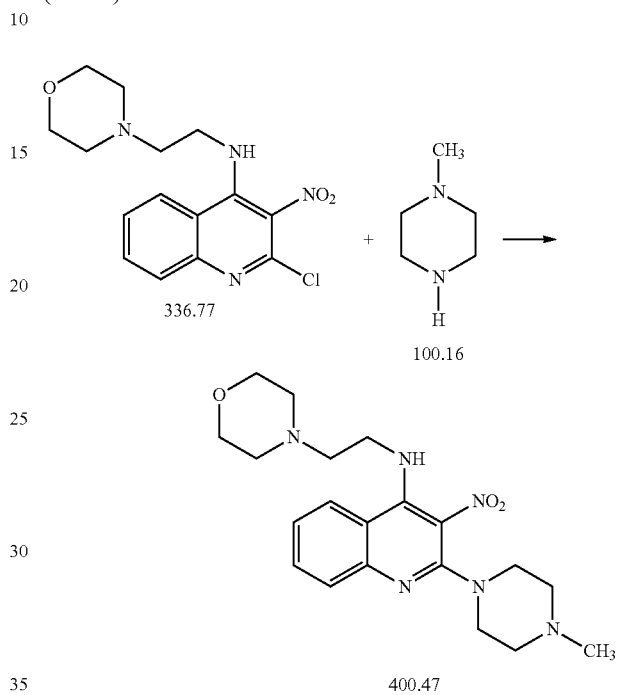

A solution of the chloronitroquinoline (3.65 gm, $1.08 \times 10^{-2}$ moles) in N-methylpyrrolidinone (5 mL) was treated with N-methylpiperazine (1.5 gm, 1.66 mL, $1.5 \times 10^{-2}$ moles) and diisopropylethylamine (4.19 gm, 5.67 mL, $3.24 \times 10^{-2}$ moles). This mixture was heated in a pressure tube at 125° C. for 2 hours. TLC (silica, 10% methanol in methylene chloride showed complete conversion of the starting material (Rf=0.63) to a single product (Rf=0.34). After cooling, the mixture was diluted with ethyl acetate (100 mL) and this solution was washed with water (2×100 mL) and then brine (50 mL). The combined aqueous washes were back extracted with ethyl acetate (50 mL) and this extract was washed with brine before being added to the original organic solution. The solvent was removed under vacuum and the dark orange residual material was dried under vacuum.

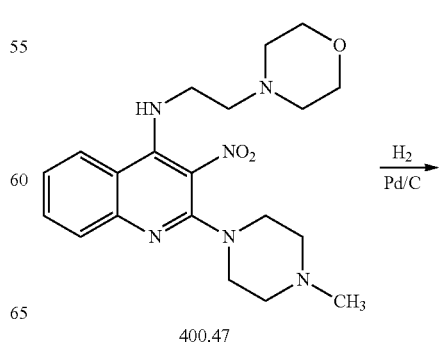

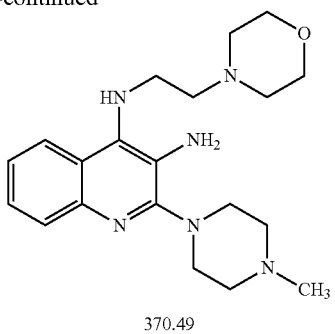

370.49

The crude nitro compound from above (1.08×10⁻² moles) was dissolved in methanol (100 mL) and was hydrogenated over 10% palladium on carbon at 40 psi of hydrogen on a Parr hydrogenator. Once hydrogen consumption stopped (about 15 minutes) the Parr bottle was flushed with argon and the clear, colorless solution was filtered through a pad of Celite to remove the catalyst. The methanol was removed under vacuum and dry toluene (50 mL) was added. This too was removed under vacuum to remove traces of methanol and the residue was re-dissolved in toluene (50 mL).

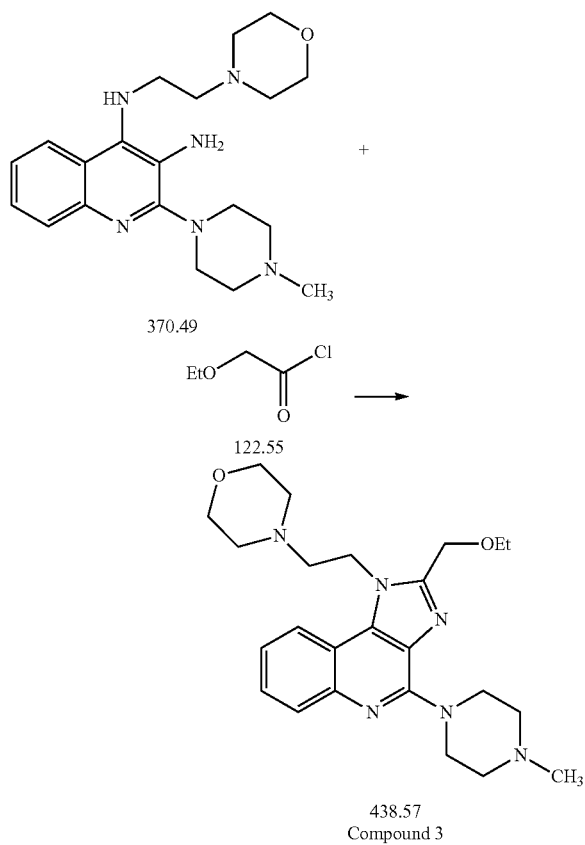

Ethoxyacetic acid (1.09 gm, 0.992 mL, 1.05×10⁻² moles) and thionyl chloride (1.25 gm, 0.766 mL, 1.05×10⁻² moles) were combined in toluene (10 mL) and this solution was heated at 100° C. for 2 hours. After this time, HCl evolution had ceased and argon was passed through the solution for 15 minutes to remove HCl and SO₂. This solution was added to the toluene solution from above causing a sticky precipitate to form. This mixture was heated at 100° C. for one hour. The precipitate had not dissolved so the toluene was removed under vacuum and was replaced with DMF (15 mL). To the resulting solution was added ethoxyacetic acid (0.50 mL) and the solution was heated at 100° C. overnight. After cooling, the solution was diluted with ethyl acetate (200 mL) and this solution was washed with 5% potassium carbonate (2×50 mL). The ethyl acetate solution was then extracted with 5% HCl solution (2×50 mL). The acidic extracts were washed with ethyl acetate (50 mL) and were then made basic by the addition of solid potassium carbonate. The precipitated oil was extracted into methylene chloride (200 mL) and the solution was dried over magnesium sulfate, filtered and evaporated under vacuum to provide a brown solid. This was recrystallized from ethyl acetate to give 1.3 gm (28%) of the imidazoquinoline as a tan solid. LC/MS of Compound 3: molecular ion at 439.37 (M+1), which is consistent with structure.

NMR of Compound 3 is as follows, which is consistent with the structure:

| Δ (PPM) | # protons | multiplicity |
| --- | --- | --- |
| 1.26 | 3 | triplet |
| 2.40 | 3 | singlet |
| 2.60 | 4 | triplet |
| 2.70 | 4 | triplet |
| 2.85 | 2 | triplet |
| 3.65 | 2 | quartet |
| 3.70 | 4 | triplet |
| 4.30 | 4 | broad triplet |
| 4.75 | 2 | triplet |
| 4.85 | 2 | singlet |
| 7.30 | 1 | triplet |
| 7.60 | 1 | triplet |
| 7.80 | 1 | doublet |
| 8.10 | 1 | doublet |

Example 2 (Compound 54)

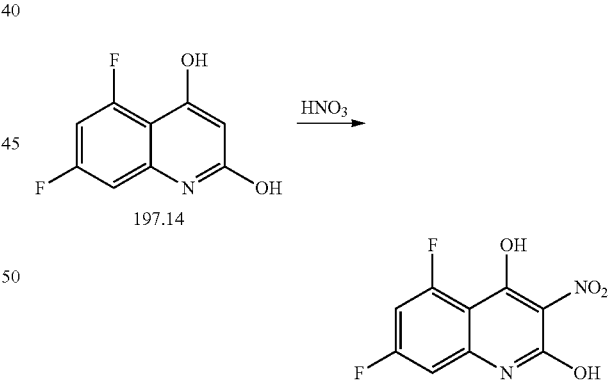

A mixture of 2,4-dihydroxy, 5,7-difluoroquinoline (24.4 gm, 0.124 moles) in acetic acid (120 mL) is stirred as concentrated nitric acid (32 mL) is added in a single portion. A thick mass results. This is heated in an oil bath set at 105° C. After a few minutes the mass liquefies allowing the mixture to be stirred. After a clear brown solution forms, the reaction is allowed to proceed at 105° C. for 10 minutes. The heating bath is removed and water (200 mL) is added with stirring causing a slurry to form. After stirring for 30 minutes, the solid is isolated by filtration and is washed well with water. The solid is then dried under vacuum. The yield of the nitro compound is about 27 gm as a yellow solid.

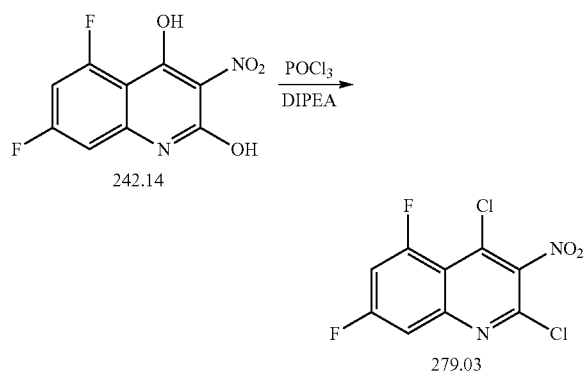

A mixture of 2,4-dihydroxy-5,7-difluoro-3-nitroquinoline (27.1 gm, 0.112 moles), and diisopropylethylamine (22.3 gm, 30 mL, 0.172 moles) is stirred in toluene (100 mL) and cooled in an ice bath. To this mixture is added phosphorous oxychloride (67.4 gm, 41 mL, 0.440 moles) through a dropping funnel over 15 minutes. Once the addition is complete, the brown solution is heated at reflux for 10 hours. After cooling, the reaction solution is stirred in ice and water (800 gm) and a solution of potassium carbonate (80 gm) in water (200 mL) is slowly and cautiously (foaming) added. After stirring for 60 minutes, ethyl acetate (200 mL is added and the organic phase is isolated. The aqueous is extracted with ethyl acetate (200 mL) and these extracts are combined with the original organic phase. The combined organic solutions are washed with 20% potassium carbonate solution before being dried over magnesium sulfate. After filtration, the solvents are removed under vacuum. The residual brown solid is recrystallized from an appropriate solvent such as 2-propanol. After filtration and washing with 2-propanol followed by hexane, the brown solid is dried under vacuum. The yield is about 18 gm.

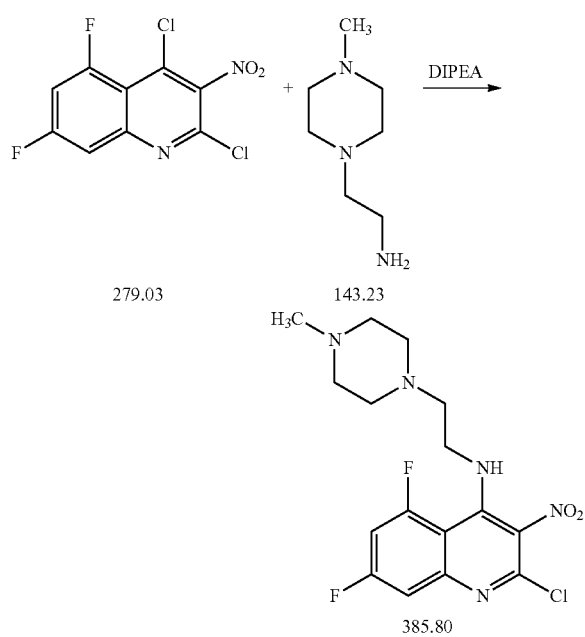

A solution of 2,4-dichloro-5,7-difluoro-3-nitroquinoline (5.58 gm, $2.0 \times 10^{-2}$ moles) in 2-methyl tetrahydrofuran (50 mL) is stirred as diisopropylethylamine (2.84 gm, $2.2 \times 10^{-2}$ moles) and N-2-aminoethyl-N' methylpiperazine (3.15 gm, $2.2 \times 10^{-2}$ moles) are added. This solution is stirred at room temperature overnight. The yellow reaction mixture is diluted with more 2-methyl-tetrahydrofuran (50 mL) and this is washed with water (100 mL) followed by brine (50 mL). After being dried over magnesium sulfate, the solution is filtered and the solvent is removed under reduced pressure. The oily residue is stirred with diethyl ether (25 mL) and this is cooled on ice causing the product to crystallize. The solid yellow product is isolated by filtration, washed with ether and dried. The yield is about 4.32 gm.

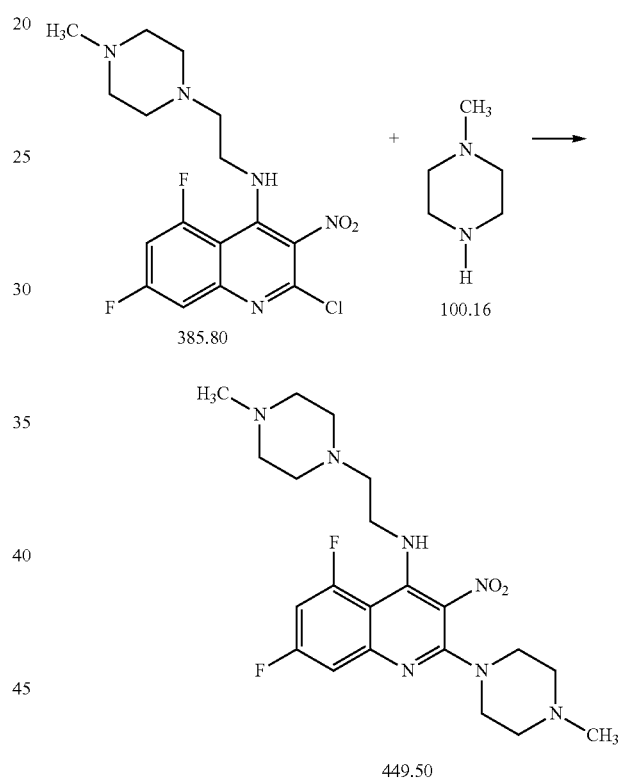

A solution of the chloronitroquinoline (4.17 gm, $1.08 \times 10^{-2}$ moles) in N-methylpyrrolidinone (5 mL) is treated with N-methylpiperazine (1.5 gm, $1.5 \times 10^{-2}$ moles) and diisopropylethylamine (4.19 gm, $3.24 \times 10^{-2}$ moles). This mixture is heated in a pressure tube at 125° C. for 2 hours. TLC (silica, 10% methanol in methylene chloride shows complete conversion of the starting material to a single product. After cooling, the mixture is diluted with ethyl acetate (100 mL) and this solution is washed with water (2×100 mL) and then brine (50 mL). The combined aqueous washes are back extracted with ethyl acetate (50 mL) and this extract is washed with brine before being added to the original organic solution. The solvent is removed under vacuum and the dark orange residual material is dried under vacuum.

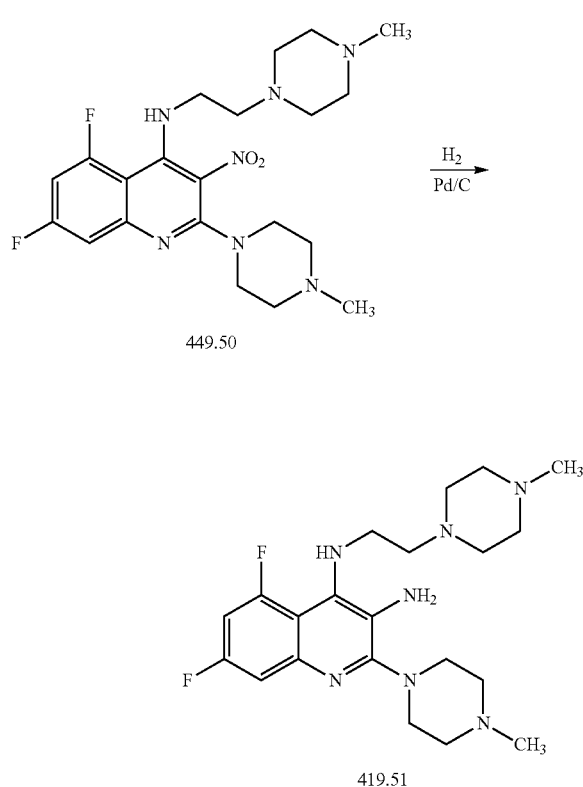 [SMILES: CN1CCN(CCNc2c([N+](=O)[O-])c(N3CCN(C)CC3)nc3cc(F)cc(F)c23)CC1 ; "H2" ; CN1CCN(CCNc2c(N)c(N3CCN(C)CC3)nc3cc(F)cc(F)c23)CC1]

449.50

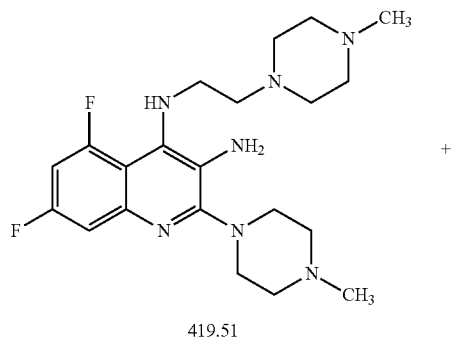

419.51

The crude nitro compound from above (1.08×10⁻² moles) is dissolved in methanol (100 mL) and is hydrogenated over 10% palladium on carbon at 40 psi of hydrogen on a Parr hydrogenator. Once hydrogen consumption stops, the Parr bottle is flushed with argon and the contents are filtered through a pad of Celite to remove the catalyst. The methanol is removed under vacuum and dry toluene (50 mL) is added. This too is removed under vacuum to remove traces of methanol and the residue is re-dissolved in toluene (50 mL).

419.51  +

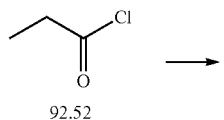

92.52

-continued

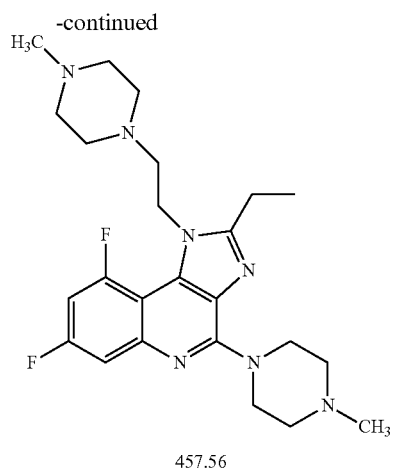

457.56

Propionyl chloride (0.97 gm, 0.0105 moles) dissolved in toluene (10 mL) is added to the toluene solution from above causing a sticky precipitate to form. This mixture is heated at 100° C. for one hour. Toluene is removed under vacuum and is replaced with DMF (15 mL). The resulting solution is heated at 100° C. overnight. After cooling, the solution is diluted with ethyl acetate (200 mL) and this solution is washed with 5% potassium carbonate (2×50 mL). The ethyl acetate solution is then extracted with 5% HCl solution (2×50 mL). The acidic extracts are washed with ethyl acetate (50 mL) and are then made basic by the addition of solid potassium carbonate. The precipitated material is extracted into methylene chloride (200 mL) and the solution is dried over magnesium sulfate, filtered and evaporated under vacuum to provide a brown solid. Purification is achieved by chromatography on silica gel to give about 1.4 gm of the imidazoquinoline.

Example 3 (Compound 56)

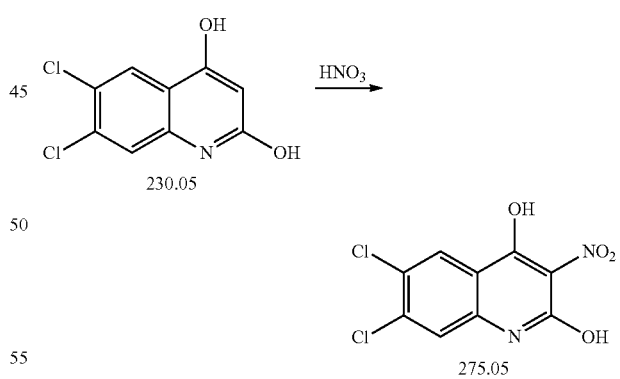

A mixture of 2,4-dihydroxy, 6,7-dichloroquinoline (28.5 gm, 0.124 moles) in acetic acid (120 mL) is stirred as concentrated nitric acid (32 mL) is added in a single portion. A thick mass results. This is heated in an oil bath set at 105° C. After a few minutes the mass liquefies allowing the mixture to be stirred. After a clear brown solution forms, the reaction is allowed to proceed at 105° C. for 10 minutes. The heating bath is removed and water (200 mL) is added with stirring causing a slurry to form. After stirring for 30 minutes, the solid is isolated by filtration and is washed well with water. The solid is then dried under vacuum. The yield of the nitro compound is about 30 gm as a yellow solid.

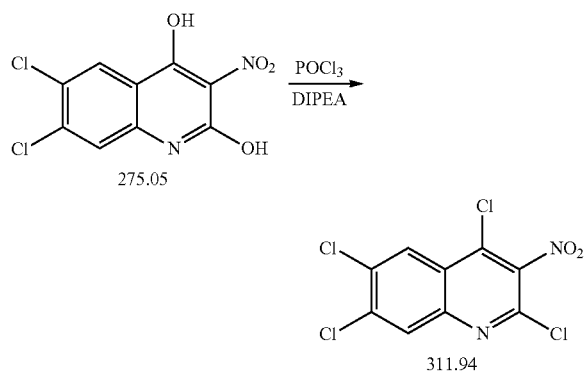

A mixture of 2,4-dihydroxy-6,7-dichloro-3-nitroquinoline (30.8 gm, 0.112 moles), and diisopropylethylamine (22.3 gm, 30 mL, 0.172 moles) is stirred in toluene (100 mL) and cooled in an ice bath. To this mixture is added phosphorous oxychloride (67.4 gm, 41 mL, 0.440 moles) through a dropping funnel over 15 minutes. Once the addition is complete, the brown solution is heated at reflux for 10 hours. After cooling, the reaction solution is stirred in ice and water (800 gm) and a solution of potassium carbonate (80 gm) in water (200 mL) is slowly and cautiously (foaming) added. After stirring for 60 minutes, ethyl acetate (200 mL is added and the organic phase is isolated. The aqueous is extracted with ethyl acetate (200 mL) and these extracts are combined with the original organic phase. The combined organic solutions are washed with 20% potassium carbonate solution before being dried over magnesium sulfate. After filtration, the solvents are removed under vacuum. The residual brown solid is recrystallized from an appropriate solvent such as 2-propanol. After filtration and washing with 2-propanol followed by hexane, the brown solid is dried under vacuum. The yield is about 20 gm.

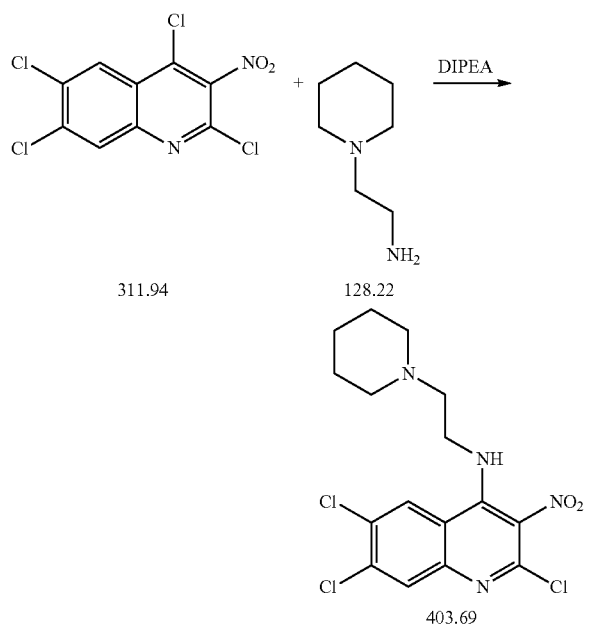

A solution of 2,4,6,7-tetrachloro-3-nitroquinoline (6.24 gm, $2.0 \times 10^{-2}$ moles) in 2-methyl tetrahydrofuran (50 mL) is stirred as diisopropylethylamine (2.84 gm, $2.2 \times 10^{-2}$ moles) and N-2-aminoethylpiperidine (2.82 gm, $2.2 \times 10^{-2}$ moles) are added. This solution is stirred at room temperature overnight. The yellow reaction mixture is diluted with more 2-methyl-tetrahydrofuran (50 mL) and this is washed with water (100 mL) followed by brine (50 mL). After being dried over magnesium sulfate, the solution is filtered and the solvent is removed under reduced pressure. The oily residue is stirred with diethyl ether (25 mL) and this is cooled on ice causing the product to crystallize. The solid yellow product is isolated by filtration, washed with ether and dried. The yield is about 4.5 gm.

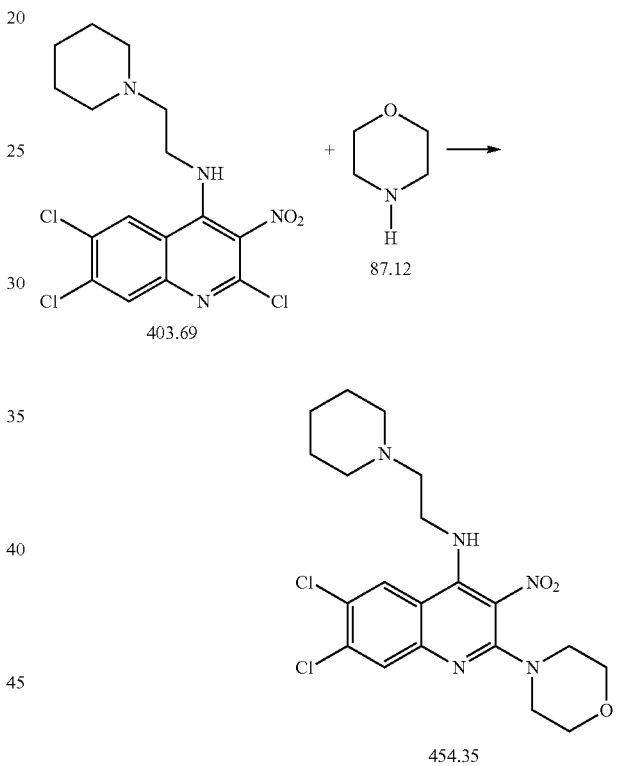

A solution of the chloronitroquinoline (4.36 gm, $1.08 \times 10^{-2}$ moles) in N-methylpyrrolidinone (5 mL) is treated with morpholine (1.3 gm, $1.5 \times 10^{-2}$ moles) and diisopropylethylamine (4.19 gm, 5.67 mL, $3.24 \times 10^{-2}$ moles). This mixture is heated in a pressure tube at 125° C. for 2 hours. TLC (silica, 10% methanol in methylene chloride shows complete conversion of the starting material to a single product. After cooling, the mixture is diluted with ethyl acetate (100 mL) and this solution is washed with water (2×100 mL) and then brine (50 mL). The combined aqueous washes are back extracted with ethyl acetate (50 mL) and this extract is washed with brine before being added to the original organic solution. The solvent is removed under vacuum and the dark orange residual material is dried under vacuum.

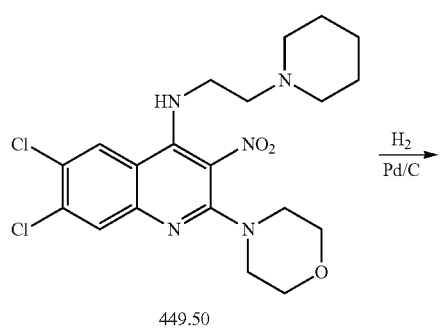

449.50

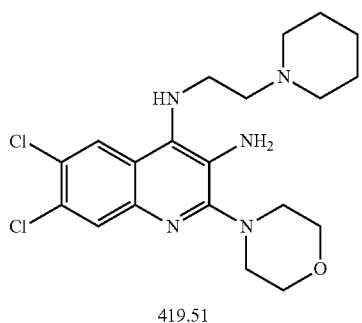

419.51

The crude nitro compound from above (1.08×10⁻² moles) is dissolved in methanol (100 mL) and is hydrogenated over 10% palladium on carbon at 40 psi of hydrogen on a Parr hydrogenator. Once hydrogen consumption slows down, the Parr bottle is flushed with argon and the contents are filtered through a pad of Celite to remove the catalyst. The methanol is removed under vacuum and dry toluene (50 mL) is added. This too is removed under vacuum to remove traces of methanol and the residue is re-dissolved in toluene (50 mL).

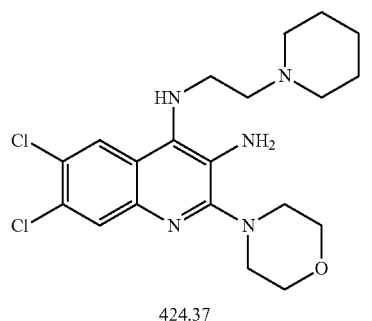

424.37

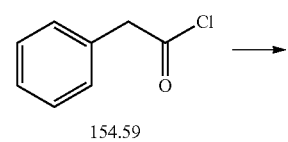

154.59

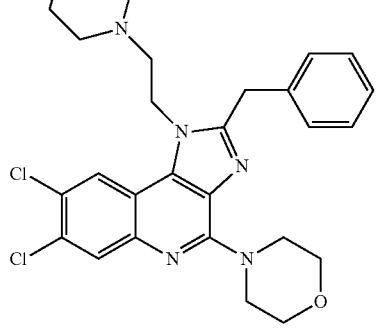

524.48

Phenylacetyl chloride (1.62 gm, 0.0105 moles) dissolved in toluene (10 mL) is added to the toluene solution from above causing a sticky precipitate to form. This mixture is heated at 100° C. for one hour. Toluene is removed under vacuum and is replaced with DMF (15 mL). The resulting solution is heated at 100° C. overnight. After cooling, the solution is diluted with ethyl acetate (200 mL) and this solution is washed with 5% potassium carbonate (2×50 mL). The ethyl acetate solution is then extracted with 5% HCl solution (2×50 mL). The acidic extracts are washed with ethyl acetate (50 mL) and are then made basic by the addition of solid potassium carbonate. The precipitated material is extracted into methylene chloride (200 mL) and the solution is dried over magnesium sulfate, filtered and evaporated under vacuum to provide a brown solid. Purification is achieved by chromatography on silica gel to give about 1.6 gm of the imidazoquinoline.

Example 4 (Compound 55)

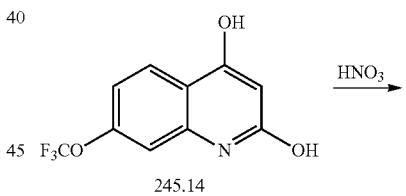

245.14

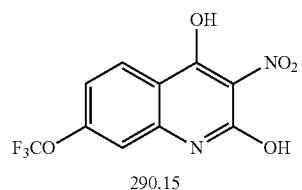

290.15

A mixture of 2,4-dihydroxy-7-trifluoromethylquinolin (30.4 gm, 0.124 moles) in acetic acid (120 mL) is stirred as concentrated nitric acid (32 mL) is added in a single portion. A thick mass results. This is heated in an oil bath set at 105° C. After a few minutes the mass liquefies allowing the mixture to be stirred. After a clear brown solution forms, the reaction is allowed to proceed at 105° C. for 10 minutes. The heating bath is removed and water (200 mL) is added with stirring causing a slurry to form. After stirring for 30 minutes, the solid is isolated by filtration and is washed well with water. The solid is then dried under vacuum. The yield of the nitro compound is about 34 gm as a yellow solid.

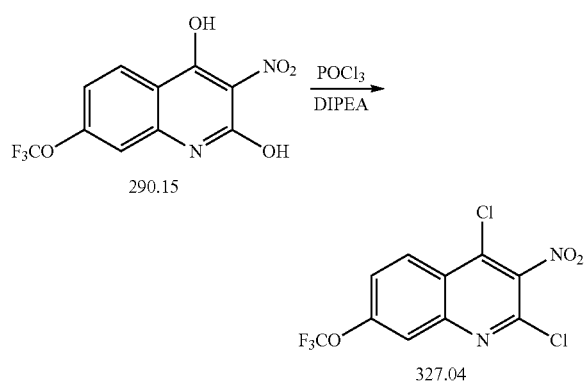

A mixture of 2,4-dihydroxy-7-trifluoromethyl-3-nitroquinoline (32.5 gm, 0.112 moles), and diisopropylethylamine (22.3 gm, 30 mL, 0.172 moles) is stirred in toluene (100 mL) and cooled in an ice bath. To this mixture is added phosphorous oxychloride (67.4 gm, 41 mL, 0.440 moles) through a dropping funnel over 15 minutes. Once the addition is complete, the brown solution is heated at reflux for 10 hours. After cooling, the reaction solution is stirred in ice and water (800 gm) and a solution of potassium carbonate (80 gm) in water (200 mL) is slowly and cautiously (foaming) added. After stirring for 60 minutes, ethyl acetate (200 mL is added and the organic phase is isolated. The aqueous is extracted with ethyl acetate (200 mL) and these extracts are combined with the original organic phase. The combined organic solutions are washed with 20% potassium carbonate solution before being dried over magnesium sulfate. After filtration, the solvents are removed under vacuum. The residual brown solid is recrystallized from an appropriate solvent such as 2-propanol. After filtration and washing with 2-propanol followed by hexane, the brown solid is dried under vacuum. The yield is about 21 gm.

A solution of 2,4-dichloro-7-trifluoromethyl-3-nitroquinoline (6.54 gm, $2.0 \times 10^{-2}$ moles) in 2-methyl tetrahydrofuran (50 mL) is stirred as diisopropylethylamine (2.84 gm, $2.2 \times 10^{-2}$ moles) and N-2-aminoethyl-N' methylpiperazine (3.15 gm, $2.2 \times 10^{-2}$ moles) are added. This solution is stirred at room temperature overnight. The yellow reaction mixture is diluted with more 2-methyl-tetrahydrofuran (50 mL) and this is washed with water (100 mL) followed by brine (50 mL). After being dried over magnesium sulfate, the solution is filtered and the solvent is removed under reduced pressure. The oily residue is stirred with diethyl ether (25 mL) and this is cooled on ice causing the product to crystallize. The solid yellow product is isolated by filtration, washed with ether and dried. The yield is about 5.0 gm.

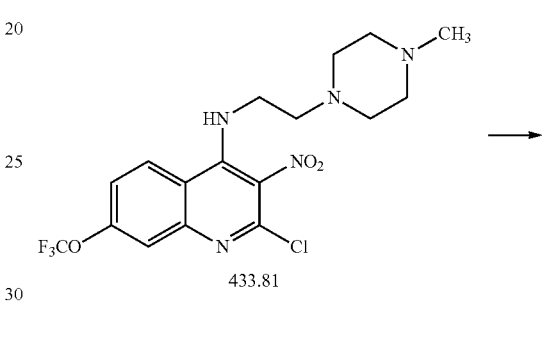

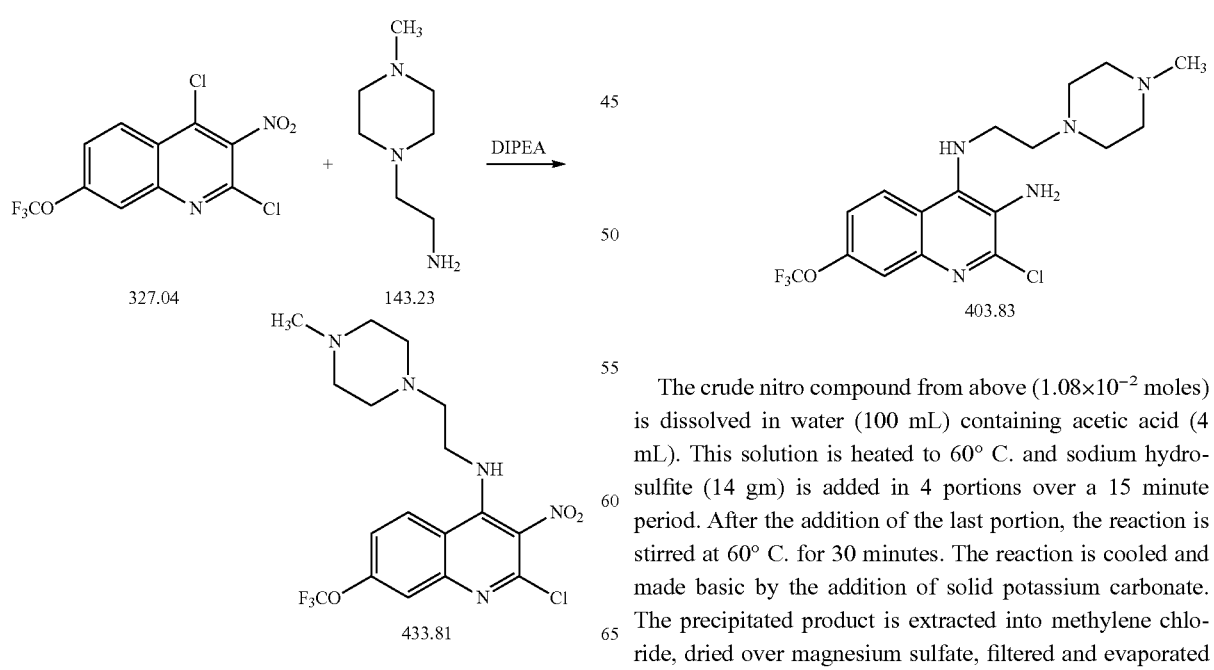

The crude nitro compound from above ($1.08 \times 10^{-2}$ moles) is dissolved in water (100 mL) containing acetic acid (4 mL). This solution is heated to 60° C. and sodium hydrosulfite (14 gm) is added in 4 portions over a 15 minute period. After the addition of the last portion, the reaction is stirred at 60° C. for 30 minutes. The reaction is cooled and made basic by the addition of solid potassium carbonate. The precipitated product is extracted into methylene chloride, dried over magnesium sulfate, filtered and evaporated under vacuum. The residue is dissolved in toluene (50 mL).

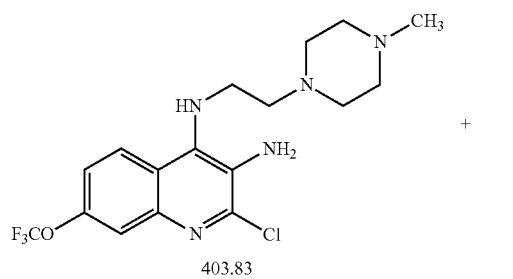

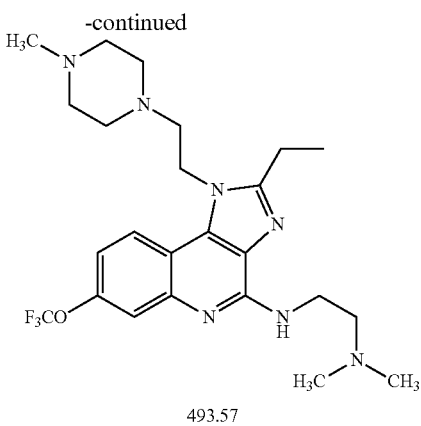

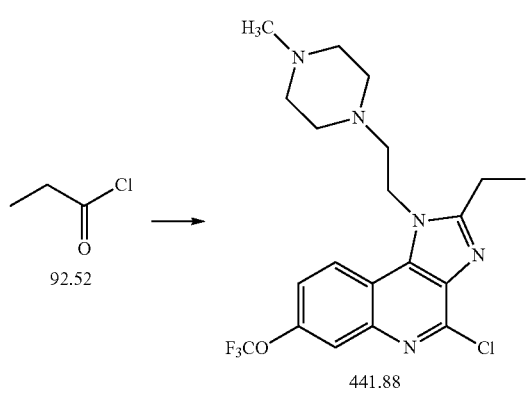

Propionyl chloride (0.97 gm, 0.0105 moles) dissolved in toluene (10 mL) is added to the toluene solution from above causing a sticky precipitate to form. This mixture is heated at 100° C. for one hour. Toluene is removed under vacuum and is replaced with DMF (15 mL). The resulting solution is heated at 100° C. overnight. After cooling, the solution is diluted with ethyl acetate (200 mL) and this solution is washed with 5% potassium carbonate (2×50 mL). The ethyl acetate solution is then extracted with 5% HCl solution (2×50 mL). The acidic extracts are washed with ethyl acetate (50 mL) and are then made basic by the addition of solid potassium carbonate. The precipitated material is extracted into methylene chloride (200 mL) and the solution is dried over magnesium sulfate, filtered and evaporated under vacuum to provide a brown solid. Purification is achieved by chromatography on silica gel to give about 1.3 gm of the 2-chloroimidazoquinoline.

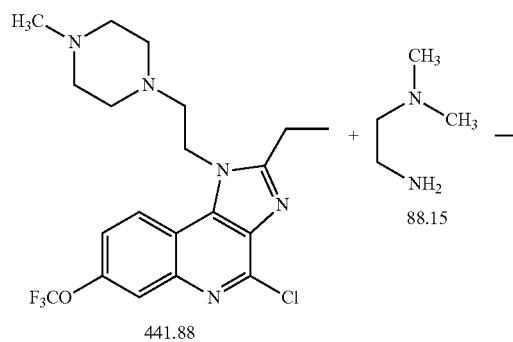

A solution of the chloroimidazoquinoline (4.77 gm, 1.08× $10^{-2}$ moles) in N-methylpyrrolidinone (5 mL) is treated with N,N-dimethylethylenediamine (1.32 gm, 1.5×$10^{-2}$ moles) and diisopropylethylamine (4.19 gm, 5.67 mL, 3.24×$10^{-2}$ moles). This mixture is heated in a pressure tube at 125° C. for 4 hours. TLC (silica, 10% methanol in methylene chloride shows complete conversion of the starting material to a single product. After cooling, the mixture is diluted with ethyl acetate (100 mL) and this solution is washed with water (2×100 mL) and then brine (50 mL). The combined aqueous washes are back extracted with ethyl acetate (50 mL) and this extract is washed with brine before being added to the original organic solution. The solvent is removed under vacuum and the residual material is purified by chromatography on silica.

Example 5 (Compound 60)

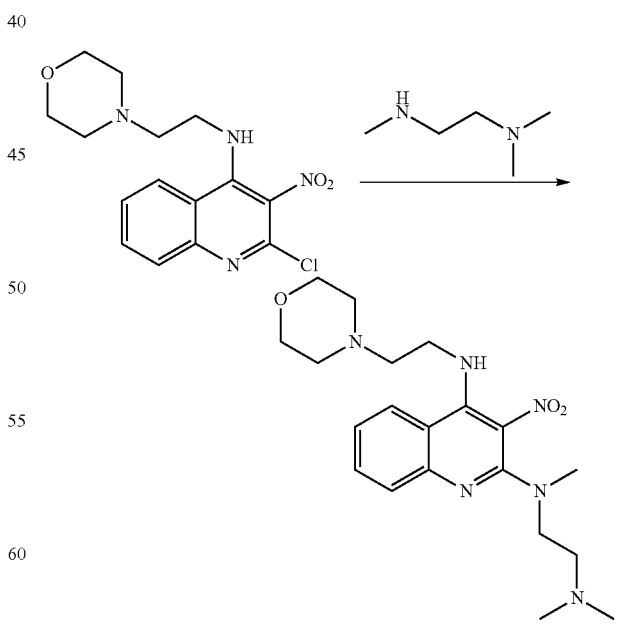

A solution of 2-chloro-N-(2-morpholinoethyl)-3-nitroquinolin-4-amine (4.3 g, 12.7 mmol, prepared as shown above) in NMP (10 mL) was treated with dimethyl[2-(methylamino)ethyl]amine (1.8 g, 17.8 mmol) and DIPEA (6.7 mL, 38.1 mmol). The mixture was stirred at 125° C. for 2 h. After cooling, the mixture was diluted with ethyl acetate (100 mL) and this solution was washed with water (2×50 mL) and then brine (50 mL). The aqueous layer was adjusted to pH>9. The combined aqueous washes were back extracted with ethyl acetate (50 mL) and this extract was washed with brine before being added to the original organic solution. The solvent was removed under vacuum and the dark orange residual material was dried under vacuum. 3.3 g of crude N²-(2-(dimethylamino)ethyl)-N²-methyl-N⁴-(2-morpholinoethyl)-3-nitroquinoline-2,4-diamine was isolated after column chromatography (silica, DCM:MeOH=50:1).

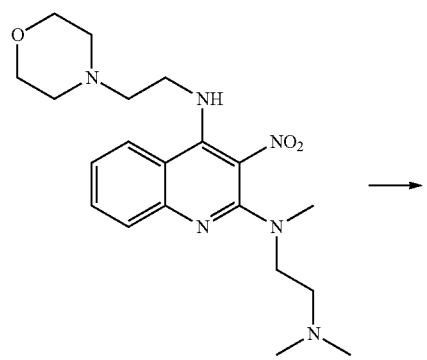

N²-(2-(dimethylamino)ethyl)-N²-methyl-N⁴-(2-morpholinoethyl)-3-nitroquinoline-2,4-diamine (3.3 g, 8.2 mmol) was dissolved in methanol (100 mL) and was hydrogenated over palladium on carbon (1.5 g) at 50 psi of hydrogen. The mixture was stirred at room temperature for 3 h. After filtration, the methanol was removed under reduced pressure. 2.9 g crude N²-(2-(dimethylamino)ethyl)-N²-methyl-N⁴-(2-morpholinoethyl)quinoline-2,3,4-triamine was isolated.

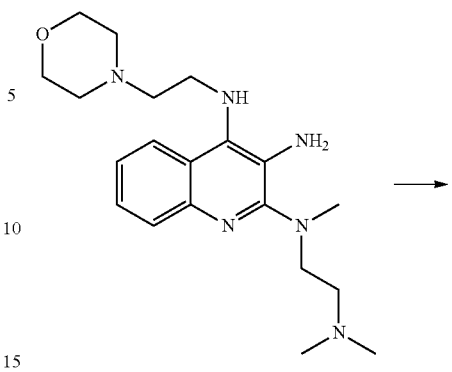

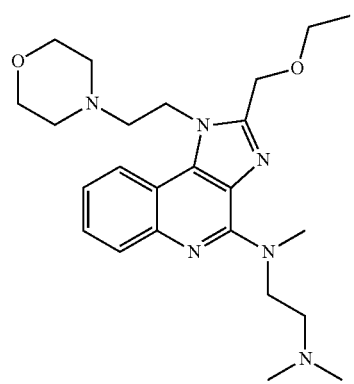

Compound 60

A solution of ethoxyacetic acid (0.81 g, 7.8 mmol) and oxalyl chloride (2.0 g, 15.6 mmol) in dichloromethane was stirred at room temperature overnight. The solvent was removed under vacuum carefully, because the boiling point of ethoxyacetyl chloride is low. N²-(2-(dimethylamino)ethyl)-N²-methyl-N⁴-(2-morpholinoethyl)quinoline-2,3,4-triamine (2.9 g, 7.8 mmol) and DIPEA (3.0 g, 33.4 mmol) were dissolved in THF (20 mL). Ethoxyacetyl chloride from above was dissolved in THF (10 mL) and charged through a dropping funnel into the reaction solution. The mixture was stirred at room temperature for 2 h. After the completion of the reaction was confirmed by LC/MS, the solvent was concentrated and replaced with DMF (30 mL). The dark solution was stirred at 125° C. overnight. After cooling, the mixture was diluted with ethyl acetate (100 mL) and this solution was washed with water (2×50 mL) and then brine (50 mL). The washes were extracted with THF (50 mL).

The combined organic solutions were concentrated and the crude product was isolated. The crude product was purified by Prep-HPLC. To give 0.87 g of compound 60. Mass spec, M+1=441.50.

Example 6 (Compound 61)

Compound 61 was prepared according to the scheme shown below, which utilized procedures similar to those used for compound 60.

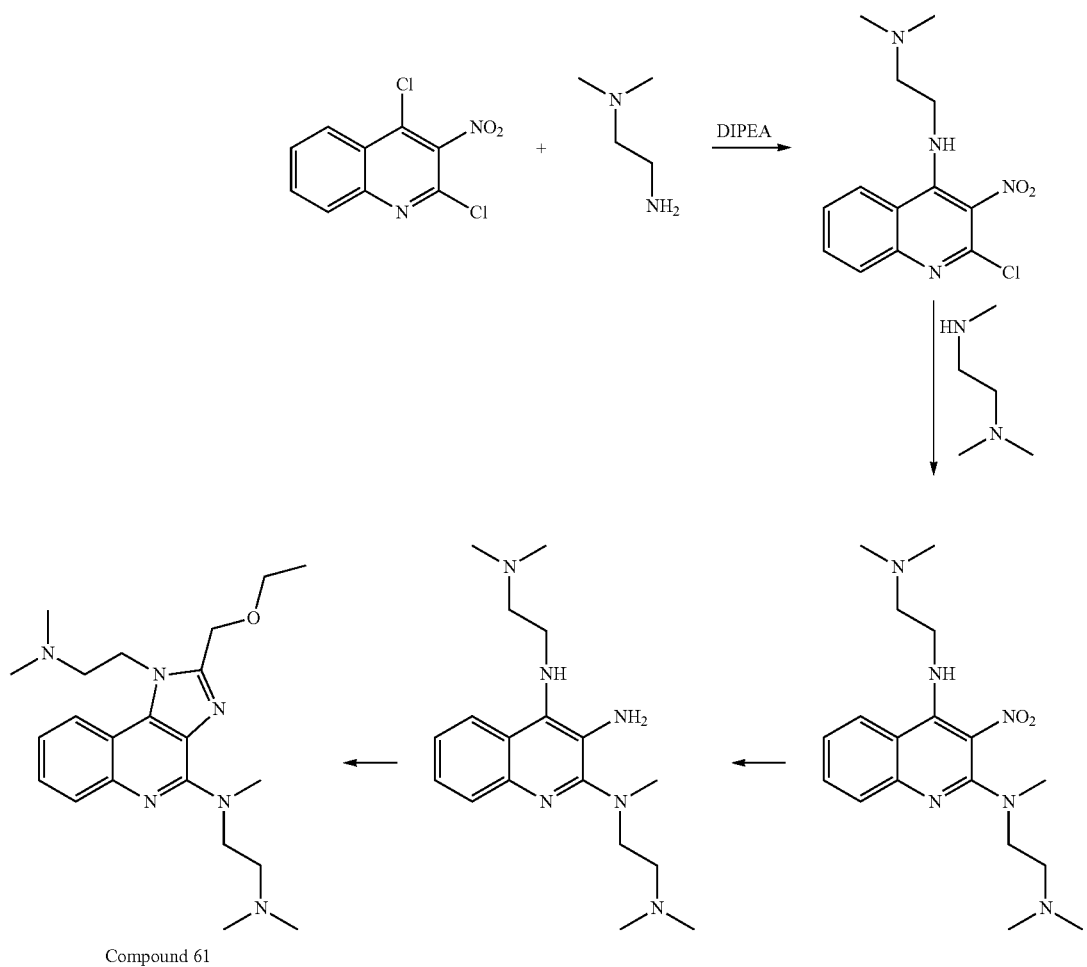
2.52 g TFA salt of compound 61 was isolated after Pre-HPLC purification. Mass spec: M+1=399.50.
Example 7 (Compound 62)
Compound 62 was prepared according to the scheme shown below, which utilized procedures similar to those used for compound 60.
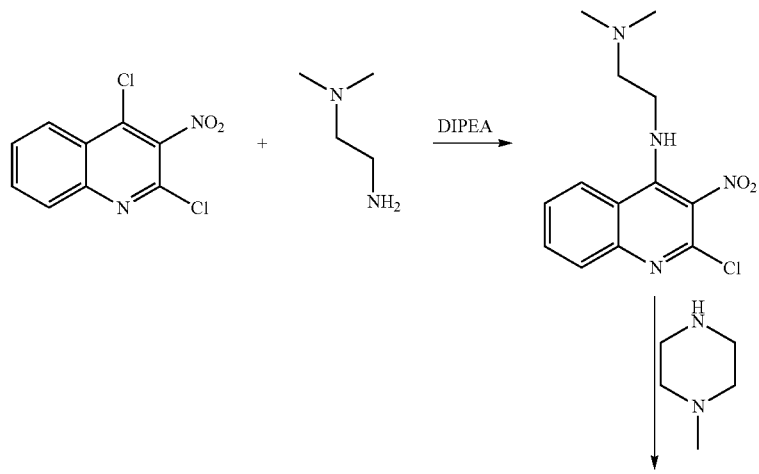

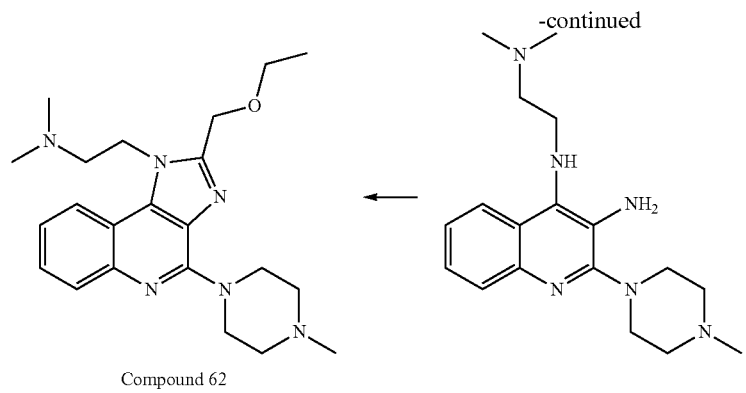
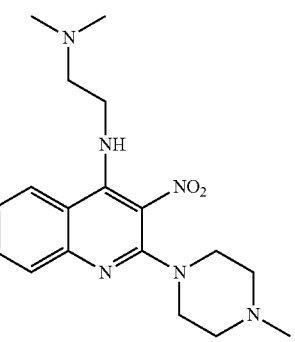

Compound 62

1.6 g compound 62 was isolated after Prep-HPLC purification. Mass spec M+1=397.30.

Example 8 (Compound 63)

Compound 63 was prepared according to the scheme shown below, which utilized procedures similar to those used for compound 60.

0.75 g TFA salt of compound 63 was isolated after Pre-HPLC purification. NMR (DMSO D6): 1.18 ppm, triplet, 3H 2.95 ppm, singlet, 6H 3.39 ppm, singlet, 4H 3.60 ppm, multiplet, 7H 3.92 ppm, quartet, 2H 4.72 ppm, broad singlet, 2H 4.90 ppm, singlet plus multiplet, 4H 7.51 ppm, broad singlet, 1H 7.90 ppm, broad singlet, 1H 8.15 ppm, broad singlet, 1H 8.31 ppm, doublet, 1H.

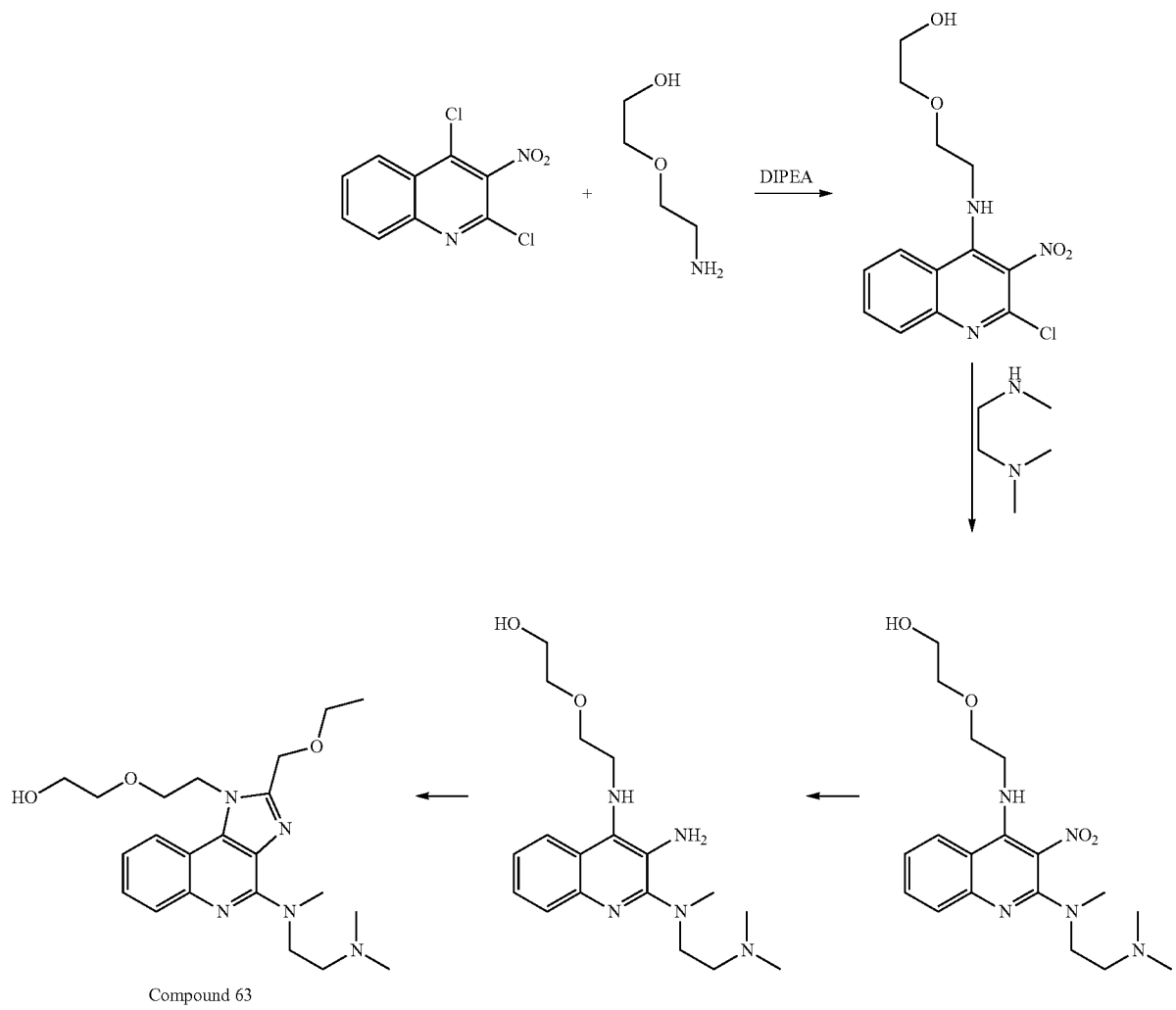

Compound 63

Example 9 (Compound 64)

Compound 64 was prepared according to the scheme shown below, which utilized procedures similar to those used for compound 60.

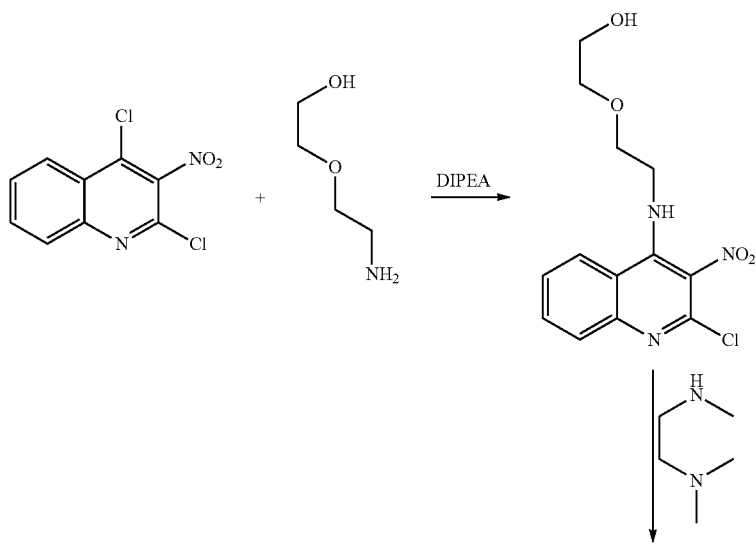

Example 10 (Compound 65)

Compound 65 was prepared according to the scheme shown below, which utilized procedures similar to those

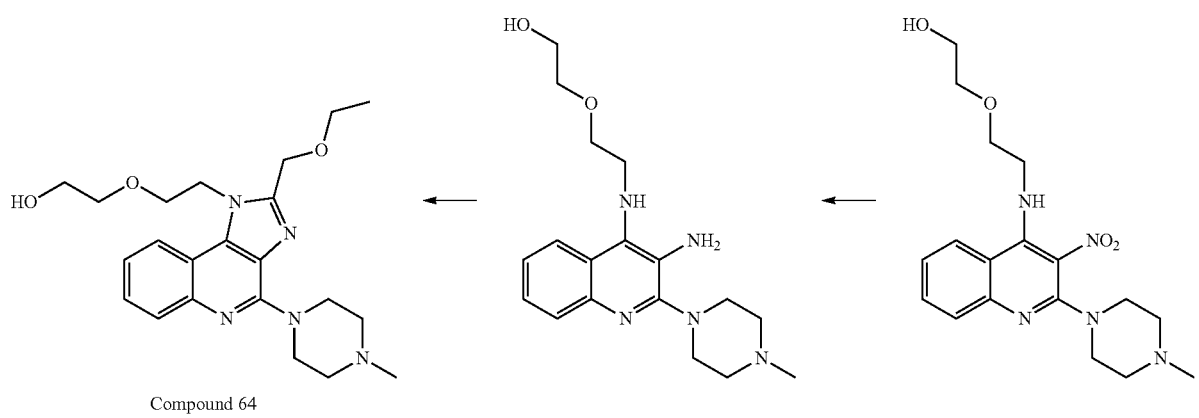

Compound 64

1.47 gm of the TFA salt of compound 64 was isolated after Prep-HPLC purification. NMR (DMSO D6) 1.18 ppm, triplet, 3H 2.86 ppm, singlet, 3H 3.40 ppm, multiplet, 6H 3.58 ppm, multiplet, 6H 3.90 ppm, triplet, 2H 4.85 ppm, singlet, 2H 4.90 ppm, triplet, 2H 5.65 ppm, broad singlet, 2H 7.47 ppm, triplet, 1H 7.54 ppm, triplet, 1H 7.88 ppm, doublet, 1H 8.28 ppm, doublet, 1H.

used for compound 60, with the exception that the purification of compound 65 followed the following protocol: the oily residue after concentration was recrystallized from ACN. After filtration, the brown solid was dissolved in MeOH. HCl/MeOH (3 mL) was dropped into the solution.

111

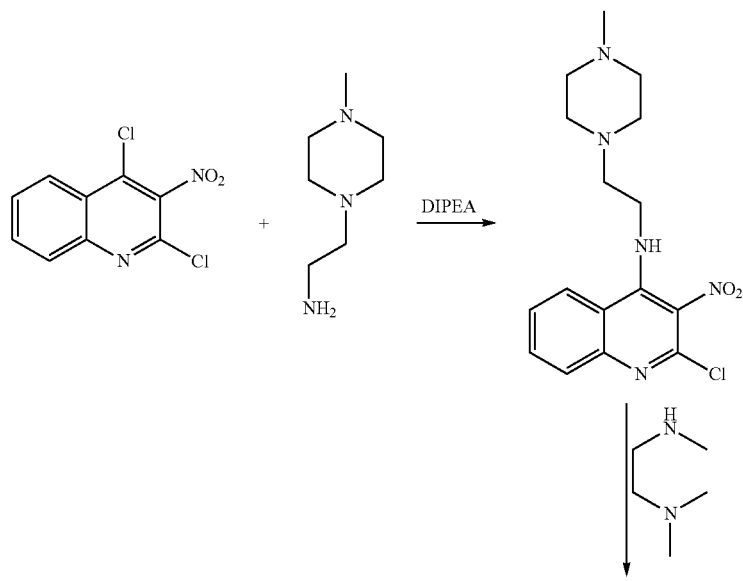

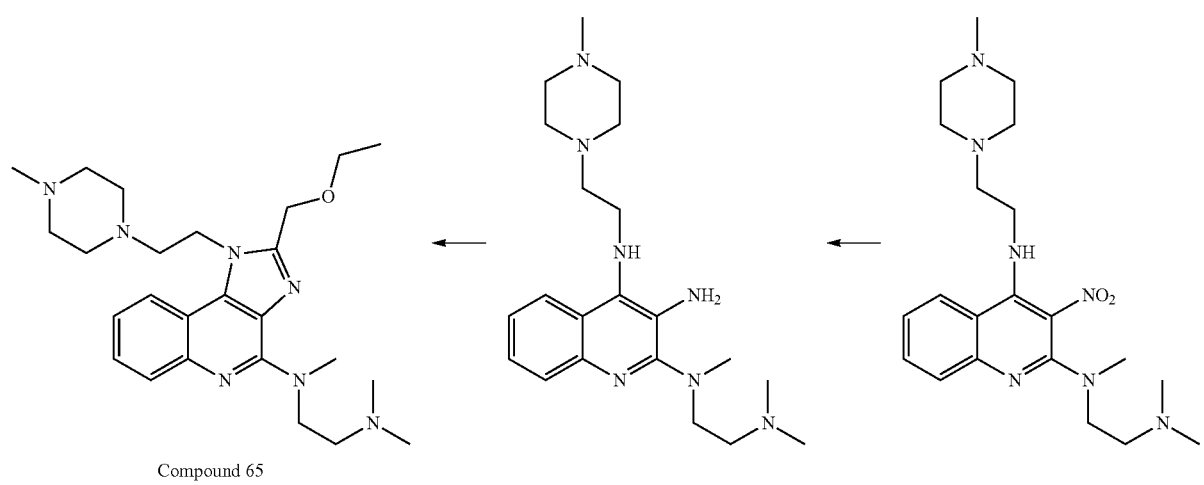

Compound 65

A white solid separated and was isolated by filtration to provide 0.51 g HCl salt of compound 65. NMR (DMSO D6) 1.22 PPM, triplet, 3H, 2.76 ppm, singlet, 3H, 2.86 ppm, multiplet, 8H, 3.17 ppm broad singlet, 3H, 3.45 ppm, multiplet, 2H, 3.53 ppm multiplet, 4H, 3.64 ppm, multiplet, 5H, 4.90 ppm, overlapping singlet and multiplet, 6H, 7.62 ppm, triplet, 1H, 7.78 ppm, triplet, 1H, 8.40 ppm, multiplet, 1H, 8.60 ppm, broad singlet, 1H.

Example 11 (Compound 66)

Compound 66 was prepared according to the scheme shown below, which utilized procedures similar to those used for compound 60,

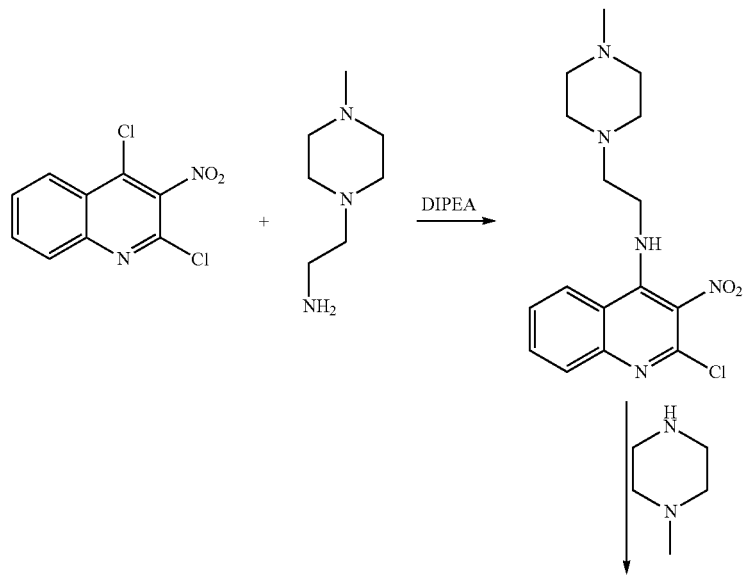

0.68 gm of compound 66 was isolated after Pre-HPLC purification. NMR DMSO (D6) 1.18 ppm, triplet, 3H 2.15 ppm, singlet, 3H 2.23 ppm, singlet, 3H 2.33 ppm, broad singlet, 4H 2.49 ppm, multiplet, 8H 2.78 ppm, triplet, 2H 3.58 ppm, quartet, 2H 4.20 ppm, broad singlet, 4H 4.72 ppm, triplet, 2H 4.81 ppm, singlet, 2H 7.32 ppm, triplet, 1H 7.49 ppm, triplet, 1H 7.70 ppm, doublet, 1H 8.09 ppm, doublet, 1H.

Example 12 (Compound 67)

Compound 67 was prepared according to the scheme shown below, which utilized procedures similar to those used for compound 60, with the exception that the last step in the scheme below followed the following protocol:

a solution of $N^2,N^4$-bis(2-(dimethylamino)ethyl)-$N^2$-methylquinoline-2,3,4-triamine (5.0 g, 15.2 mmol) in trim-ethyl orthoformate (60 mL) was stirred at 125° C. overnight. LC/MS showed about 65% SM was consumed. The solvent was removed under reduced pressure and the remaining oily residue was purified by column (silica, DCM:methanol=10:1). The fractions containing the product were pooled and evaporated under reduced pressure to give 2.5 g of the product as an oil. The oil was dissolved in methanol and treated with HCl in methanol causing the crystalline hydrochloride to separate as a white solid. The hydrochloride salt was stirred in ethyl acetate/methanol=5:1 (15 mL) for 1 h. After filtration 0.7 g of the HCl salt of compound 67 was isolated. NMR (DMSO D6) 3.08 ppm, singlet, 6H 3.11 ppm, singlet, 6H 3.65 ppm, singlet, 3H 3.78 ppm, triplet, 2H 3.85 ppm, triplet, 2H 4.99 ppm, triplet, 2H 5.32 ppm, triplet, 2H 7.77 ppm, triplet, 1H 7.84 ppm, triplet, 1H 8.26 ppm, doublet, 1H 8.40 ppm, doublet, 1H 8.63 ppm, singlet, 1H.

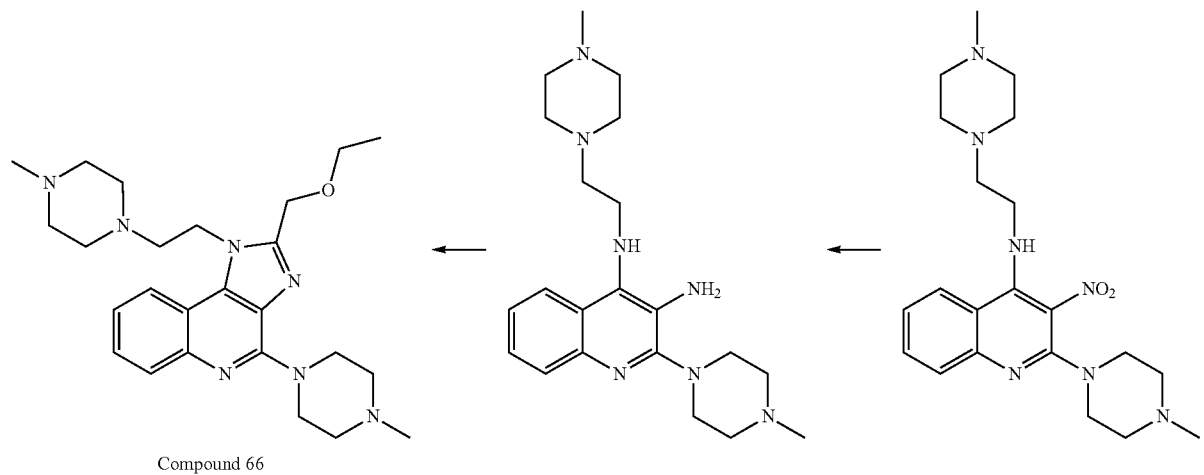

Compound 66

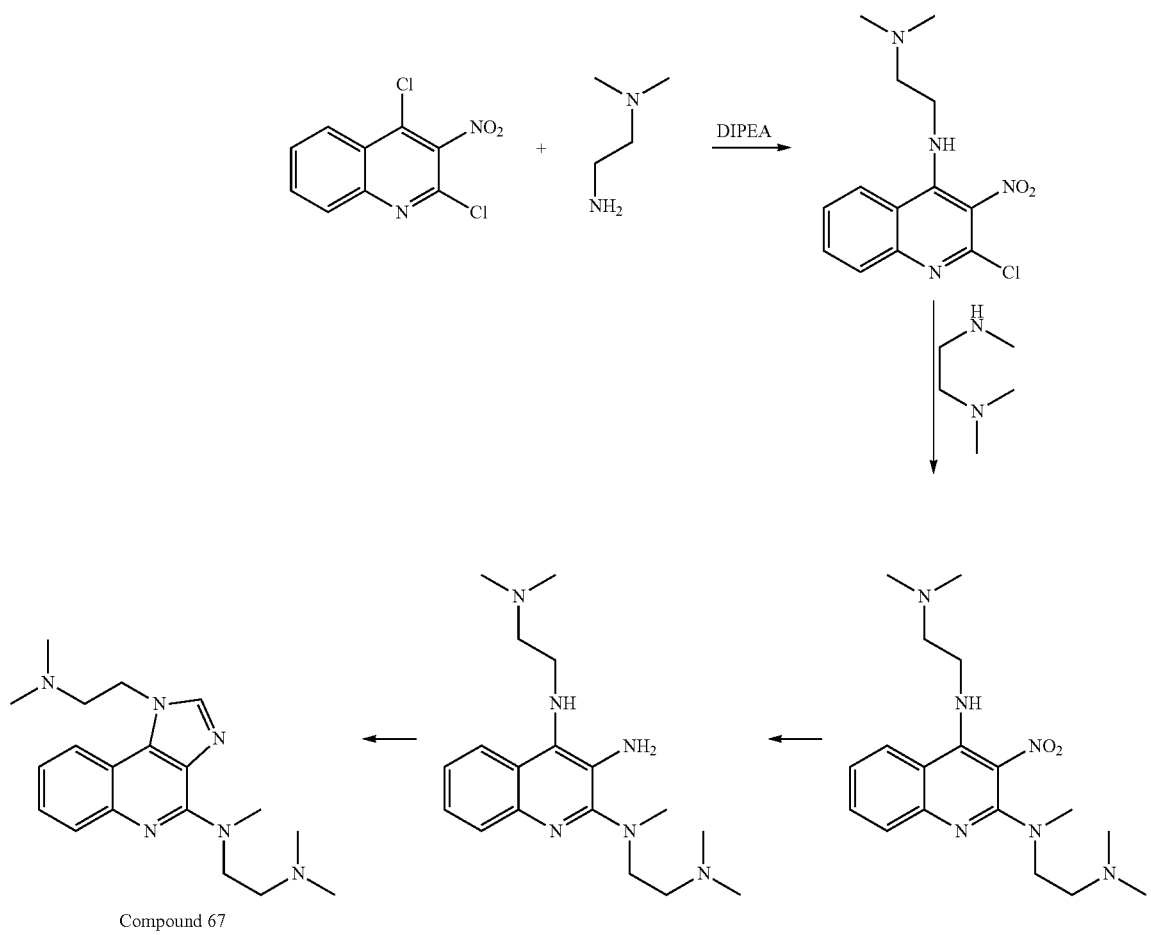

Compound 67

Example 13 (Compound 68)

Compound 68 was prepared according to the scheme shown below, which utilized procedures similar to those used for compound 60, with the exception that the last step in the scheme below followed the following protocol:

a solution of $N^2,N^4$-bis(2-(dimethylamino)ethyl)-$N^2$-methylquinoline-2,3,4-triamine (6.2 g, 18.8 mmol) in THF (100 mL) was stirred at room temperature. To this solution was added carbonyldiimidazole (4.5 g, 28.2 mmol). The mixture was stirred at room temperature for 30 min. Additional carbonyldiimidazole (4.5 g, 28.2 mmol) and pyridine (9 mL) was added to the reaction solution. This mixture was heated at reflux with stirring for 3 hours. The reaction was then cooled to 0° C. in an ice bath causing a white solid to separate. The solid was isolated by filtration and then purified by Prep-HPLC. To give 0.60 g compound 68.

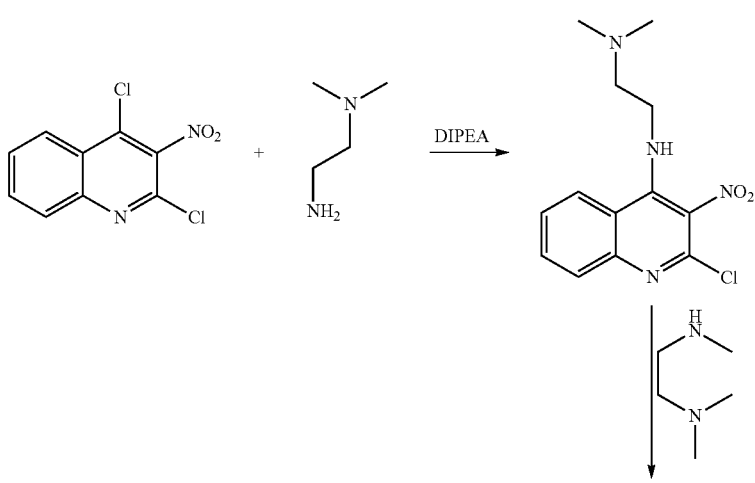

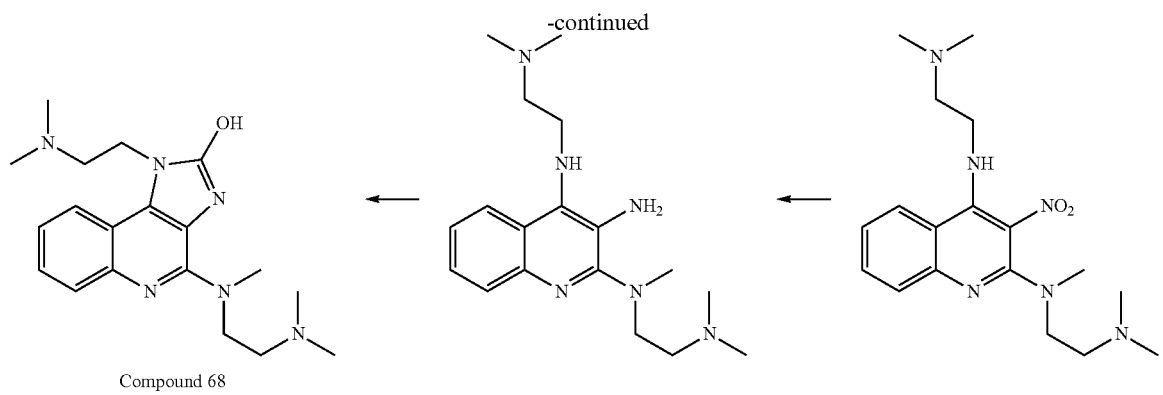

Compound 68

NMR (DMSO D6) 2.21 ppm, singlet, 6H 2.32 ppm, singlet, 6H 2.59 ppm, triplet, 2H 2.86 ppm, triplet, 2H 3.08 ppm, singlet, 3H 3.50 ppm, triplet, 2H 4.30 ppm, triplet, 2H 7.33 ppm, triplet, 1H 7.45 ppm, triplet, 1H 7.68 ppm, doublet, 1H 8.00 ppm, doublet, 1H.

Example 14 (Compound 69)

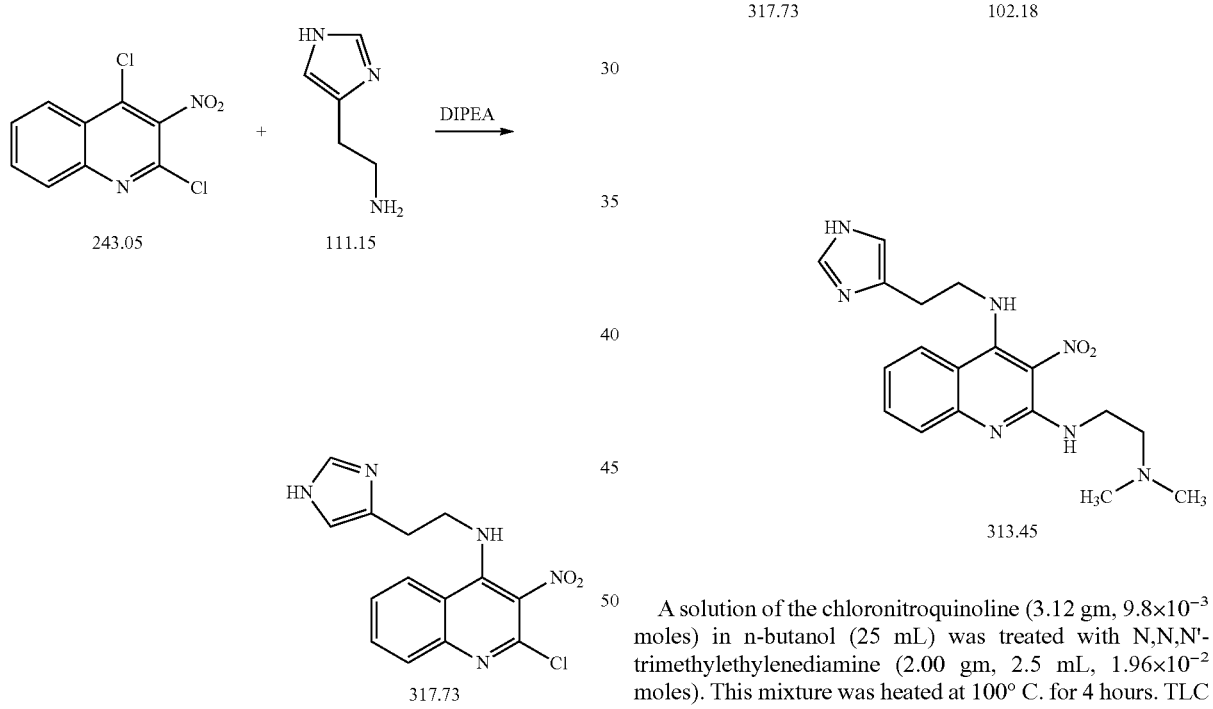

A solution of 2,4-dichloro-3-nitroquinoline (4.86 gm, $2.0 \times 10^{-2}$ moles) in chloroform (100 mL) was stirred as diisopropylethylamine (2.84 gm, 3.83 mL, $2.2 \times 10^{-2}$ moles) and histamine (2.45 gm, $2.2 \times 10^{-2}$ moles) were added. This solution was stirred at room temperature overnight. The yellow reaction mixture was diluted with water (100 mL) and stirring was continued for 10 minutes. The solid yellow product was isolated by filtration, washed with methylene chloride, then ether and dried. The yield was 3.12 gm (49.1%). TLC (silica, 10% methanol in methylene chloride) showed a single product at Rf=0.31.

A solution of the chloronitroquinoline (3.12 gm, $9.8 \times 10^{-3}$ moles) in n-butanol (25 mL) was treated with N,N,N'-trimethylethylenediamine (2.00 gm, 2.5 mL, $1.96 \times 10^{-2}$ moles). This mixture was heated at 100° C. for 4 hours. TLC (silica, 25% methanol in methylene chloride showed complete conversion of the starting material to a single product (Rf=0.26). After cooling, the mixture was diluted with diethyl ether (200 mL) causing a solid to precipitate. This was extracted into 2% hydrochloric acid (2×100 mL). The combined extracts were washed with ether (100 mL) and were then made basic by the addition of solid potassium carbonate. The precipitated red oil was extracted into methylene chloride (2×150 mL) and the combined extracts were dried over magnesium sulfate. The solution was filtered and the solvent was removed under vacuum. The residual red oil was dried under vacuum and was used without further purification in the next step.

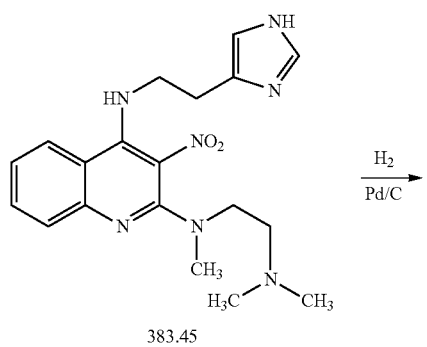

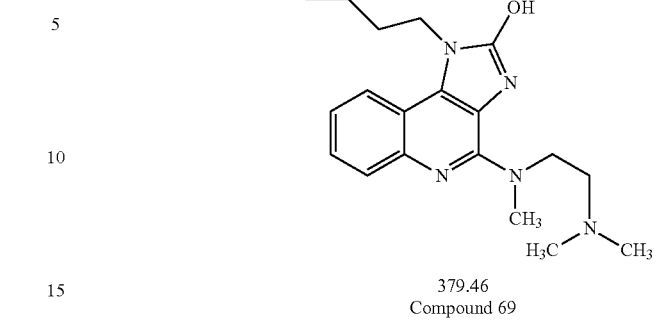

Compound 69

To the toluene solution from step 3 was added carbonyl diimidazole (6.36 gm, $3.92 \times 10^{-2}$ moles) and this solution was heated at reflux for 30 minutes. After cooling, water (25 mL) was added and stirring was continued for 2 hours. The aqueous was isolated and made basic by the addition of solid potassium carbonate. The precipitated product was extracted into methylene chloride (200 mL) and the extract was dried over magnesium sulfate. After filtration, the methylene chloride was evaporated under reduced pressure to give 2.48 gm of the product as a tan foam. This was dissolved in ethanol (25 mL), and the solution was stirred and treated with a solution of concentrated sulfuric acid (962 mg) in ethanol (10 mL). A white solid separated which quickly formed a sticky mass. The ethanol was decanted and diethyl ether (100 mL) was added. After stirring for 2 hours, the tan solid was isolated by filtration, washed with ether and dried to provide compound 69 sulfate in a yield of 2.6 gm. Mass spec, M+1=380.38.

Example 15 (Compound 70)

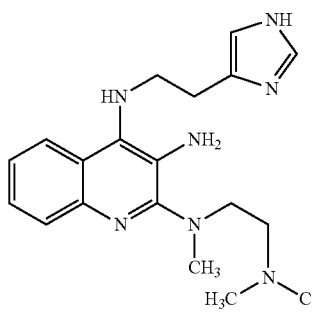

The crude nitro compound from above ($9.8 \times 10^{-3}$ moles) was dissolved in THF (150 mL) and was hydrogenated over 10% palladium on carbon (500 mg) at 50 psi of hydrogen on a Parr hydrogenator. The reduction was allowed to proceed overnight, after which, the Parr bottle was flushed with nitrogen and the clear, colorless solution was filtered to remove the catalyst. The THF was removed under vacuum and dry toluene (100 mL) was added.

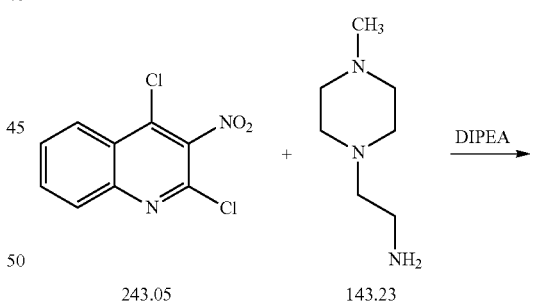

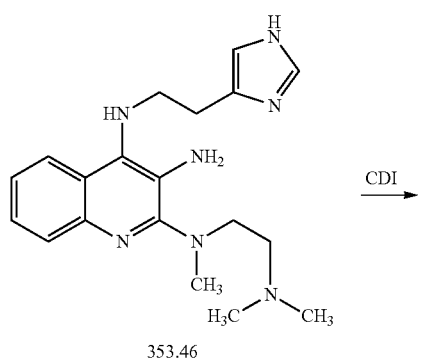

A solution of 2,4-dichloro-3-nitroquinoline (6.17 gm, $2.54 \times 10^{-2}$ moles) in tetrahydrofuran (100 mL) was stirred as diisopropylethylamine (3.62 gm, 4.88 mL, $2.8 \times 10^{-2}$ moles) and N-methyl-N'-(2-aminoethyl)piperazine (4.0 gm, 2.8×

10$^{-2}$ moles) were added. This solution was stirred at room temperature overnight. The THF was removed under reduced pressure and the remaining material was partitioned between methylene chloride (200 mL) and water (200 mL). The aqueous was extracted a second time with methylene chloride (100 mL). After being dried over magnesium sulfate, the combined extracts were filtered and the solvent was removed under reduced pressure. The remaining yellow oil was stirred with diethyl ether (50 mL) and this was cooled on ice causing the product to crystallize. The solid yellow product was isolated by filtration, washed with ether and dried. The yield was 3.6 gm (40.5%).

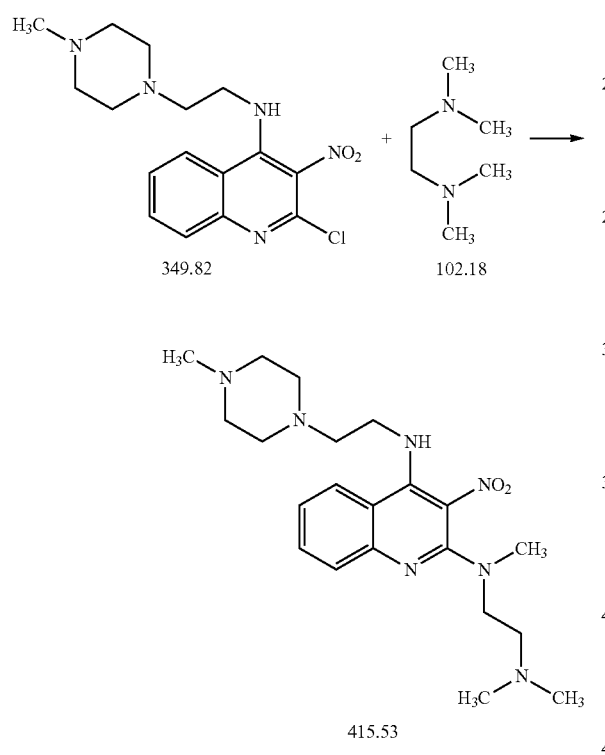

A solution of the chloronitroquinoline (3.49 gm, 1.0×10$^{-2}$ moles) in 2-butanol (50 mL) was treated with N,N,N'-trimethylethylenediamine (2.04 gm, 2.54 mL, 2.0×10$^{-2}$ moles). This mixture was heated at 100° C. for 2 hours. TLC (silica, 25% methanol in methylene chloride) showed complete conversion of the starting material (Rf=0.61) to a single product (Rf=0.33). After cooling, the solvent was removed under reduced pressure. The remaining material was partitioned between 5% potassium carbonate (100 mL) and methylene chloride (200 mL). The methylene chloride solution was dried over magnesium sulfate before being filtered and evaporated under reduced pressure. The remaining material was stirred in diethyl ether (100 mL) which caused the precipitation of a small amount of dark material. This was removed by filtration and the filtrates were evaporated under reduced pressure. The remaining red oily product was isolated in a yield of 3.88 gm.

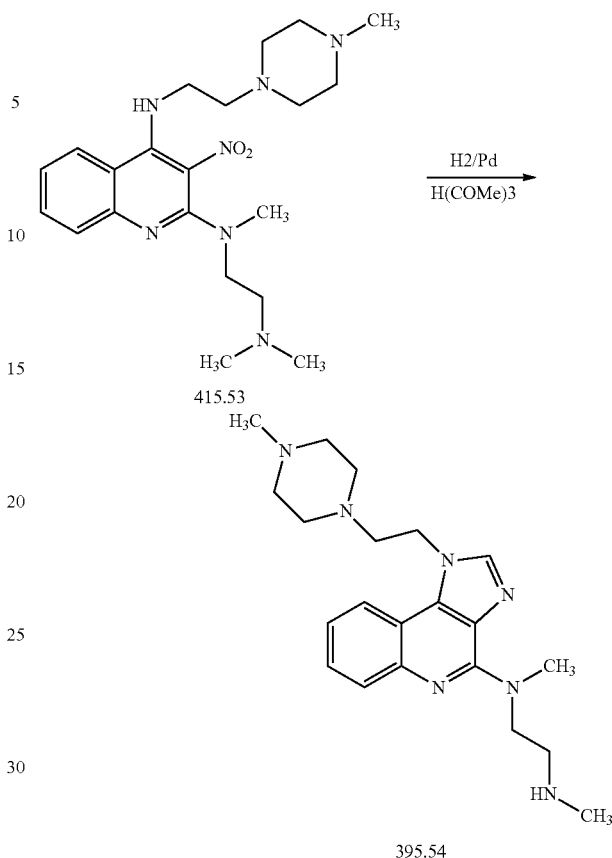

The crude nitro compound from above (9.33×10$^{-3}$ moles) was dissolved in methanol (50 mL) and was hydrogenated over 10% palladium on carbon (500 mg) at 50 psi of hydrogen on a Parr hydrogenator. The reduction was allowed to proceed until hydrogen uptake stopped, after which, the Parr bottle was flushed with nitrogen and the clear, colorless solution was filtered to remove the catalyst. The methanol was removed under reduced pressure and the remaining material was dissolved in formamide (25 mL). To this solution of the triamine was added trimethyl orthoformate (25 mL) and concentrated hydrochloric acid (5 mL). The solution was stirred et room temperature overnight. To the solution was added water (200 mL) and potassium carbonate (10 gm). After stirring for 5 the mixture was extracted with methylene chloride (2×150 mL) and the extract was dried over magnesium sulfate. After filtration, the methylene chloride was evaporated under reduced pressure. The remaining oil was dissolved in diethyl ether (150 mL), and the solution was stirred and treated with a solution of concentrated sulfuric acid (1.83 gm) in ether (50 mL). After stirring for 10 minutes, the solid sulfate salt was isolated by filtration, washed with ether and dried under vacuum to provide compound 70 sulfate in a yield of 3.9 gm. NMR (CDCl3) 2.20 ppm, singlet, 3H 2.30 ppm, singlet, 6H 2.45 ppm, multiplet, 8H 2.65 ppm, triplet, 2H 2.80 ppm, triplet, 2H 3.51 ppm, singlet, 3H 4.25 ppm, triplet, 2H 4.45 ppm, triplet, 2H 7.30 ppm, triplet, 1H 7.40 ppm, triplet, 1H 7.70 ppm, singlet, 1H 7.75 ppm, doublet, 1H 7.80 ppm, doublet, 1H. LC/MS M+1=396.51.

Biological Assays.

TLR9 Antagonist Assay.

HEK-Blue™-hTLR9 cells were obtained from InvivoGen Inc. and used to determine test compound antagonism of human TLR9 (hTLR9) driven responses. HEK-Blue™-hTLR9 cells are designed for studying the stimulation of human TLR9 by monitoring the activation of NF-kB. As described by the manufacturer, "HEK-Blue™-hTLR9 cells were obtained by co-transfection of the hTLR9 gene and an optimized secreted embryonic alkaline phosphatase (SEAP) reporter gene into HEK293 cells. The SEAP reporter gene is placed under the control of the IFN-b minimal promoter fused to five NF-kB and AP-1 binding sites. Stimulation with a TLR9 ligand activates NF-kB and AP-1 which induces the production of SEAP. Levels of SEAP can be easily determined with QUANTI-Blue™ a detection medium that turns purple/blue in the presence of alkaline phosphatase".

TLR9 Antagonism Assay

Day 1:

A cell suspension of HEK-Blue™-hTLR9 cells at ~450,000 cells per ml in test medium which contained 5% (v/v) heat inactivated FBS was prepared. 180 ul of cell suspension (~80,000 cells) was added per well of a flat-bottom 96-well plate and place in an incubator at 37° C. for overnight.

Day 2:

Test compounds were serially diluted in test medium, generally starting at 10 uM, and diluting by 3 fold in a 96 well master plate. 20 ul of diluted test compound was transferred using a 12 channel multi-channel pipet to the cell plate and incubated at 37° C. for 1 hour. Then 20 ul of an hTLR9 agonist (such as ODN 2006, 1 uM) was added to each well and the plate incubated at 37° C. overnight.

Day 3:

Invivogen's QUANTI-Blue™ was prepared following the manufacturer's instructions. 180 ml of resuspended QUANTI-Blue™ was added per well of a flat bottom 96-well plate. 20 ul per well of induced HEK-Blue™-hTLR9 cells supernatant was then added to the plate and the plate was incubated at 37° C. for 1-3 h. SEAP levels were determined using a spectrophotometer at 620 nm.

Calculation of $IC_{50}$

The concentration dependent inhibition of hTLR9 dependent SEAP production was expressed as the concentration of compound which produced half the maximal level of SEAP induced by the hTLR agonist alone. Percent activity was calculated for each observation using the formula: % activity=((observed O.D.−background O.D.)/(agonist only O.D.−background O.D.))*100. The 50% inhibitory concentration ($IC_{50}$) (Table 3) was calculated by using a 4 parameter Hill plot sigmoidal curve fit where the inflection point of the sigmoidal curve is defined as the point of 50% activity.

TABLE 3

| hTLR9 antagonism | |
| --- | --- |
| Example | nM $IC_{50}$ |
| 60 | 3408 |
| 61 | 389 |
| 62 | 713 |
| 63 | 3353 |
| 64 | 6693 |
| 65 | 56 |
| 66 | 323 |
| 67 | 143 |
| 68 | 136 |

TABLE 3-continued

| hTLR9 antagonism | |
| --- | --- |
| Example | nM $IC_{50}$ |
| 69 | 1648 |
| 70 | NT |

NT = not tested

The Effects of test articles on Toll-Like Receptor (TLR) Knockdown Following a Single Intraperitoneal Dose to Male C57Bl/6 Mice.

Toll-Like Receptor (TLR) knockdown effect of test articles was evaluated in a C57Bl/6J mouse. The results are summarized in Table 4. Primary end points included a terminal blood collection for analysis of cytokine production in response to CpG-DNA TLR9 agonist injection. Male C57Bl/6J mice, at ~8 weeks of age from Jackson Laboratories were used. Test groups were 3 mice per treatment group and the groups were administered test article in a series of descending doses within the range of 400 ug to 10 ug. Test article treatment was dosed at T=0 hr by intraperitoneal injection. Agonist (CpG ODN 1668) treatment was dosed one hour later, T=1 hr by intraperitoneal injection. Necropsy was performed 3 hours post agonist treatment, T=4 hr. Blood samples were collected into serum separator tubes, allowed to clot at room temperature for at least 20 minutes, centrifuged at ambient temperature at 3000 g for 10 minutes, and the serum was extracted. ELISA was performed to determine murine IL-12 levels following manufacture's protocol (BioLegend Inc.). Serum IL-12 levels were calculated and plotted versus administered dose of antagonist and inhibitory dose at 50% ($ID_{50}$) was determined.

TABLE 4

| In vivo TLR antagonism | |
| --- | --- |
| Example | ug $ID_{50}$ |
| 65 | 67 |
| 67 | 1262 |
| 68 | 280 |
| 70 | 111 |

The invention claimed is:

1. A compound of Formula I or a pharmaceutically acceptable salt thereof,

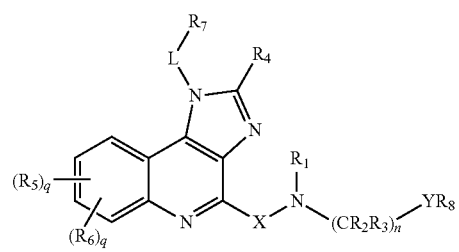

(I)

wherein
X is absent or is a cycloalkyl, aryl, or pyridyl;
each occurrence of $R_2$ and $R_3$ is independently hydrogen, alkyl, cycloalkyl, alkoxy, or —$(CH_2)_p NR_a R_b$, or $R_2$ and $R_3$ together with the carbon atom to which they are bonded optionally form a $(C_3\text{-}C_7)$cycloalkyl;

n is an integer of 2-4;

each q is an integer of 1-2;

Y is $NR_9$ or O;

$R_9$ is H, Me, Et, n-Pr, i-Pr, n-Bu, i-Bu, t-Bu, $CH_2CMe_3$, Ph, $CH_2Ph$, $C(=O)R_{12}$, $(CH_2)_pOR_a$, or $(CH_2)_{p'}NR_bR_c$, wherein $R_{12}$ is alkyl or phenyl; and p' is 2-4;

or said $R_8$ and $R_9$ together with the nitrogen atom to which they are bonded optionally form a heterocycle selected from the group consisting of

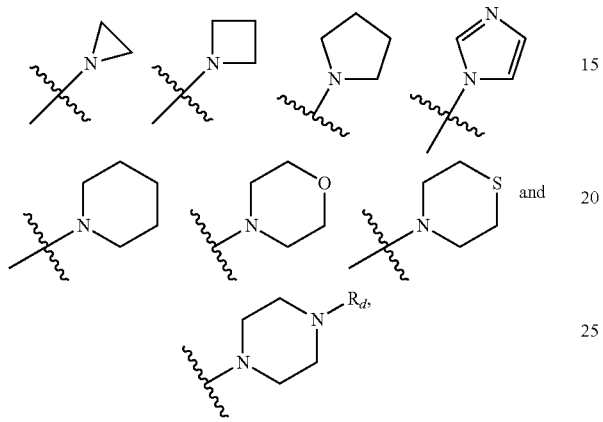

in which $R_d$ is H, Me, Et, n-Pr, i-Pr, n-Bu, i-Bu, t-Bu, $CH_2CMe_3$, Ph, or $CH_2Ph$;

$R_4$ is hydrogen, halogen, cyano, nitro, $CF_3$, $OCF_3$, alkyl, cycloalkyl, alkenyl, aryl, $OR_a$, —$CH_2OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_5$ and $R_6$ are each independently hydrogen, halogen, cyano, nitro, $CF_3$, $OCF_3$, alkyl, cycloalkyl, alkenyl, aryl, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_bC(=O)R_a$, alkaryl, or $NR_bC(CH_2)_pNR_bR_c$;

L is alkyl or alkenyl containing from 2 to 10 carbon atoms;

$R_7$ is $NR_{10}R_{11}$;

$R_{10}$ and $R_{11}$ are each independently hydrogen, alkyl, cycloalkyl, alkenyl, aryl or alkylaryl, or $R_{10}$ and $R_{11}$ together with the nitrogen atom to which they are bonded form a heterocycle selected from the group consisting of

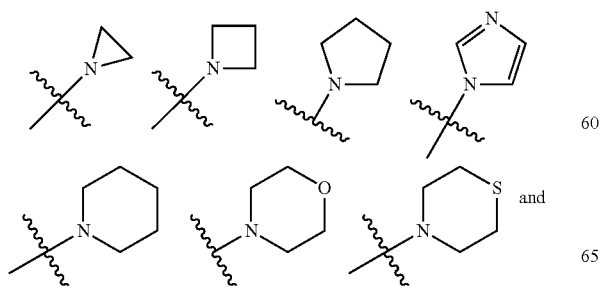

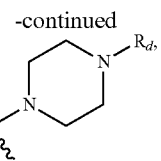

in which $R_d$ is H, Me, Et, n-Pr, i-Pr, n-Bu, i-Bu, t-Bu, $CH_2CMe_3$, Ph, or $CH_2Ph$;

p is an integer of 0, 1, 2, 3, 4, 5, or 6;

each occurrence of $R_a$ is independently hydrogen, alkyl, cycloalkyl, alkenyl, cycloalkenyl, alkynyl, or aryl;

each occurrence of $R_b$ and $R_c$ is independently hydrogen, alkyl, cycloalkyl, or aryl; and wherein when X is cycloalkyl, aryl, or pyridyl, $R_1$ is hydrogen or alkyl, and $R_8$ is hydrogen or alkyl, or $R_1$ and $R_8$ together form

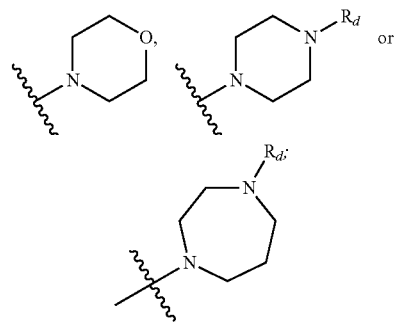

in which $R_d$ is H, Me, Et, n-Pr, i-Pr, n-Bu, i-Bu, t-Bu, $CH_2CMe_3$, Ph, or $CH_2Ph$; and when X is absent, $R_1$ is hydrogen or alkyl, and $R_8$ is hydrogen or alkyl.

2. The compound of claim 1, wherein X is cycloalkyl.

3. The compound of claim 1, wherein X is pyridyl.

4. The compound of claim 1, wherein L is alkyl or alkenyl containing from 2 to 4 carbon atoms.

5. The compound of claim 1 having the structure of Formula II:

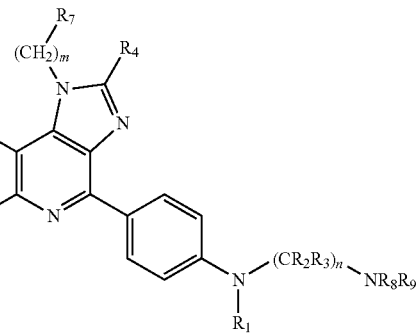

(II)

wherein each occurrence of $R_1$ is independently hydrogen or $(C_1$-$C_4)$alkyl;

each occurrence of $R_2$ and $R_3$ is independently hydrogen, $(C_1$-$C_4)$alkyl, $(C_3$-$C_7)$cycloalkyl, $(C_1$-$C_4)$alkoxy, or —(CH$_2$)$_p$NR$_a$R$_b$, or R$_2$ and R$_3$ together with the carbon atom to which they are bonded optionally form a (C$_3$-C$_6$)cycloalkyl;

p is an integer of 0, 1, 2, 3, 4, 5, or 6;

R$_8$ is hydrogen or (C$_1$-C$_4$)alkyl;

R$_9$ is H, Me, Et, n-Pr, i-Pr, n-Bu, i-Bu, t-Bu, CH$_2$CMe$_3$, Ph, CH$_2$Ph, C(=O)R$_{12}$, (CH$_2$)$_p$OR$_a$, or (CH$_2$)$_p$NR$_b$R$_c$, wherein R$_{12}$ is (C$_1$-C$_4$)alkyl or phenyl; R$_a$, R$_b$ and R$_c$ are each independently hydrogen, or (C$_1$-C$_4$)alkyl; and p' is 2-4;

or said R$_8$ and R$_9$ together with the nitrogen atom to which they are bonded optionally form a 3- to 7-membered heterocycle selected from the group consisting of

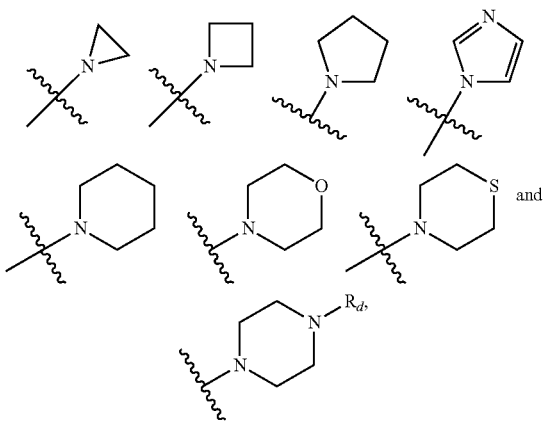

in which R$_d$ is H, Me, Et, n-Pr, i-Pr, n-Bu, i-Bu, t-Bu, CH$_2$CMe$_3$, Ph, or CH$_2$Ph;

or R$_1$ and R$_8$ together form

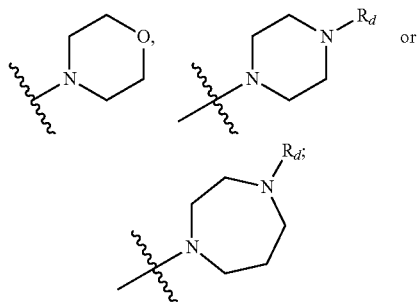

in which R$_d$ is H, Me, Et, n-Pr, i-Pr, n-Bu, i-Bu, t-Bu, CH$_2$CMe$_3$, Ph, or CH$_2$Ph;

R$_4$ is hydrogen, halogen, cyano, nitro, CF$_3$, OCF$_3$, (C$_1$-C$_4$)alkyl, (C$_3$-C$_7$)cycloalkyl, (C$_2$-C$_6$)alkenyl, aryl, OR$_a$, —CH$_2$OR$_a$, SR$_a$, S(=O)R$_a$, S(=O)$_2$R$_a$, NR$_b$R$_c$, S(=O)$_2$NR$_b$R$_c$, C(=O)OR$_a$, C(=O)R$_a$, C(=O)NR$_b$R$_c$, OC(=O)R$_a$, OC(=O)NR$_b$R$_c$, NR$_b$C(=O)OR$_a$, or NR$_b$C(=O)R$_a$;

R$_5$ and R$_6$ are each independently hydrogen, halogen, cyano, nitro, CF$_3$, OCF$_3$, (C$_1$-C$_4$)alkyl, (C$_3$-C$_7$)cycloalkyl, (C$_2$-C$_6$)alkenyl, aryl, OR$_a$, SR$_a$, S(=O)R$_a$, S(=O)$_2$R$_a$, NR$_b$R$_c$, S(=O)$_2$NR$_b$R$_c$, C(=O)OR$_a$, C(=O)R$_a$, C(=O)NR$_b$R$_c$, OC(=O)R$_a$, OC(=O)NR$_b$R$_c$, NR$_b$C(=O)OR$_a$, NR$_b$C(=O)R$_a$, alkaryl, or NR$_b$(CH$_2$)$_p$NR$_b$R$_c$; and m is an integer of 2-6.

6. The compound of claim 1 having the structure of Formula III:

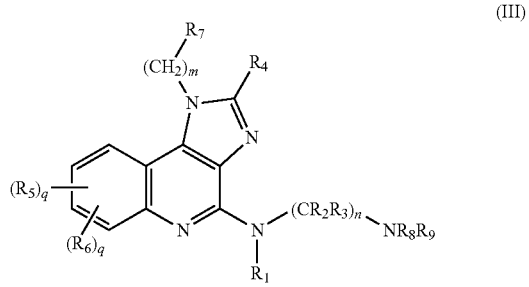

wherein
each occurrence of R$_1$ is hydrogen or (C$_1$-C$_4$)alkyl;
each occurrence of R$_2$ and R$_3$ is independently hydrogen, (C$_1$-C$_4$)alkyl, (C$_3$-C$_7$)cycloalkyl, (C$_1$-C$_4$)alkoxy, or —(CH$_2$)$_p$NR$_a$R$_b$, or R$_2$ and R$_3$ together with the carbon atom to which they are bonded optionally form a (C$_3$-C$_6$)cycloalkyl;
p is an integer of 0, 1, 2, 3, 4, 5, or 6;
R$_8$ is hydrogen or (C$_1$-C$_4$)alkyl;
R$_9$ is H, Me, Et, n-Pr, i-Pr, n-Bu, i-Bu, t-Bu, CH$_2$CMe$_3$, Ph, CH$_2$Ph, C(=O)R$_{12}$, (CH$_2$)$_p$OR$_a$, or (CH$_2$)$_p$NR$_b$R$_c$, wherein R$_{12}$ is (C$_1$-C$_4$)alkyl or phenyl; and p' is 2-4;
each occurrence of R$_a$ is independently hydrogen, alkyl, cycloalkyl, alkenyl, cycloalkenyl, alkynyl, or aryl;
each occurrence of R$_b$, and R$_c$ is independently hydrogen, alkyl, cycloalkyl, or aryl;
R$_4$ is hydrogen, halogen, cyano, nitro, CF$_3$, OCF$_3$, (C$_1$-C$_4$)alkyl, (C$_3$-C$_7$)cycloalkyl, (C$_2$-C$_6$)alkenyl, aryl, OR$_a$, —CH$_2$OR$_a$, SR$_a$, S(=O)R$_a$, S(=O)$_2$R$_a$, NR$_b$R$_c$, S(=O)$_2$NR$_b$R$_c$, C(=O)OR$_a$, C(=O)R$_a$, C(=O)NR$_b$R$_c$, OC(=O)R$_a$, OC(=O)NR$_b$R$_c$, NR$_b$C(=O)OR$_a$, or NR$_b$C(=O)R$_a$; and
m is an integer of 2-6.

7. The compound of claim 5, wherein R$_{10}$ and R$_{11}$ are each independently hydrogen, (C$_1$-C$_4$)alkyl, or (C$_1$-C$_4$)alkylaryl.

8. The compound of claim 5, wherein R$_{10}$ and R$_{11}$ together with the nitrogen atom to which they are bonded form a heterocycle selected from the group consisting of

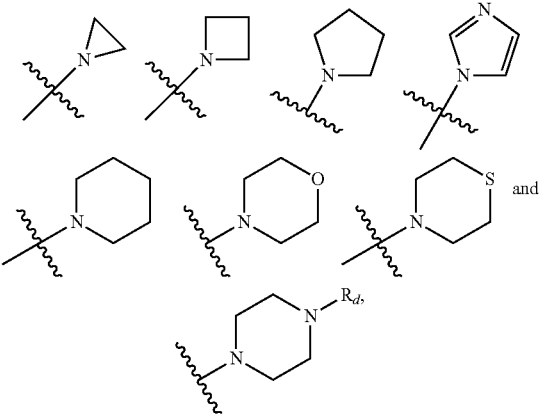

in which R$_d$ is H, Me, Et, n-Pr, i-Pr, n-Bu, i-Bu, t-Bu, CH$_2$CMe$_3$, Ph, or CH$_2$Ph.

9. The compound of claim 1, wherein $NR_{10}R_{11}$ and $NR_8R_9$ are each independently a heterocycle selected from the group consisting of

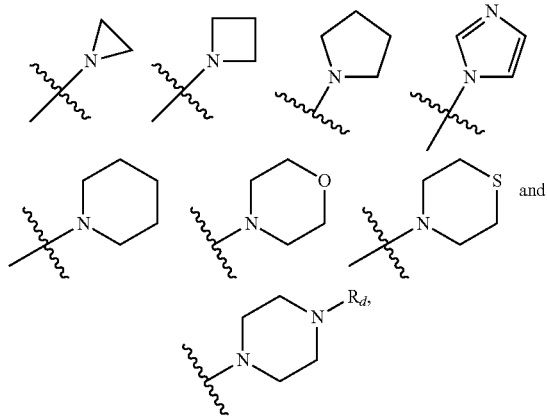

in which $R_d$ is H, Me, Et, n-Pr, i-Pr, n-Bu, i-Bu, or t-Bu.

10. The compound of claim 1, wherein $NR_{10}R_{11}$ and $NR_8R_9$ are each independently a heterocycle selected from the group consisting of

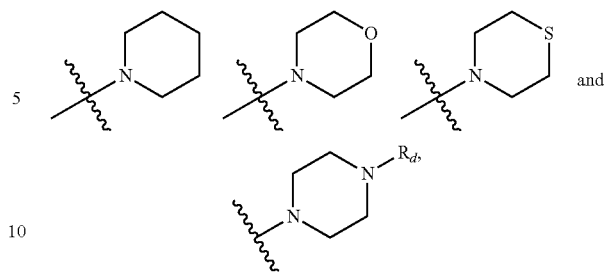

in which $R_d$ is H, Me, Et, n-Pr, i-Pr, n-Bu, i-Bu, or t-Bu.

11. The compound of claim 1, wherein X is cycloalkyl or aryl.

12. The compound of claim 1, wherein X is absent.

13. The compound of claim 1, wherein $R_1$ is H.

14. The compound of claim 1, wherein $R_2$ and $R_3$ are each independently H.

15. A compound of claim 1 selected from the group consisting of the compounds 4-6, 8-15, 17-20, 25-34, 36-39, 41-43, 50-51, 53, 55, 59-61, 65, 67-68, and 70 from Tables 1-2:

TABLE 1

| Compound No. | X | $\underset{(CR_2R_3)_n}{\overset{R_1}{\underset{|}{N}}}YR_8$ | L | $R_7$ | $R_4$ | $R_5, R_6$ |
|---|---|---|---|---|---|---|
| 4 | p-tolyl | N-methylpiperazinyl-CH₃ | —(CH₂)₂— | N(CH₃)₂ | CH₃ | H, H |
| 5 | p-tolyl | N-methylpiperazinyl-CH₃ | —(CH₂)₂— | N(CH₃)₂ | CH₂OEt | H, H |
| 6 | p-tolyl | N-methylpiperazinyl-CH₃ | —(CH₂)₂— | N(CH₃)₂ | phenyl | CH₃, CH₃ |
| 8 | p-tolyl | N-methylpiperazinyl-CH₃ | —(CH₂)₂— | morpholinyl | SH | H, H |
| 9 | p-tolyl | N-methylpiperazinyl-CH₃ | —(CH₂)₂— | morpholinyl | Br | H, H |
| 10 | p-tolyl | N-methylpiperazinyl-CH₃ | —(CH₂)₂— | morpholinyl | Cl | H, H |

TABLE 1-continued

| Compound No. | X | $\begin{array}{c} R_1 \\ \diagdown N \diagup YR_8 \\ (CR_2R_3)_n \end{array}$ | L | $R_7$ | $R_4$ | $R_5, R_6$ |
|---|---|---|---|---|---|---|
| 11 | 1,4-phenylene | N-methylpiperazinyl, CH₃ | —(CH₂)₂— | N-methylmorpholine | SCH₃ | H, H |
| 12 | 1,4-phenylene | N-methylpiperazinyl, CH₃ | —(CH₂)₂— | N-methylmorpholine | SO₂CH₃ | H, H |
| 13 | 1,4-phenylene | N-methylpiperazinyl, CH₃ | —(CH₂)₂— | N-methylmorpholine | OCH₃ | H, H |
| 14 | 1,4-phenylene | N-methylpiperazinyl, CH₃ | —(CH₂)₂— | N(CH₃)₂ | OH | H, phenyl |
| 15 | 1,3-phenylene | N-methylpiperazinyl, CH₃ | —(CH₂)₂— | N-methylmorpholine | H | H, H |
| 17 | 1,4-phenylene | N-methylpiperazinyl, CH₃ | —(CH₂)₂— | N-methylmorpholine | CH₂OEt | H, H |
| 18 | 1,2-phenylene | CH₃NH—CH₂CH₂N(CH₃)₂ | —(CH₂)₂— | N-methylpiperazinyl, CH₃ | CH₂OEt | H, H |
| 19 | 1,2-phenylene | CH₃NH—CH₂CH₂N(CH₃)₂ | —(CH₂)₂— | N-methylmorpholine | H | CH₃, CH₃ |

TABLE 1-continued

| Compound No. | X | $\overset{R_1}{\underset{(CR_2R_3)_n}{N}}YR_8$ | L | $R_7$ | $R_4$ | $R_5, R_6$ |
|---|---|---|---|---|---|---|
| 20 | 2,3-dimethylphenyl | —N(H)—(CH$_2$)$_3$N(CH$_3$)$_2$ | —(CH$_2$)$_2$— | N(CH$_3$)$_2$ | OH | H, H; | and

TABLE 2

| Example No. | $\overset{R_1}{\underset{(CR_2R_3)_n}{\overset{|}{X-N}}}YR_8$ | L | $R_7$ | $R_4$ | $R_5, R_6$ |
|---|---|---|---|---|---|
| 25 | 4-methylphenyl-piperazinyl-N-CH$_3$ | —(CH$_2$)$_4$— | N-methylmorpholine | H | H, H |
| 26 | 4-methylphenyl-piperazinyl-N-CH$_3$ | —(CH$_2$)$_3$— | N-methylmorpholine | CH$_3$ | H, H |
| 27 | 4-methylphenyl-piperazinyl-N-CH$_3$ | —(CH$_2$)$_4$— | N(CH$_3$)$_2$ | CH$_2$OEt | H, H |
| 28 | 4-methylphenyl-piperazinyl-N-CH$_3$ | —(CH$_2$)$_5$— | N(CH$_3$)$_2$ | CH$_2$OEt | H, H |
| 29 | 3-methylphenyl-piperazinyl-N-CH$_3$ | —(CH$_2$)$_2$— | N(CH$_3$)$_2$ | OH | CH$_3$, Et |
| 30 | 4-methylphenyl-piperazinyl-N-CH$_3$ | —(CH$_2$)$_2$— | N(Et)$_2$ | OH | H, H |

TABLE 2-continued
| Example No. | 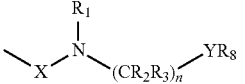 X-N(R₁)-(CR₂R₃)ₙ-YR₈ | L | R₇ | R₄ | R₅, R₆ |
|---|---|---|---|---|---|
| 31 | 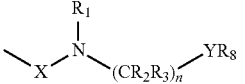 | —(CH₂)₄— | N(CH₃)₂ | CH₂OEt | H, 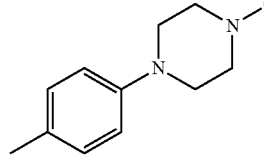 |
| 32 | 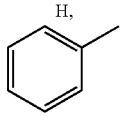 | —(CH₂)₂— | NEtPh | Et | Et, Et |
| 33 | 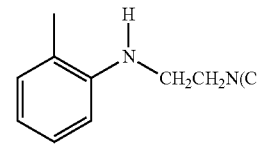 | —(CH₂)₂— | N(CH₃)₂ | CH₃ | H, H |
| 34 | 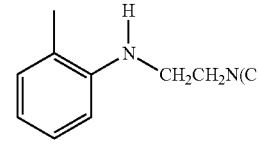 | —(CH₂)₅— | N(CH₃)₂ | CH₂OEt | H, H |
| 36 | 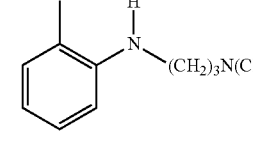 | —(CH₂)₄— | 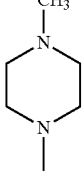 | CH₃ | F, H |
| 37 | 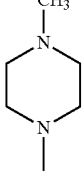 | —(CH₂)₄— | 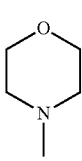 | n-Pr | CH₃, n-Bu |
| 38 | 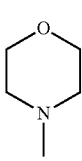 | —(CH₂)₂— | 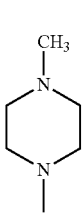 | CH₃ | CH₃, n-Bu |
| 39 | 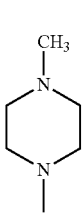 | —(CH₂)₂— | N(CH₃)₂ | CH₂OEt | F, Cl |

TABLE 2-continued

| Example No. | X-N(R1)-(CR2R3)n-YR8 | L | R7 | R4 | R5, R6 |
|---|---|---|---|---|---|
| 41 | 3-methylphenyl-N-piperazinyl-N-CH3 | —(CH2)2— | N(CH3)2 | CH2OEt | Cl, H |
| 42 | 4-methylcyclohexyl-piperazinyl-N-CH3 | —(CH2)2— | N(CH3)2 | CH2OEt | Cl, Cl |
| 43 | 5-methylpyridin-2-yl-piperazinyl-N-CH3 | —(CH2)2— | N(CH3)2 | CH2OEt | H, H |
| 50 | MeHN-CH2CH2-morpholine | —(CH2)3— | NHBn | OH | H, H |
| 51 | MeHN-CH2CH2-NH-CH2-Ph | —(CH2)2— | NHBn | CH2OEt | H, H |
| 53 | MeHN-CH2CH2-N(Me)-CH2-Ph | —(CH2)2— | NHMe | CH2OEt | H, H |
| 55 | MeHN-CH2CH2-N(CH3)2 | —(CH2)2— | N-methylpiperazinyl | Et | H, OCF3 |
| 59 | ⁓N(H)-CH2CH2-N(CH3)2 | —(CH2)2— | N-methylpiperazinyl | Et | R5 = H, R6 = n-propyl |
| 60 | ⁓N(Me)-CH2CH2-NMe2 | —(CH2)2— | morpholinyl | CH2OEt | R5 = H, R6 = H |
| 61 | ⁓N(Me)-CH2CH2-NMe2 | —(CH2)2— | NMe2 | CH2OEt | R5 = H, R6 = H |

TABLE 2-continued

| Example No. | ![X-N(R1)-(CR2R3)n-YR8 structure] | L | R7 | R4 | R5, R6 |
|---|---|---|---|---|---|
| 65 | N-CH2CH2-NMe2 (N-methyl) | —(CH2)2— | N-methylpiperazinyl (Me) | CH2OEt | R5 = H, R6 = H |
| 67 | N-CH2CH2-NMe2 (N-methyl) | —(CH2)2— | NMe2 | H | R5 = H, R6 = H |
| 68 | N-CH2CH2-NMe2 (N-methyl) | —(CH2)2— | NMe2 | OH | R5 = H, R6 = H |
| 70 | N-CH2CH2-NHCH3 (N-methyl) | —(CH2)2— | N-methylpiperazinyl (Me) | H | R5 = H, R6 = H. |

16. A pharmaceutical composition comprising at least one compound according to claim 1 and a pharmaceutically-acceptable carrier or diluent.

17. A method of inhibiting TLR-mediated immunostimulation in a mammalian species in need thereof, comprising administering to the mammalian species a therapeutically effective amount of at least one compound according to claim 1.

18. A method of inhibiting TLR-mediated immunostimulatory signaling, comprising contacting a cell expressing a TLR with an effective amount of at least one compound according to claim 1.

19. The compound of claim 6, wherein $R_{10}$ and $R_{11}$ are each independently hydrogen or $(C_1\text{-}C_4)$alkyl.

20. The compound of claim 6, wherein $R_7$ is $NR_{10}R_{11}$, in which $R_{10}$ and $R_{11}$ together with the nitrogen atom to which they are bonded form a heterocycle selected from the group consisting of

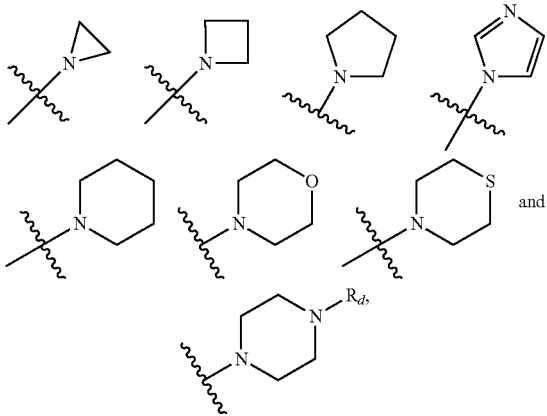

in which $R_d$ is H, Me, Et, n-Pr, i-Pr, n-Bu, i-Bu, t-Bu, $CH_2CMe_3$, Ph, or $CH_2Ph$.

* * * * *